US010253080B2

(12) United States Patent
Just et al.

(10) Patent No.: US 10,253,080 B2
(45) Date of Patent: *Apr. 9, 2019

(54) GLUCAGON-LIKE-PEPTIDE-2 (GLP-2) ANALOGUES

(71) Applicant: Zealand Pharma A/S, Glostrup (DK)

(72) Inventors: Rasmus Just, Copenhagen (DK); Kirsten Lindegaard Bovbjerg, Hørsholm (DK); Ditte Riber, Brønshøj (DK); Wayne Shaun Russell, Kävlinge (SE)

(73) Assignee: Zealand Pharma A/S, Glostrup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/950,235

(22) Filed: Apr. 11, 2018

(65) Prior Publication Data

US 2018/0298077 A1    Oct. 18, 2018

Related U.S. Application Data

(63) Continuation of application No. 15/238,126, filed on Aug. 16, 2016, now Pat. No. 9,969,787, which is a continuation of application No. 14/398,297, filed as application No. PCT/EP2013/059320 on May 3, 2013, now Pat. No. 9,453,064.

(60) Provisional application No. 61/785,852, filed on Mar. 14, 2013, provisional application No. 61/642,447, filed on May 3, 2012.

(51) Int. Cl.

| A61K 38/00 | (2006.01) |
| A61K 14/00 | (2006.01) |
| C07K 14/605 | (2006.01) |
| A61K 38/26 | (2006.01) |
| A61K 35/22 | (2015.01) |
| A61K 35/48 | (2015.01) |
| A61K 35/54 | (2015.01) |
| A61K 35/64 | (2015.01) |
| A61K 45/06 | (2006.01) |
| A61K 35/63 | (2015.01) |

(52) U.S. Cl.
CPC ............ *C07K 14/605* (2013.01); *A61K 35/22* (2013.01); *A61K 35/48* (2013.01); *A61K 35/54* (2013.01); *A61K 35/63* (2015.01); *A61K 35/64* (2013.01); *A61K 38/26* (2013.01); *A61K 45/06* (2013.01)

(58) Field of Classification Search
None
See application file for complete search history.

(56) References Cited

U.S. PATENT DOCUMENTS

| 5,432,156 A | 7/1995 | Matsuno et al. |
| 5,789,379 A | 8/1998 | Drucker et al. |
| 5,834,428 A | 11/1998 | Drucker |
| 5,912,229 A | 6/1999 | Thim et al. |
| 5,952,301 A | 9/1999 | Drucker |
| 5,990,077 A | 11/1999 | Drucker |
| 5,994,500 A | 11/1999 | Drucker et al. |
| 6,051,557 A | 4/2000 | Drucker |
| 6,184,201 B1 | 2/2001 | Drucker et al. |
| 6,184,208 B1 | 2/2001 | Deigin et al. |
| 6,297,214 B1 | 10/2001 | Drucker |
| 6,489,295 B1 | 12/2002 | Drucker et al. |
| 6,586,399 B1 | 7/2003 | Drucker |
| 6,770,620 B2 | 8/2004 | Henriksen |
| 7,049,284 B2 | 5/2006 | Drucker |
| 7,176,182 B2 | 2/2007 | Drucker |
| 7,186,683 B2 | 3/2007 | Henriksen et al. |
| 7,371,721 B2 | 5/2008 | Henriksen et al. |
| 7,411,039 B2 | 8/2008 | Thim et al. |
| 7,563,770 B2 | 7/2009 | Larsen et al. |
| 7,737,251 B2 | 6/2010 | Bridon et al. |
| 7,745,403 B2 | 6/2010 | Larsen et al. |
| 8,163,696 B2 | 4/2012 | Larsen et al. |
| 8,263,552 B2 | 9/2012 | Larsen et al. |
| 8,642,727 B2 | 2/2014 | Larsen et al. |
| 9,125,882 B2 | 9/2015 | Larsen et al. |
| 9,453,064 B2 | 9/2016 | Just et al. |
| 9,580,487 B2 | 2/2017 | Larsen et al. |
| 2001/0021767 A1 | 9/2001 | Drucker et al. |
| 2002/0025933 A1 | 2/2002 | Knudsen et al. |
| 2003/0040478 A1 | 2/2003 | Drucker et al. |
| 2003/0109449 A1 | 6/2003 | Drucker et al. |
| 2003/0158101 A1 | 8/2003 | Drucker |
| 2003/0162703 A1 | 8/2003 | Drucker et al. |
| 2003/0207809 A1 | 11/2003 | Drucker |
| 2004/0052862 A1 | 3/2004 | Henriksen et al. |

(Continued)

FOREIGN PATENT DOCUMENTS

| EP | 1231218 B1 | 8/2002 |
| EP | 1231219 A1 | 8/2002 |

(Continued)

OTHER PUBLICATIONS

"Zollinger-Ellison Syndrome", The National Institute of Diabetes and Digestive and Kidney Diseases, <https://www.niddk.nih.gov/health-information/digestive-diseases/zollinger-ellison-syndrome>, accessed Oct. 16, 2017 (10 pages).

(Continued)

*Primary Examiner* — Jeanette M Lieb

(74) *Attorney, Agent, or Firm* — Clark & Elbing LLP

(57) ABSTRACT

GLP-2 analogs are disclosed which comprise one of more substitutions as compared to h[Gly2]GLP-2 and which may have the property of an altered GLP-1 activity, and their medical use. The analogs are particularly useful for the prophylaxis treatment or ameliorating of the gastro-intestinal associated side effects of diabetes.

35 Claims, 4 Drawing Sheets

Specification includes a Sequence Listing.

(56) References Cited

U.S. PATENT DOCUMENTS

| | | | |
|---|---|---|---|
| 2004/0122210 | A1 | 6/2004 | Thim et al. |
| 2004/0127418 | A1 | 7/2004 | Knudsen et al. |
| 2004/0198642 | A1 | 10/2004 | Drucker et al. |
| 2004/0248782 | A1 | 12/2004 | Bridon et al. |
| 2005/0282749 | A1 | 12/2005 | Henriksen et al. |
| 2006/0105954 | A1 | 5/2006 | Drucker |
| 2006/0135424 | A1 | 6/2006 | Sanguinetti et al. |
| 2007/0117752 | A1 | 5/2007 | Larsen et al. |
| 2007/0231308 | A1 | 10/2007 | Larsen et al. |
| 2009/0082309 | A1 | 3/2009 | Bachovchin et al. |
| 2011/0098222 | A1 | 4/2011 | Larsen et al. |
| 2011/0152186 | A1 | 6/2011 | Larsen et al. |
| 2012/0004392 | A1 | 1/2012 | Larsen et al. |
| 2012/0289466 | A1 | 11/2012 | Larsen et al. |
| 2014/0154214 | A1 | 6/2014 | Larsen et al. |
| 2015/0125431 | A1 | 5/2015 | Just et al. |
| 2016/0355563 | A1 | 12/2016 | Just et al. |
| 2017/0137487 | A1 | 5/2017 | Larsen et al. |

FOREIGN PATENT DOCUMENTS

| | | | |
|---|---|---|---|
| EP | 0891378 | B1 | 11/2002 |
| EP | 0906338 | B1 | 11/2002 |
| EP | 0981362 | B1 | 11/2003 |
| EP | 0830377 | B1 | 10/2009 |
| EP | 1414486 | B1 | 5/2010 |
| WO | WO-96/32414 | A1 | 10/1996 |
| WO | WO-97/31943 | A1 | 9/1997 |
| WO | WO-97/39031 | A1 | 10/1997 |
| WO | WO-98/03547 | A1 | 1/1998 |
| WO | WO-98/11125 | A1 | 3/1998 |
| WO | WO-98/52600 | A1 | 11/1998 |
| WO | WO-99/46283 | A1 | 9/1999 |
| WO | WO-99/58144 | A1 | 11/1999 |
| WO | WO-01/04156 | A1 | 1/2001 |
| WO | WO-01/41779 | A2 | 6/2001 |
| WO | WO-02/24214 | A2 | 3/2002 |
| WO | WO-02/066511 | A2 | 8/2002 |
| WO | WO-02/098348 | A2 | 12/2002 |
| WO | WO-2004/035624 | A2 | 4/2004 |
| WO | WO-2005/027978 | A2 | 3/2005 |
| WO | WO-2005/082404 | A2 | 9/2005 |
| WO | WO-2006/117565 | A2 | 11/2006 |
| WO | WO-2008/056155 | A1 | 5/2008 |
| WO | WO-2010/070251 | A1 | 6/2010 |
| WO | WO-2011/160630 | A2 | 12/2011 |
| WO | WO-2012/158965 | A2 | 11/2012 |

OTHER PUBLICATIONS

Alison et al., "The role of growth factors in gastrointestinal cell proliferation," Cell Biol Int. 18(1):1-10 (1994).

Altschul et al., "Local alignment statistics," Methods Enzymol. 226:460-80 (1996).

Baldassano et al., "GLP-2: What do we know? What are we going to discover?," Regul Pept. 194-195:6-10 (2014).

Baldwin et al., "Gut hormones, growth and malignancy," Bailliére's Clin Endocrinol Metab. 8(1):185-214 (1994).

Bamba et al., "Enteroglucagon. A putative humoral factor including pancreatic hyperplasia after proximal small bowel resection," Dig Dis Sci. 39(7):1532-36 (1994).

Barragán et al., "Changes in arterial blood pressure and heart rate induced by glucagon-like peptide-1-(7-36) amide in rats," Am J Physiol. 266(3 Pt1):E459-66 (1994).

Benjamin et al., "Glucagon-like peptide-2 enhances intestinal epithelial barrier function of both transcellular and paracellular pathways in the mouse," Gut. 47(1):112-9 (2000).

Bloom, "Gut hormones in adaptation," Gut. 28(Suppl):31-5 (1987).

Booth et al., "Teduglutide ([Gly2]GLP-2) protects small intestinal stem cells from radiation damage," Cell Prolif. 37(6):385-400 (2004).

Boushey et al., "Glucagon-like peptide (GLP)-2 reduces chemotherapy-associated mortality and enhances cell survival in cells expressing a transfected GLP-2 receptor," Cancer Res. 61(2):687-93 (2001).

Boushey et al., "Glucagon-like peptide 2 decreases mortality and reduces the severity of indomethacin-induced murine enteritis," Am J Physiol. 227(5 Pt 1):E937-47 (1999).

Bowie et al., "Deciphering the message in protein sequences: tolerance to amino acid substitutions," Science. 247(4948):1306-10 (1990).

Brubaker et al., "Alterations in proglucagon processing and inhibition of proglucagon gene expression in transgenic mice which contain a chimeric proglucagon-SV40 T antigen gene," J Biol Chem. 267(29):20728-33 (1992).

Cavanaugh et al., "Isolation and structural characterization of proglucagon-derived peptides, pancreatic polypeptide, and somatostatin from the urodele Amphiuma tridactylum," Gen Comp Endocrinol. 101(1):12-20 (1996).

Cheeseman, "Upregulation of SGLT-1 transport activity in rat jejunum induced by GLP-2 infusion in vivo," Am J Physiol. 273(6 Pt 2):R1965-71 (1997).

Code, "The digestive system," Annu Rev Physiol. 15:107-38 (1953).

Creson et al., "Powdered duodenal extract in the treatment of peptic ulcer," Am J Gastroenterol. 33:359-65 (1960).

DaCambra et al., "Structural determinants for activity of glucagon-like peptide-2," Biochemistry. 39(30):8888-94 (2000).

Drucker et al., "Biologic properties and therapeutic potential of glucagon-like peptide-2," JPEN J Patenter Enteral Nutr. 23(5):S98-100 (1999).

Drucker et al., "Human [Gly2]GLP-2 reduces the severity of colonic injury in a murine model of experimental colitis," Am J Physiol. 276(1 Pt 1):G79-91 (1999).

Drucker et al., "Induction of intestinal epithelial proliferation by glucagon-like peptide 2," Proc Nat Acad Sci U.S.A. 93(15):7911-6 (1996).

Drucker et al., "Physiology and pharmacology of the enteroendocrine hormone glucagon-like peptide-2," Annu Rev Physiol. 76:561-83 (2014).

Drucker et al., "Regulation of the biological activity of glucagon-like peptide 2 in vivo by dipeptidyl peptidase IV," Nat Biotechnol. 15(7):673-7 (1997).

Drucker, "Glucagon-like peptide 2," J Clin Endocrinol Metab. 86(4):1759-64 (2001).

Drucker, "Minireview: The glucagon-like peptides," Endocrinology. 142(2):521-7 (2001).

Feinberg et al., "Period and amplitude analysis of 0.5-3 c/sec activity in NREM sleep of young adults," Electroencephalogr Clin Neurophysiol. 44(2):202-13 (1978).

Ferrone et al., "Teduglutide for the treatment of short bowel syndrome," Ann Pharmacother. 40(6):1105-9 (2006).

Gadermann et al., "[Treatment of gastroduodenal ulcerations & inflammations with the tissue extract robadin]," Med Klin (Munich). 54(16):774-8 (1959) (English translation).

Gibson et al., "Irinotecan causes severe small intestinal damage, as well as colonic damage, in the rat with implanted breast cancer," J Gastroenterol Hepatol. 18(9):1095-100 (2003).

Gibson et al., "Relative roles of spatial and intensive cues in the discrimination of spatial tactile stimuli," Percept Pyschophys. 64(7):1095-107 (2002).

Glass et al., "Studies on robuden, extract from stomach and duodenum: its effects upon gastric secretion and clinical course of peptic ulcer," Am J Dig Dis. 4(12):988-1013 (1959).

Gregor et al., "The role of gut-glucagon-like immunoreactants in the control of gastrointestinal epithelial cell renewal," Digestion. 46(Suppl 2):59-65 (1990).

Grey et al., "A growth-stimulating activity derived from the proximal small intestine is associated with an adaptive response," Can J Physiol Pharmacol. 68(5):646-9 (1990).

Grey et al., "Detection of growth-stimulating activity in the proximal small intestine during weaning in the suckling rat," Biol Neonate. 59(1):37-45 (1991).

Grey et al., "Evidence for a growth-stimulating fraction in the rat proximal intestine after small bowel resection," Gastroenterology. 89(6):1305-12 (1985).

(56) References Cited

OTHER PUBLICATIONS

Guan et al., "GLP-2-mediated up-regulation of intestinal blood flow and glucose uptake is nitric oxide-dependent in TPN-fed piglets," Gastroenterology. 125(1):136-47 (2003).
International Preliminary Report on Patentability from PCT/GB2006/001633, dated Nov. 6, 2007 (10 pages).
International Preliminary Report on Patentability from PCT/GB2007/004273, dated May 12, 2009 (9 pages).
International Search Report and Written Opinion for International Application No. PCT/EP2013/059320, dated Aug. 8, 2013 (11 pages).
International Search Report from PCT/GB2006/001633, dated Oct. 24, 2006 (6 pages).
International Search Report from PCT/GB2007/004273, dated Apr. 14, 2008 (4 pages).
Irwin et al., "Trout and chicken proglucagon: alternative splicing generates mRNA transcripts encoding glucagon-like peptide 2," Mol Endocrinol. 9(3):267-77 (1995).
Jenkins et al., "Mechanisms of small intestinal adaptation," Dig Dis. 12(1):15-27 (1994).
Jeppesen et al., "Teduglutide (ALX-0600), a dipeptidyl peptidase IV resistant glucagon-like peptide 2 analogue, improves intestinal function in short bowel syndrome patients," Gut. 54(9):1224-31 (2005).
Jeppesen, "The use of hormonal growth factors in the treatment of patients with short-bowel syndrome," Drugs. 66(5):581-9 (2006).
Keefe et al., "Chemotherapy for cancer causes apoptosis that precedes hypoplasia in crypts of the small intestine in humans," Gut. 47(5):632-7 (2000).
Kieffer et al., "The glucagon-like peptides," Endocr Rev. 20(6):876-913 (1999).
Kyte et al., "A simple method for displaying the hydropathic character of a protein," J Mol Biol. 157(1):105-32 (1982).
Larsen et al., "Incomplete Fmoc deprotection in solid-phase synthesis of peptides," Int J Pept Protein Res. 43(1):1-9 (1994).
Lentze, "Intestinal adaptation in short-bowel syndrome," Eur J Pediatr. 148(4):294-9 (1989).
Lopez et al., "Mammalian pancreatic preproglucagon contains three glucagon-related peptides," Proc Natl Acad Sci U.S.A. 80(18):5485-9 (1983).
Meier et al., "Glucagon-like peptide 2 stimulates glucagon secretion, enhances lipid absorption, and inhibits gastric acid secretion in humans," Gastroenterology. 130(1):44-54 (2006).
Mentlein et al., "Dipeptidyl-peptidase IV hydrolyses gastric inhibitory polypeptide, glucagon-like peptide-1(7-36)amide, peptide histidine methionine and is responsible for their degradation in human serum," Eur J Biochem. 214(3):829-35 (1993).
Miazza et al., "Hyperenteroglucagonaemia and small intestinal mucosal growth after colonic perfusion of glucose in rats," Gut. 26(5):518-24 (1985).
Moon et al., "Tyr1 and Ile7 of glucose-dependent insulinotropic polypeptide (GIP) confer differential ligand selectivity toward GIP and glucagon-like peptide-1 receptors," Mol Cells. 30(2):149-54 (2010).
Moore et al.,"GLP-2 receptor agonism ameliorates inflammation and gastrointestinal stasis in murine postoperative ileus," J Pharmacol Exp Ther. 333(2):574-83 (2010).
Myojo et al., "Trophic effects of glicentin on rat small-intestinal mucosa in vivo and in vitro," J Gastroenterol. 32(3):300-5 (1997) (English abstract).
Neumann, "Experiences with medications: A review of 12 years of peptic ulcer treatment with Robuden," Schweiz Med Wochenschr. 87(32):1049-1051 (1957) (English translation).
Notice of Opposition for European Patent No. EP1877435, dated Nov. 22, 2011 (29 pages).
Notkin et al., "Gastroduodenal tissue extracts in the treatment of peptic ulcer with special reference to the effectiveness of robuden," Am J Dig Dis. 21(9):251-61 (1954).
Oben et al., "Effect of the entero-pancreatic hormones, gastric inhibitory polypeptide and glucagon-like polypeptide-1(7-36) amide, on fatty acid synthesis in explants of rat adipose tissue," J Endocrinol. 130(2):267-72 (1991).
Office Action issued for Japanese Patent Application No. 2008-509505, dated Sep. 6, 2011 (11 pages).
Ørskov et al., "Glucagon-Like peptides GLP-1 and GLP-2, predicted products of the glucagon gene, are secreted separately from pig small intestine but not pancreas," Endocrinology. 119(4):1467-75 (1986).
Petersen et al., "Administration of the protease-resistant glucagon-like peptide 2 analog, [gly2]GLP-2, prior to and concurrently with the chemotherapeutic agent, 5-fluorouracil, inhibits small intestinal atrophy and attenuates bodyweight loss in mice," Gastroenterol. 128(4; Supplement 2): A188 (2005) (1 page).
Pouliot et al., "Follow-up studies on peptic ulcer patients treated with robuden," Can Med Assoc J. 82:524-8 (1960).
Response to Notice of Opposition for European Patent No. 1877435, filed Jun. 25, 2012 (6 pages).
Richter et al., "GLP-1 stimulates secretion of macromolecules from airways and relaxes pulmonary artery," Am J Physiol. 265(4 Pt 1):L374-81 (1993).
Ruiz-Grande et al., "Lipolytic action of glucagon-like peptides in isolated rat adipocytes," Peptides. 13(1):13-6 (1992).
Sasaki et al., "Enteroglucagon, but not CCK, plays an important role in pancreatic hyperplasia after proximal small bowel resection," J Gastroenterol Hepatol. 9(6):576-81 (1994).
Sinclair et al., "Proglucagon-derived peptides: mechanisms of action and therapeutic potential," Physiology (Bethesda). 20:357-65 (2005).
Singh et al., "Use of 125I-[Y39]exendin-4 to characterize exendin receptors on dispersed pancreatic acini and gastric chief cells from guinea pig," Regul Pept. 53(1):47-59 (1994).
Skarbaliene et al., "ZP1848, a novel GLP-2 agonist, provides a wide window of therapeutic efficacy in the experimental Crohn's disease model," Gastroenterol. 140(5 Suppl 1):S-519, abstract Su1953 (2011) (1 page).
Submission in opposition proceedings made following summons to attend oral proceedings for European Patent No. 1877435, filed Jan. 13, 2014 (103 pages).
Suda, "The organ distribution and molecular forms of glucagon-related peptides," Yamagata Med J. 6(2):149-161 (1988) (English translation).
Table filed for European Application No. EP1877435B, on Jan. 14, 2014 (1 page).
Table of selected data from International Application No. 97/39031 filed by P during the oral proceedings of European Patent Application No. EP1877435B on Mar. 13, 2014 (1 page).
Tamaki et al., "Apoptosis in normal tissues induced by anti-cancer drugs," J Int Med Res. 31(1):6-16 (2003).
Tavares et al., "Enzymatic- and renal-dependent catabolism of the intestinotropic hormone glucagon-like peptide-2 in rats," Am J Physiol Endocrinol Metab. 278(1):E134-9 (2000).
Thulesen et al., "Glucagon-like peptide 2 (GLP-2) accelerates the growth of colonic neoplasms in mice," Gut. 53(8):1145-50 (2004).
Valverde et al., "Presence and characterization of glucagon-like peptide-1(7-36) amide receptors in solubilized membranes of rat adipose tissue," Endocrinology. 132(1):75-9 (1993).
Wells, "Additivity of mutational effects in proteins," Biochemistry. 29(37):8509-17 (1990).
Written Opinion of the International Searching Authority from PCT/GB2006/001633, dated Oct. 24, 2006 (9 pages).
Written Opinion of the International Searching Authority from PCT/GB2007/004273, dated Apr. 14, 2008 (8 pages).
Wøjdemann et al., "Inhibition of sham feeding-stimulated human gastric acid secretion by glucagon-like peptide-2," J Clin Endocrinol Metab. 84(7):2513-7 (1999).
Yazbeck et al., "Growth factor based therapies and intestinal disease: is glucagon-like peptide-2 the new way forward?," Cytokine Growth Factor Rev. 20(2):175-84 (2009).
Yusta et al., "Enteroendocrine localization of GLP-2 receptor expression in humans and rodents," Gastroenterology. 119(3):744-55 (2000).

(56) References Cited

OTHER PUBLICATIONS

Estall et al., "Dual Regulation of Cell Proliferation and Survival via Activation of Glucagon-Like Peptide-2 Receptor Signaling," J Nutr. 133(11):3708-11 (2003).

Lee et al., "Enteroendocrine-derived glucagon-like peptide-2 controls intestinal amino acid transport," Mol Metab. 6(3):245-255 (2017).

Ivory et al., "Interleukin-10-independent anti-inflammatory actions of glucagon-like peptide 2," Am J Physiol Gastrointest Liver Physiol. 295(6): G1202-10 (2008).

Torres et al., "Glucagon-like peptide-2 improves both acute and late experimental radiation enteritis in the rat," Int J Radiat Oncol Biol Phys. 69(5):1563-71 (2007).

A.

(OGTT n=10; +/- sem)

B.

GLUCAGON-LIKE-PEPTIDE-2 (GLP-2) ANALOGUES

FIELD OF THE INVENTION

The present invention relates to glucagon-like-peptide-2 (GLP-2) analogues with altered GLP-1 activity and their medical use, for example in the prophylaxis, treatment or ameliorating of diseases and conditions such as metabolic endotoxemia, diabetes, obesity, and the metabolic syndrome.

BACKGROUND OF THE INVENTION

Low-grade inflammation is an independent risk factor of heart disease, stroke, diabetes and mortality. Research findings suggest that atherosclerosis, which involves the formation of fatty deposits (plaques) and activity of free radicals and infectious agents in the arteries, can be likened to arthritis of the bones and joints because they are both inflammatory disorders. Inflammation precedes the detection of insulin resistance and therefore may be a good predictor of diabetes.

Further, it has been demonstrated that obese mice (ob/ob and db/db) have a disrupted mucosal barrier function and increased systemic inflammation (Brun et al., *Am J Physiol Gastrointest Liver Physiol* 292:G518-G525, 2007. 5 Oct. 2006). These observations were further extended to C57BL6/J mice maintained on high-fat-diet (Cani et al., DIABETES, VOL. 57, JUNE 2008, p 1470-1481) and nonobese diabetic mouse (Hadjiyanni et al., 2009). Cani and colleagues, gut.bmj.com, 2009) reported that in ob/ob mice, altering the gut microbiota reduced intestinal permeability and inflammation via a GLP-2 driven pathway. Further, the increased permeability observed in obese and diabetic patients is now is likely to have a more vital role in the disease progression than previously anticipated. Increased intestinal permeability leads to increased bacterial lipopolysaccharide (LPS) transport across the intestinal lumen. This increased LPS activates immune cells such as macrophages circulating and organ residing in the body causing low grade chronic inflammation involved in the pathogenesis of many diseases. This phenomenon is called metabolic endotoxemia (ME) and can be viewed as a novel concept in chronic disease pathology.

Targeting ME and associated diseases is within the scope of this invention. Diseases including type II diabetes mellitus, atherosclerosis, Parkinson's disease and cancer metastasis arise in the context of chronic low-grade inflammation, of which the source has not dearly been defined. Interestingly, several recent studies have demonstrated significant correlations between disease development and plasma endotoxin levels (Chang 2011, J Med Sci 2011; 31(5):191-209).

The hypothesized mechanism whereby a dual GLP2-GLP1 agonist will work in a obesity diabetes setting is depicted in FIG. 1. The GLP2 component reduces inflammation and metabolic endotoxemia whereas the GLP1 component provided glucose control and weight loss through classical GLP1 dependent mechanisms.

Human GLP-2 is a 33-amino-acid peptide derived from specific posttranslational processing of proglucagon in the enteroendocrine L cells of the intestine and in specific regions of the brainstem. It is co-secreted together with glucagon-like peptide 1 (GLP-1), oxyntomodulin, and glicentin, in response to nutrient ingestion.

GLP-2 induces significant growth of the small intestinal mucosal epithelium via the stimulation of stem cell proliferation in the crypts and inhibition of apoptosis in the villi (Drucker et al., Proc Nati Acad Sci USA 93:7911-7916 (1996)). GLP-2 also has growth effects on the colon. Furthermore, GLP-2 Inhibits gastric emptying and gastric acid secretion (Wojdemann et al., J Clin Endocrinol Metab. 84:2513-2517 (1999)), enhances intestinal barrier function (Benjamin et al., Gut47:112-9 (2000)), stimulates intestinal hexose transport via the upregulation of glucose transporters (Cheeseman, Am J Physiol. R1965-71 (1997)), and increases intestinal blood flow 29 (Guan et al., Gastroenterologyl 25:136147 (2003)).

GLP-2 binds to a single G protein-coupled receptor belonging to the class II glucagon secretin family. The GLP-2 receptor is expressed in the small intestine, colon and stomach, which also are sites that are known to be responsive to GLP-2 (Yusta et al., Gastroenterology 119:744-755 (2000)). However, the target cell type for GLP-2 receptor stimulation in the gastrointestinal tract remains unclear, and the downstream intracellular mediators coupled to the GLP-2 receptor are poorly understood.

The demonstrated specific and beneficial effects of GLP-2 in the small intestine have raised much interest as to the use of GLP-2 in the treatment of intestinal disease or injury (Sinclair and Drucker, Physiology 2005: 357-65). Furthermore GLP-2 has been shown to prevent or reduce mucosal epithelial damage in a wide number of preclinical models of gut injury, including chemotherapy-induced enteritis, ischemia-reperfusion injury, dextran sulfate-induced colitis and genetic models of inflammatory bowel disease (Sinclair and Drucker Physiology 2005: 357-65).

Additionally, the expression of the GLP-2R mRNA in the stomach, (Yusta et al., 2000) together with the observation that GLP-2 reduces gastric motility and gastric acid secretion (Meier et al., GASTROENTEROLOGY 2006; 130:44-54) provides ample evidence that the stomach is either directly or indirectly responsive to GLP-2. Nonetheless, the use of GLP-2 or analogues of GLP-2 in conditions characterised by damage to the gastric lining has not yet been explored.

GLP-2 is secreted as a 33 amino acid peptide with the following sequence His-Ala-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp (SEQ ID NO: 1) It is rapidly cleaved by the enzyme DPP IV at the alanine (Ala) at position 2 relative to the N-terminus to form an inactive human GLP-2 peptide (3-33). This rapid enzymatic degradation of GLP-2(1-33), in addition to renal clearance, results in a half life of about 7 minutes (Tavares et al., Am. J. Physiol. Endocrinol. Metab. 278:E134-E139 (2000)).

Representative GLP-2 analogues are described, e.g., in U.S. Pat. Nos. 5,789,379; 5,994,500; 6,184,201; 6,184,208; International Publication Nos. WO 97/39031; WO 01/41779; WO 02/066511 and DaCambra et al. (Biochemistry 2000, 39, 8888-8894). All references cited herein are expressly incorporated by reference in their entirety.

SUMMARY OF THE INVENTION

Broadly, the present invention concerns GLP-2 analogues comprising one or more substitutions in comparison to wild-type GLP-2 and which may have the property of an altered, preferably increased GLP-1 activity, e.g., as assessed in in vitro efficacy assays. GLP-1 activity, for example, can be measured by determining EC50 values at the GLP-1 receptor lower than for native GLP-2. In some embodiments, GLP-2 analogues of the invention comprise one or more substitutions at an amino acid position corresponding to one or more of positions 2, 3, 5, 7, 8, 9, 10, 11, 12, 14, 15, 16, 19, 20, 21, 24, 27 and/or 28 of the wild-type GLP-2 sequence in combination with Gln. Lys or Glu in position 17. In some embodiments, GLP-2 analogues of the invention comprise one or more substitutions at an amino acid position corresponding to one or more of positions 2, 3, 5, 7, 8, 9, 10, 11, 12, 15, 16, 20, 21, 24, 27 and/or 28 of the wild-type GLP-2 sequence in combination with Gln, Lys or Glu in position 17. In some embodiments, GLP-2 analogues of the invention comprise a conservative or non-conservative substitutions at position 2 and/or a substitution or deletion of one or more of amino acids corresponding to an amino acid of positions 28 to 33 of the wild-type GLP-2 sequence. In some embodiments, the GLP-2 analogues of the present invention optionally comprise lipophilic substituents conjugated to one or more of positions 12, 14, 16, 17, 19, 20, 24, 27, 28 and 32. In some embodiments, the GLP-2 analogues of the present invention optionally comprise lipophilic substituents conjugated to one or more of positions 12, 16, 17, 20, 24, 27, 28 and 32.

In some embodiments, a GLP-2 analogue is represented by the general Formula I:

(I)
(SEQ ID NO 2)
$R^1$-His-X2-X3-Gly-X5-Phe-X7-X8-X9-X10-X11-X12-X13-X14-X15-X16-X17-Ala-X19-X20-X21-Phe-Ile-X24-Trp-Leu-X27-X28-X29-X30-X31-X32-X33-$R^2$ or a pharmaceutically acceptable salt or solvate thereof, wherein:
$R^1$ is hydrogen, $C_{1-4}$ alkyl (e.g. methyl), acetyl, formyl, benzoyl or trifluoroacetyl;
X2 is Gly, Ala or Aib;
X3 is Glu, Gln or Asp;
X5 is Ser or Thr;
X7 is Ser or Thr;
X8 is Asp, Glu or Ser;
X9 is Glu or Asp;
X10 is Met, Val, Leu or Tyr;
X11 is Asn, Ser or Ala;
X12 is Thr, Ser or Lys;
X13 is Ile, Leu, Val, Tyr, Phe or Gln;
X14 is Leu or Met;
X15 is Asp or Glu;
X16 is Asn, Gln, Gly, Ser, Ala, Glu or Lys;
X17 is Gln, Lys, Arg, His or Glu;
X19 is Ala or Val;
X20 is Arg, Lys or His;
X21 is Asp, Glu or Leu;
X24 is Asn, Ala, Glu or Lys;
X27 is Ile, Leu, Val, Glu or Lys:
X28 is Gln, Asn, Lys, Ser, Y1 or absent;
X29 is Thr, Y1 or absent;
X30 is Lys, Y1 or absent;
X31 is Ile, Pro or absent;
X32 is Thr, Y1 or absent;
X33 is Asp, Asn, Y1 or absent;
Y1 is Gly-Gly-Pro-Ser-Ser-Gly-Ala-Pro-Pro-Pro-Ser, or Lys-Asn-Gly-Gly-Pro-Ser-Ser-Gly-Ala-Pro-Pro-Pro-Ser;
and
$R^2$ is $NH_2$ or OH;

with the proviso that the GLP-2 analogue of Formula I is not (SEQ ID NO 3)
HGDGSFSDEMNTILDGQAARDFINWLIQTKITD;

(SEQ ID NO 4)
HGDGSFSDEMNTILDNQAARDFINWLIQTKITD;
or (SEQ ID NO 5)
HGDGSFSDEMNTILDSQAARDFINWLIQTK

In this formula, X31 may also be Y1. X28 may also be Gly. X29 may also be Ala.
Additionally, Y1 may be present between X33 and $R^2$. Thus, a position X34 may be envisaged, where X34 is Y1 or is absent.

In some embodiments, a GLP-2 analogue is a GLP-2 analogue according to Formula I or a pharmaceutically acceptable salt or solvate thereof, wherein:
$R^1$ is hydrogen,
X2 is Gly, Ala or Aib;
X3 is Glu, Gln or Asp;
X5 is Ser or Thr;
X7 is Ser or Thr;
X8 is Asp, Glu or Ser;
X9 is Glu or Asp;
X10 is Met, Val, Leu or Tyr;
X11 is Asn, Ser, or Ala;
X12 is Thr or Lys;
X14 is Leu or Met;
X15 is Asp or Glu;
X16 is Asn, Gln, Gly, Ser, Ala, Glu or Lys;
X17 is Gln or Lys;
X19 is Ala or Val;
X20 is Arg, Lys or His;
X21 is Asp, Glu or Leu;
X24 is Asn, Ala, Glu or Lys;
X27 is Ile, Leu, Val or Lys:
X28 is Gln, Asn, Y1 or absent;
X29 is Thr, Y1 or absent;
X30 is Lys, Y1 or absent;
X31 is Ile, Pro, Y1 or absent;
X32 is Thr, Y1 or absent;
X33 is Asp, Asn, Y1 or absent;
Y1 is -Gly-Gly-Pro-Ser-Ser-Gly-Ala-Pro-Pro-Pro-Ser.
and
$R^2$ is $NH_2$ or OH;
with the proviso that the GLP-2 analogue of Formula I is not

HGDGSFSDEMNTILDGQAARDFINWLIQTKITD;

HGDGSFSDEMNTILDNQAARDFINWLIQTKITD;
or

HGDGSFSDEMNTILDSQAARDFINWLIQTK.

In this formula, X13 may be Ile, Leu, Val, Tyr, Phe or Gln. X28 may also be Gly. X29 may also be Ala. Y1 may be present between X33 and $R^2$.

In some embodiments X14 of Formula I is Leu.
In some embodiments X14 of Formula I is Met.
In some embodiments, X17 of Formula I is Gln.
In some embodiments, X17 of Formula I is Lys.
In some embodiments, X17 of Formula I is Glu.
In some embodiments X19 of Formula I is Ala.
In some embodiments X19 of Formula I is Val.
In some embodiments, X16 of Formula I is Gly and X17 of Formula I is Gln.

In some embodiments, X16 of Formula I is Gly and X17 of Formula I is Lys.

In some embodiments, X16 of Formula I is Gly and X17 is of Formula I is Glu.

In some embodiments, X2 of Formula I is Aib, X16 of Formula I is Gly and X17 of Formula I is Gln.

In some embodiments, X2 of Formula I is Aib, X16 of Formula I is Gly and X17 of Formula I is Lys.

In some embodiments, X2 of Formula I is Aib, X16 of Formula I is Gly and X17 of Formula I is Glu.

In some embodiments, X2 of Formula I is Gly, X16 of Formula I is Gly and X17 of Formula I is Gln.

In some embodiments, X2 of Formula I is Gly, X16 of Formula I is Gly and X17 of Formula a is Lys.

In some embodiments, X2 of Formula I is Gly, X16 of Formula I is Gly and X17 of Formula I is Glu.

In some embodiments, a GLP-2 analogue is represented by the general Formula Ia:

(Ia)
(SEQ ID NO 6)
$R^1$-His-X2-X3-Gly-X5-Phe-X7-X8-X9-X10-X11-X12-X13-Leu-X15-X16-X17-Ala-Ala-X20-X21-Phe-Ile-X24-Trp-Leu-X27-X28-X29-X30-X31-X32-X33-$R^2$ or a pharmaceutically acceptable salt or solvate thereof, wherein:
$R^1$ is hydrogen, $C_{1-4}$ alkyl (e.g. methyl), acetyl, formyl, benzoyl or trifluoroacetyl;
X2 is Gly, Ala or Aib;
X3 is Glu, Gln or Asp;
X5 is Ser or Thr;
X7 is Ser or Thr;
X8 is Asp, Glu or Ser;
X9 is Glu or Asp;
X10 is Met, Val, Leu or Tyr;
X11 is Asn or Ser;
X12 is Thr, Ser or Lys;
X13 is Ile, Leu, Val, Tyr, Phe or Gln;
X15 is Asp or Glu;
X16 is Asn, Gln, Gly, Ser, Ala, Glu or Lys;
X17 is Gln, Lys, Arg, His or Glu;
X20 is Arg, Lys or His;
X21 is Asp, Glu or Leu;
X24 is Asn, Ala, Glu or Lys;
X27 is Ile, Leu, Val, Glu or Lys:
X28 is Gln, Asn, Lys, Ser, Y1 or absent;
X29 is Thr, Y1 or absent;
X30 is Lys, Y1 or absent;
X31 is Ile, Pro or absent;
X32 is Thr, Y1 or absent;
X33 is Asp, Asn, Y1 or absent;
Y1 is Gly-Gly-Pro-Ser-Ser-Gly-Ala-Pro-Pro-Pro-Ser, or Lys-Asn-Gly-Gly-Pro-Ser-Ser-Gly-Ala-Pro-Pro-Pro-Ser and
$R^2$ is $NH_2$ or OH;
with the proviso that the GLP-2 analogue of Formula Ia is not

HGDGSFSDEMNTILDGQAARDFINWLIQTKITD;

HGDGSFSDEMNTILDNQAARDFINWLIQTKITD;
or

HGDGSFSDEMNTILDSQAARDFINWLIQTK.

In this formula, X31 may also be Y1.

Additionally, Y1 may be present between X33 and $R^2$. Thus, a position X34 may be envisaged, where X34 is Y1 or is absent.

X28 may also be Gly. X29 may also be Ala.

In some embodiments, a GLP-2 analogue is a GLP-2 analogue according to Formula Ia or a pharmaceutically acceptable salt or solvate thereof,
wherein:
$R^1$ is hydrogen,
X2 is Gly, Ala or Aib;
X3 is Glu, Gln or Asp;
X5 is Ser or Thr;
X7 is Ser or Thr;
X8 is Asp, Glu or Ser;
X9 is Glu or Asp;
X10 is Met, Val, Leu or Tyr;
X11 is Asn or Ser;
X12 is Thr or Lys;
X15 is Asp or Glu;
X16 is Asn, Gln, Gly, Ser, Ala, Glu or Lys;
X17 is Gln or Lys;
X20 is Arg, Lys or His;
X21 is Asp, Glu or Leu;
X24 is Asn, Ala, Glu or Lys;
X27 is Ile, Leu, Val or Lys:
X28 is Gln, Asn, Y1 or absent;
X29 is Thr, Y1 or absent;
X30 is Lys, Y1 or absent;
X31 is Ile, Pro, Y1 or absent;
X32 is Thr, Y1 or absent;
X33 is Asp, Asn, Y1 or absent;
Y1 is -Gly-Gly-Pro-Ser-Ser-Gly-Ala-Pro-Pro-Pro-Ser; and
$R^2$ is $NH_2$ or OH;
with the proviso that the analogue of Formula Ia is not

HGDGSFSDEMNTILDGQAARDFINWLIQTKITD;

HGDGSFSDEMNTILDNQAARDFINWLIQTKITD;
or

HGDGSFSDEMNTILDSQAARDFINWLIQTK.

In this formula, X13 may be Ile, Leu, Val, Tyr, Phe or Gln.
X28 may also be Gly, X29 may also be Ala.
Y1 may be present between X33 and $R^2$.
In some embodiments, X17 of Formula Ia is Gln.
In some embodiments, X17 of Formula Ia is Lys.
In some embodiments, X17 of Formula Ia is Glu.
In some embodiments, X16 of Formula Ia is Gly and X17 of Formula Ia is Gln.
In some embodiments, X16 of Formula Ia is Gly and X17 of Formula Ia is Lys.
In some embodiments, X16 of Formula Ia is Gly and X17 of Formula Ia is Glu.
In some embodiments, X2 of Formula Ia is Aib, X16 of Formula Ia is Gly and X17 of Formula Ia is Gln.
In some embodiments, X2 of Formula Ia is Aib, X16 of Formula Ia is Gly and X17 of Formula Ia is Lys.
In some embodiments, X2 of Formula Ia is Aib, X16 of Formula Ia is Gly and X17 of Formula Ia is Glu.
In some embodiments, X2 of Formula Ia is Gly, X16 of Formula Ia is Gly and X17 of Formula Ia is Gln.
In some embodiments, X2 of Formula Ia is Gly, X16 of Formula Ia is Gly and X17 of Formula Ia is Lys.

In some embodiments, X2 of Formula Ia is Gly, X16 of Formula Ia is Gly and X17 of Formula Ia is Glu.

In any one of the embodiments above, or independently, X8-X9-X10-X11 may be Ser-Glu-Leu-Ala.

In the generic formulae described above, positions X28 to X33 may be selected from certain amino acid residues, or may be Y1, or may be absent. It is intended that the GLP-2 analogue contains no more than one Y1 moiety, and that if present, Y1 forms the C-terminal part of the molecule. Thus, if any of positions is X28 to X33 is Y1, all downstream positions are absent; i.e. those positions X29 to X33 (or X34) downstream of that Y1 are absent). In this context, positions "downstream" of a given position are those located C-terminal of that position.

Further, if any of positions X28 to X33 is absent, then all positions downstream of that position are also absent (except that Y1 may be present). Thus, the only combinations of these positions which can be absent are X33; X32-X33; X31-X32-X33; X30-X31-X32-X33; X29-X30-X31-X32-X33; and X28-X29-X30-X31-X32-X33. To put it another way, if position XN is present (where N is an integer between 28 and 33) then position X(N−1) is also present.

The GLP-2 analogue may be represented by the general Formula II;

(II)
(SEQ ID NO 7)
R$^1$-His-X2-X3-Gly-X5-Phe-X7-Ser-Glu-Leu-Ala-X12-

X13-X14-X15-X16-X17-Ala-X19-X20-X21-Phe-Ile-X24-

Trp-Leu-X27-X28-X29-X30-X31-X32-X33-X34-R$^2$ or a pharmaceutically acceptable salt or solvate thereof, wherein:
R$^1$ is hydrogen, C$_{1-4}$ alkyl (e.g. methyl), acetyl, formyl, benzoyl or trifluoroacetyl;
X2 is Gly, Ala or Aib;
X3 is Glu, Gln or Asp;
X5 is Ser or Thr;
X7 is Ser or Thr;
X12 is Thr, Ser or Lys;
X13 is Ile, Leu, Val, Tyr, Phe or Gln;
X14 is Leu or Met;
X15 is Asp or Glu;
X16 is Gly, Ser, Ala, Glu or Lys;
X17 is Gln or Lys;
X19 is Ala or Val;
X20 is Arg, Lys or His;
X21 is Asp, Glu or Leu;
X24 is Asn, Ala, Glu or Lys;
X27 is Ile, Leu, Val, Glu or Lys:
X28 is Gln, Asn, Lys, Ser, Gly, Y1 or absent;
X29 is Thr, Ala, Y1 or absent;
X30 is Lys, Y1 or absent;
X31 is Ile, Pro, Y1 or absent;
X32 is Thr, Y1 or absent;
X33 is Asp, Asn, Y1 or absent;
X34 is Y1 or absent;
Y1 is Gly-Gly-Pro-Ser-Ser-Gly-Ala-Pro-Pro-Pro-Ser, or Lys-Asn-Gly-Gly-Pro-Ser-Ser-Gly-Ala-Pro-Pro-Pro-Ser and
R$^2$ is NH$_2$, or OH; wherein
the GLP-2 analogue contains no more than one Y1;
if any of X28 to X33 is Y1, those positions X29 to X34 downstream of that Y1 are absent;
if any of X28 to X33 is absent, those positions X29 to X33 downstream of that position are also absent.

In some embodiments, X16 of Formula II is Gly, Ser or Ala. In such embodiments, X17 of Formula II may be Lys, or X17 of Formula II may be Gln.

Further additionally or alternatively, X2 of Formula II may be Gly or Ala.

Thus, in some embodiments, X16 of Formula II is Gly and X17 of Formula II is Gln.

In some embodiments, X16 of Formula II is Gly and X17 of Formula II is Lys.

In some embodiments, X2 of Formula II is Gly, X16 of Formula II is Gly and X17 of Formula II is Gln.

In some embodiments, X2 of Formula II is Gly, X16 of Formula II is Gly and X17 of Formula II is Lys.

In some embodiments, X2 of Formula II is Aib, X16 of Formula II is Gly and X17 of Formula II is Gln.

In some embodiments, X2 of Formula II is Aib, X16 of Formula II is Gly and X17 of Formula II is Lys.

Thus, in some embodiments of Formula II:
R$^1$ is hydrogen, C$_{1-4}$ alkyl (e.g. methyl), acetyl, formyl, benzoyl or trifluoroacetyl;
X2 is Gly or Aib;
X3 is Glu or Asp;
X5 is Ser or Thr;
X7 is Ser or Thr;
X12 is Thr, Ser or Lys;
X13 is Ile, Leu, Val, Tyr, Phe or Gln;
X14 is Leu or Met;
X15 is Asp or Glu;
X16 is Gly, Ser or Ala;
X17 is Gln or Lys;
X19 is Ala or Val;
X20 is Arg, Lys or His;
X21 is Asp, Glu or Leu;
X24 is Asn, Ala, Glu or Lys;
X27 is Ile, Leu, Val, Glu or Lys:
X28 is Gln, Asn, Lys, Ser, Gly, Y1 or absent;
X29 is Thr, Ala, Y1 or absent;
X30 is Lys, Y1 or absent;
X31 is Ile, Pro, Y1 or absent;
X32 is Thr, Y1 or absent;
X33 is Asp, Asn, Y1 or absent;
X34 is Y1 or absent;
Y1 is Gly-Gly-Pro-Ser-Ser-Gly-Ala-Pro-Pro-Pro-Ser, or Lys-Asn-Gly-Gly-Pro-Ser-Ser-Gly-Ala-Pro-Pro-Pro-Ser; and
R$^2$ is NH$_2$ or OH; wherein
the GLP-2 analogue contains no more than one Y1;
if any of X28 to X33 is Y1, those positions X29 to X34 downstream of that Y1 are absent;
if any of X28 to X33 is absent, those positions X29 to X33 downstream of that position are also absent.

In some embodiments, X16 is Gly and X17 is Gln.
In some embodiments, X16 is Gly and X17 is Lys.
In some embodiments, X2 is Gly, X16 is Gly and X17 is Gln.
In some embodiments, X2 is Gly, X16 is Gly and X17 is Lys.
In some embodiments, X2 is Aib, X16 is Gly and X17 is Gln.
In some embodiments, X2 is Aib, X16 is Gly and X17 is Lys.
In some embodiments, a GLP-2 analogue is represented by the general Formula III:

(III)

(SEQ ID NO 21)
R¹-His-Gly-X3-Gly-X5-Phe-X7-Ser-Glu-Leu-Ala-X12-

X13-Leu-X15-Gly-X17-Ala-X19-X20-X21-Phe-Ile-X24-

Trp-Leu-X27-X28-X29-X30-X31-X32-X33-X34-R² or a pharmaceutically acceptable salt or solvate thereof, wherein:
R¹ is hydrogen, $C_{1-4}$ alkyl (e.g. methyl), acetyl, formyl, benzoyl or trifluoroacetyl;
X3 is Glu, or Asp;
X5 is Ser or Thr;
X7 is Ser or Thr;
X12 is Thr, Ser or Lys;
X13 is Ile, Tyr, or Gln;
X15 is Asp or Glu;
X17 is Gln or Lys;
X19 is Ala or Val;
X20 is Arg, Lys or His;
X21 is Asp, Glu or Leu;
X24 is Asn, Ala, Glu;
X27 is Ile, Leu, Glu or Lys:
X28 is Gln, Lys, Ser, Gly, Y1 or absent;
X29 is Thr, Ala, Y1 or absent;
X30 is Lys, Y1 or absent;
X31 is Ile, Pro, Y1 or absent;
X32 is Thr, Y1 or absent;
X33 is Asp, Asn, Y1 or absent;
X34 is Y1 or absent;
Y1 is Gly-Gly-Pro-Ser-Ser-Gly-Ala-Pro-Pro-Pro-Ser, or Lys-Asn-Gly-Gly-Pro-Ser-Ser-Gly-Ala-Pro-Pro-Pro-Ser and
R² is $NH_2$ or OH; wherein
the GLP-2 analogue contains no more than one Y1;
if any of X28 to X33 is Y1, those positions X29 to X34 downstream of that Y1 are absent;
if any of X28 to X33 is absent, those positions X29 to X33 downstream of that position are also absent.

In any of the above embodiments of the invention, it may be desirable that the amino acid sequence of the GLP-2 analogue has not more than 5 amino changes, e.g. not more than 4, not more than 3, not more than 2 or not more than 1 change from the amino acid sequence HGDGSFSSELATILDGKAARDFINWLIQTKITD or HGDGSFSSELATILDGQAARDFIAWLIQTKITD.

In some embodiments, a GLP-2 analogue of the invention is represented by any one of the following sequences:

```
                               (SEQ ID NO 8)
H-Aib-DGSFSDEMNTILDNQAARDFINWLIQTKITD;

(SEQ ID NO 9)
HGDGSFSDEMNTILDNKAARDFINWLIQTKITD;

(SEQ ID NO 10)
HGDGSFSDEMNTILDGQAARDFINWLIQTK;

(SEQ ID NO 11)
HGDGSFSSEMNTILDSQAARDFINWLIQTKITD;

(SEQ ID NO 12)
HGEGTFTSDLSKQMEGQAVRDFIEWLIQTKITD;

(SEQ ID NO 13)
HGEGTFTSDLSKQMESKAARDFIEWLIQTKITD;

(SEQ ID NO 14)
HGDGSFSSELATILDGKAARDFINWLIQTKITD;

(SEQ ID NO 15)
HGEGTFTSDLSTILENKAARDFIEWLIQTKITD;

(SEQ ID NO 16)
HGEGSFSSDLSTILENKAARDFIEWLIQTKITD;

(SEQ ID NO 17)
H-Aib-DGSFSDELNTILDGKAARDFINWLIQTK;

(SEQ ID NO 18)
HGDGSFSSELATILDGQAARDFIAWLIQTKITD;

(SEQ ID NO 19)
HGDGSFSDEMNTILDGQAARDFINWLIQTK;
and (SEQ ID NO 20)
HGEGSFSSDLSTILEGKAARDFIEWLIQTKITD;
``` or a pharmaceutically acceptable salt or solvate thereof.

Thus, the GLP-2 analogue of the invention may be a compound $R^1$—Z—$R^2$, wherein $R^1$ and $R^2$ are as defined in the generic formulae and Z is a peptide sequence selected from those listed above.

In some embodiments, a GLP-2 analogue of the invention comprises a lipophilic substituent conjugated to an amino acid at a position corresponding to one or more of positions 12, 14, 16, 17, 19, 20, 24, 27, 28 and 32 of native GLP-2.

In some embodiments, a GLP-2 analogue of the invention comprises a lipophilic substituent conjugated to an amino acid at a position corresponding to one or more of positions 12, 16, 17, 20, 24, 27, 28 and 32 of native GLP-2.

In some embodiments, a GLP-2 analogue of the invention may be used in a therapy.

In some embodiments, the invention provides a pharmaceutical composition comprising a GLP-2 analogue of the invention, or a salt or derivative thereof, in admixture with a carrier. In some embodiments, the pharmaceutical composition may comprise a GLP-2 analogue that is a pharmaceutically acceptable acid addition salt. In some embodiments, the pharmaceutical composition is formulated as a liquid suitable for administration by injection or infusion, or which is formulated to cause slow release of a GLP-2 analogue of the invention.

In some embodiments, the invention provides for the use of a GLP-2 analogue of the invention for the preparation of a medicament for the treatment and/or prevention of low grade inflammation.

In some embodiments, the invention provides for the use of a GLP-2 analogue of the invention for the preparation of a medicament for the treatment and/or prevention of low grade inflammation related to diabetes (which may be type I or type II diabetes, but particularly type II). In some embodiments, the low grade inflammation is local or systemic low grade inflammation. In some embodiments, the low grade inflammation includes the metabolic syndrome, obesity (e.g. abdominal obesity), diabetes, cardiovascular diseases, gastrointestinal inflammation, depression, Alzheimer, arthritis, hypertension, dyslipidaemia and stroke, gastro-intestinal disorders in the upper gastrointestinal tract of the oesophagus, the stomach, duodenum, the small intestine, colon and rectum including ulcers of any aetiology (e.g., peptic ulcers, Zollinger-Ellison Syndrome, drug-induced ulcers, ulcers related to infections or other pathogens), digestion disorders, malabsorption syndromes, short-bowel syndrome, cul-de-sac syndrome, inflammatory bowel disease (e.g., Crohns disease and ulcerative colitis), celiac sprue (for example arising from gluten induced enteropathy or celiac disease), tropical sprue, hypogammaglobulinemic sprue, and chemotherapy and/or radiationhemotherapy induced mucositis and diarrhea. Some of the above diseases, conditions and disorders may be characterized as being associated with low grade inflammation.

In some embodiments, the invention provides a nucleic acid molecule comprising a nucleic acid sequence encoding a GLP-2 analogue of the invention.

In some embodiments, the invention provides an expression vector comprising a nucleic acid molecule comprising a nucleic acid sequence encoding a GLP-2 analogue of the invention in combination with control sequences to direct the expression of the GLP-2 analogue. In some embodiments, the invention provides a host cell transformed with the expression vector.

In some embodiments, the invention provides a method of producing a GLP-2 analogue of the invention, the method comprising culturing host cells expressing the GLP-2 analogue under conditions suitable for expression and purifying the GLP-2 analogue thus produced.

In some embodiments, a nucleic acid molecule of the invention, an expression vector of the invention, or a host cell of the invention may be used in a therapy.

In some embodiments, the invention provides for the use of a nucleic acid molecule of the invention, an expression vector of the invention, or a host cell of the invention in the preparation of a medicament for the treatment and/or prevention of low grade inflammation. In some embodiments, the low grade inflammation is local or systemic, and can include, for example, metabolic syndrome (broadest definition), obesity (e.g. abdominal obesity), diabetes, cardiovascular diseases, gastrointestinal inflammation, depression, Alzheimer's disease, arthritis, hypertension, dyslipidaemia and stroke, gastro-intestinal disorders in the upper gastrointestinal tract of the oesophagus, the stomach, duodenum, the small intestine, colon and rectum including ulcers of any aetiology (e.g., peptic ulcers, Zollinger-Ellison Syndrome, drug-induced ulcers, ulcers related to infections or other pathogens), digestion disorders, malabsorption syndromes, short-bowel syndrome, cul-de-sac syndrome, inflammatory bowel disease (Crohns disease and ulcerative colitis), celiac sprue (for example arising from gluten induced enteropathy or celiac disease), tropical sprue, hypogammaglobulinemic sprue, and chemotherapy and/or radiationhemotherapy induced mucositis and diarrhea.

In some embodiments, the invention provides a method of treating a gastrointestinal-related disorder (e.g., stomach or bowel) in a patient in need thereof by administering an effective amount a GLP-2 analogue of the invention, a nucleic acid molecule of the invention, an expression vector of the invention, or a host cell of the invention. In some embodiments, the gastrointestinal related disorder is low grade inflammation. The low grad inflammation may be local or systemic, and may include the metabolic syndrome, obesity (e.g. abdominal obesity), diabetes, cardiovascular diseases, gastrointestinal inflammation, depression, alzheimer, arthritis, hypertension, dyslipidaemia and stroke, gastrointestinal disorders in the upper gastrointestinal tract of the oesophagus, the stomach, duodenum, the small intestine, colon, or rectum, including ulcers of any aetiology (e.g., peptic ulcers, Zollinger-Ellison Syndrome, drug-induced ulcers, ulcers related to infections or other pathogens), digestion disorders, malabsorption syndromes, short-bowel syndrome, cul-de-sac syndrome, inflammatory bowel disease (e.g., Crohns disease and ulcerative colitis), celiac sprue (for example arising from gluten induced enteropathy or celiac disease), tropical sprue, hypogammaglobulinemic sprue, and chemotherapy and/or radiationhemotherapy induced mucositis and diarrhea.

In some embodiments, the invention provides a therapeutic kit comprising a cancer chemotherapy drug and a GLP-2 analogue of the invention, a nucleic acid molecule of the invention, an expression vector of the invention or a host cell of the invention, each optionally in combination with a pharmaceutically acceptable carrier.

DETAILED DESCRIPTION OF THE INVENTION

Figure 1:
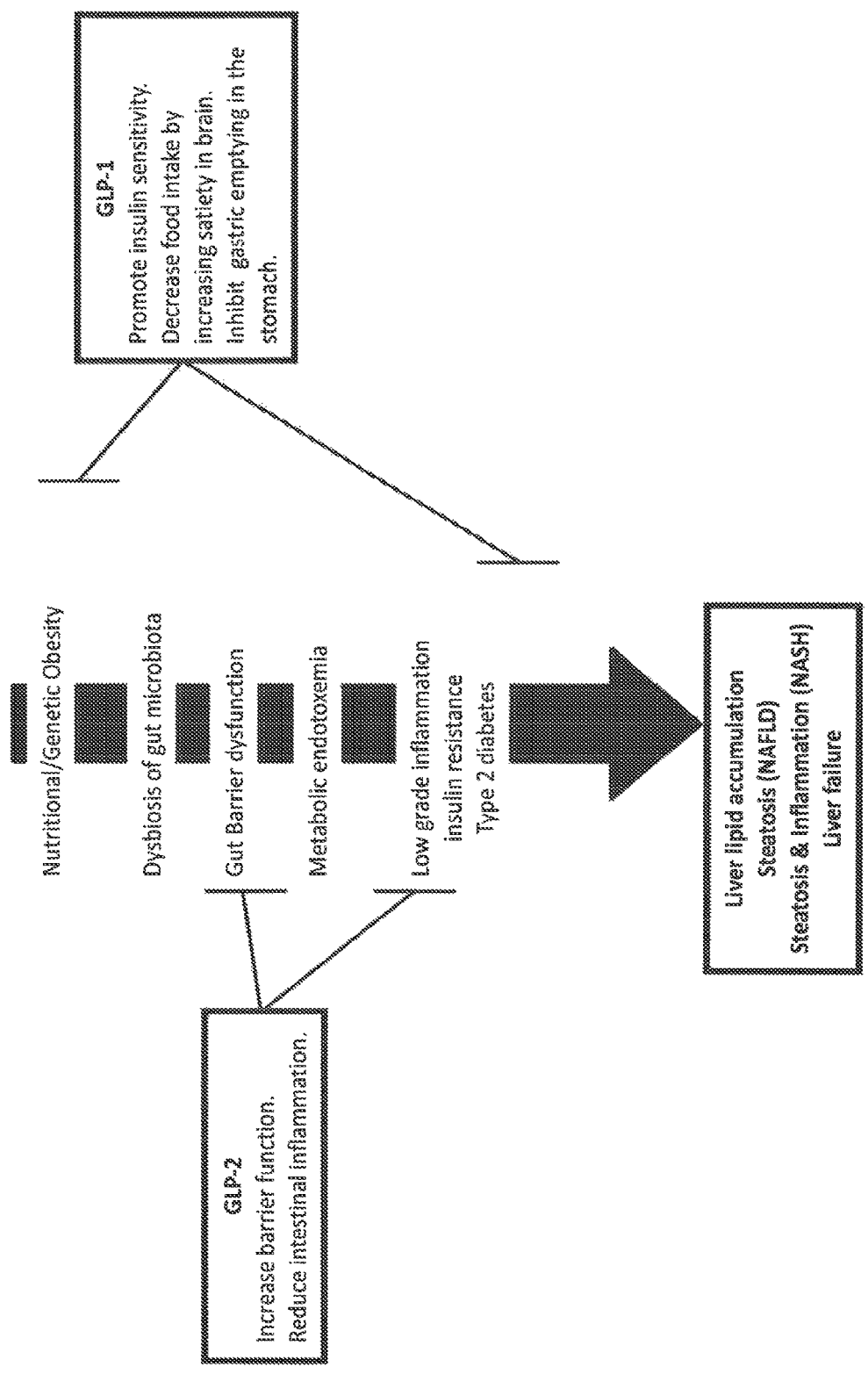
FIG. 1 shows the effects of GLP-1 and GLP-2 on physiological pathways. (Adapted from Cani et al., Pharmacology and Therapeutics 130 (2011) 202-212.)

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well known and commonly used in the art.

All publications, patents and published patent applications referred to in this application are specifically incorporated by reference herein. In case of conflict, the present specification, including its specific definitions, will control.

Each embodiment of the invention described herein may be taken alone or in combination with one or more other embodiments of the invention.

Definitions

Unless specified otherwise, the following definitions are provided for specific terms, which are used in the above written description.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context dearly dictates otherwise.

The term "including" is used to mean "including but not limited to." "Including" and "including but not limited to" are used interchangeably.

The terms "patient," "subject," and "individual" may be used interchangeably and refer to either a human or a non-human animal. These terms include mammals such as humans, primates, livestock animals (e.g., bovines, porcines), companion animals (e.g., canines, felines) and rodents (e.g., mice and rats).

The term "solvate" in the context of the present invention refers to a complex of defined stoichiometry formed between a solute (in casu, a peptide conjugate or pharmaceutically acceptable salt thereof according to the invention) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

The term "agonist" as employed in the context of the invention refers to a substance (ligand) that activates the receptor type in question.

Throughout the description and claims the conventional one-letter and three-letter codes for natural amino acids are used as well as generally accepted three letter codes for other α-amino acids, such as sarcosine (Sar), norleucine (Nle) and α-aminoisobutyric acid (Aib). All amino acid residues in peptides of the invention are preferably of the L-configuration. However, D-configuration amino acids may also be present.

Among sequences disclosed herein are sequences incorporating an "Hy-" moiety at the amino terminus (N-terminus) of the sequence, and either an "—OH" moiety or an "—NH$_2$" moiety at the carboxy terminus (C-terminus) of the sequence. In such cases, and unless otherwise indicated, an "Hy-" moiety at the N-terminus of the sequence in question indicates a hydrogen atom [e.g., R$^1$=Hy- in formulas I and Ia; corresponding to the presence of a free primary or secondary amino group at the N-terminus], while an "—OH" or an "—NH$_2$" moiety at the C-terminus of the sequence indicates a hydroxy group [e.g., R$^2$=OH in formulas I and Ia; corresponding to the presence of a carboxy (COOH) group at the C-terminus] or an amino group [e.g., R$^2$=NH$_2$ in formulas I and Ia; corresponding to the presence of an amido (CONH$_2$) group at the C-terminus], respectively. In each sequence of the invention, a C-terminal "—OH" moiety may be substituted for a C-terminal "—NH$_2$" moiety, and vice-versa.

As used herein a "conservative substitution" means that an amino acid residue belonging to a certain position of the native human GLP-2 peptide sequence has been exchanged with an amino acid residue belonging to the same group (I, II, III, IV, V, 1, 2, 3) as defined in the following table:

| I | II | III | IV | V |
|---|---|---|---|---|
| A | N | H | M | F |
| S | D | R | L | Y |
| T | E | K | I | W |
| P | Q |   | V |   |
| G |   |   | C |   |

| 1 | 2 | 3 |
|---|---|---|
| A | G | H |
| V | S | R |
| L | T | K |
| I | C | D |
| P | Y | E |
| F | N |   |
| W | Q |   |
| M |   |   |

A "non-conservative" substitution as used herein means any substitution other than a conservative substitution of an amino acid residue of the native human GLP-2 sequence, e.g., substitution with a non-protein non-natural amino acid (Sar, Nle, Aib) or substituting with an amino acid which does not belong to the same group.

In some embodiments of the invention, a compound of the invention has at least one GLP-2 and one GLP-1 biological activity. Exemplary activities include reducing the permeability of the intestine and altering inflammation in the intestine. This can be assessed in in vivo assays, for example as described in the examples, in which the mass and the permeability of the intestine, or a portion thereof, is determined after a test animal has been treated or exposed to a GLP-2 analogue.

In some embodiments, a GLP-2 analogue of the invention has at least 60% amino acid sequence identity to wild-type GLP-2 (1-33) having the sequence His-Ala-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp. For example, a GLP-2 analogue of the invention may have from between about 50% to 88% sequence identity, e.g., between about 60%-80% and in certain embodiments, at least 63%, 66%, or 69% sequence identity.

"Percent (%) amino acid sequence identity" with respect to the GLP-2 polypeptide sequences is defined as the percentage of amino acid residues in a candidate sequence that are identical to the amino acid residues in the wild-type GLP-2 sequence, after aligning the sequences and introducing gaps, if necessary, to achieve the maximum percent sequence identity, and not considering any conservative substitutions as part of the sequence identity. Sequence alignment can be carried out by the skilled person using techniques well known in the art for example using publicly available software such as BLAST, BLAST2 or Align software. For examples, see Altschul et al., Methods in Enzymology 266:460-480 (1996), Pearson et al., Genomics-46: 24-36, 1997, and the alignment program on the website at molbiol.soton.ac.uk/compute/align.

The percent sequence identities used herein and in accordance with the present invention may be determined using these programs with their default settings. More generally, the skilled worker can readily determine appropriate parameters for determining alignment, including any algorithms needed to achieve maximal alignment over the full length of the sequences being compared.

In some embodiments of the invention, a GLP-2 analogue of the invention comprises more than one substitution (i.e., more than one substitution relative to the wild type GLP-2 sequence given above) at positions X2, X3, X5, X7, X8, X9, X10, X11, X12, X13, X14, X15, X16, X17, X19, X20, X21, X24, X27, X28, X29, X30, X31, X32 and X33.

In some embodiments of the invention, a GLP-2 analogue of the invention comprises more than one substitution (i.e., more than one substitution relative to the wild type GLP-2 sequence given above) at positions X2, X3, X5, X7, X8, X9, X10, X11, X12, X13, X15, X16, X17, X20, X21, X24, X27, X28, X29, X30, X31, X32 and X33.

In some embodiments, the amino add residues in positions X28, X29, X30, X31, X32 and X33 are optionally deleted.

Without being bound by theory, we believe that a polar or charged residue (e.g., Gln, Lys or Glu) at a position corresponding to position 17 of a native GLP-2 peptide sequence, instead of Leu found in the native GLP-2 peptide sequence, may interact with and activate the GLP-1 receptor. A polar or charged amino acid in position 17, thus, may alter the receptor selectivity of GLP-2 peptides or analogues thereof, resulting in dual agonistic peptides activating both the GLP-1 and GLP-2 receptors.

Without being bound by theory, we believe that a small amino acid residue (e.g., Gly, Ser or Ala) at position 16 may be preferable for introducing or enhancing GLP-1 receptor activity of a GLP-2 peptide analogue. However, it may also be possible to obtain enhanced GLP-1 receptor activity with other amino acid substitutions as long as the amino acid in position 17 is polar or charged.

In some embodiments of the invention, a GLP-2 analogue as described above comprises a lipophilic substituent conjugated to one or more of positions 12, 14, 16, 17, 19, 20, 24, 27, 28 and 32.

In some embodiments of the invention, a GLP-2 analogue as described above comprises a lipophilic substituent conjugated to one or more of positions 12, 16, 17, 20, 24, 27, 28 and 32.

In a preferred embodiment of the present invention the GLP-2 analogue as described above comprises a lipophilic substituent conjugated to one or more of positions 16, 17, 20 and 24.

Exemplary compounds of the invention (derived from Formula I, Formula Ia or Formula II) are described below, wherein said compounds may be modified at the N-terminus and C-terminus as described for $R^1$ and $R^2$ and including a pharmaceutically acceptable salt or derivative thereof:

```
(Compound 1)
Hy-H-Aib-DGSFSDEMNTILDNQAARDFINWLIQTKITD-OH;

(Compound 2)
Hy-HGDGSFSDEMNTILDNKAARDFINWLIQTKITD-OH;

(Compound 3)
Hy-HGDGSFSDEMNTILDGQAARDFINWLIQTK-NH2;

(Compound 4)
Hy-HGDGSFSSEMNTILDSQAARDFINWLIQTKITD-OH;

(Compound 5)
Hy-HGEGTFTSDLSKQMEGQAVRDFIEWLIQTKITD-OH;

(Compound 6)
Hy-HGEGTFTSDLSKQMESKAARDFIEWLIQTKITD-OH:

(Compound 7)
Hy-HGDGSFSSELATILDGKAARDFINWLIQTKITD-OH;

(Compound 8)
Hy-HGEGTFTSDLSTILENKAARDFIEWLIQTKITD-OH;

(Compound 9)
Hy-HGEGSFSSDLSTILENKAARDFIEWLIQTKITD-OH;

(Compound 10)
Hy-H-Aib-DGSFSDELNTILDGKAARDFINWLIQTK-NH2;

(Compound 11)
Hy-HGDGSFSSELATILDGQAARDFIAWLIQTKITD-OH;

(Compound 12)
Hy-HGDGSFSDEMNTILDGQAARDFINWLIQTK-NH2;

(Compound 13)
Hy-HGEGSFSSDLSTILEGKAARDFIEWLIQTKITD-OH.
```

In some embodiments, the present invention provides the use of GLP-2 analogues of the invention for the preparation of a medicament for the treatment and/or prevention of gastrointestinal inflammation, e.g., low level gastrointestinal inflammation related to diabetes.

In some embodiments, the present invention provides a nucleic acid molecule comprising a nucleic acid sequence encoding a GLP-2 analogue as defined herein.

In further aspects, the present invention provides an expression vector comprising the above nucleic acid sequence, optionally in combination with sequences to direct its expression, and host cells transformed with the expression vectors. Preferably the host cells are capable of expressing and secreting the GLP-2 analogue. In a still further aspect, the present invention provides a method of producing the GLP-2 analogue, the method comprising culturing the host cells under conditions suitable for expressing the GLP-2 analogue and purifying the GLP-2 analogue thus produced.

The invention further provides a nucleic acid of the invention, an expression vector of the invention, or a host cell capable of expressing and secreting a GLP-2 analogue of the invention, for use in therapy. It will be understood that the nucleic acid, expression vector and host cells may be used for treatment of any of the disorders described herein which may be treated with the GLP-2 analogues themselves. References to a therapeutic composition comprising a GLP-2 analogue of the invention, or administration of a GLP-2 analogue of the invention, should therefore be construed to encompass administration of a nucleic acid, expression vector or host cell of the invention except where the context demands otherwise.

In some embodiments, the present invention provides the use of a nucleic acid molecule, an expression vector, or a host cell as defined herein, in the preparation of a medicament for the treatment and/or prevention of gastrointestinal inflammation.

In some embodiments, the present invention provides a method of treating a low level gastrointestinal inflammation related to diabetes In some embodiments, the present invention provides a method of treating or preventing low level gastrointestinal inflammation related to diabetes in a patient in need thereof, the method comprising administering an effective amount a nucleic acid, expression vector or host cell of the invention.

As described above, the GLP-2 analogues of the invention have one or more amino acid substitutions, deletions, inversions, or additions compared to native GLP-2. This definition also includes the synonym terms GLP-2 mimetics and/or GLP-2 agonists. Further, an analogue of the present invention may additionally have a chemical modification of one or more of its amino acid side groups, α-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine ε-amino groups, N-alkylation of arginine, histidine, or lysine, alkylation of glutamic or aspartic carboxylic acid groups, and deamidation of glutamine or asparagine. Modifications of the N-terminal amino group includes, without limitation, des-amino, N-lower alkyl, N-di-lower alkyl, and N-acyl modifications. Modifications of the C-terminal carboxy group include, without limitation, amide, lower alkyl amide, dialkyl amide, and lower alkyl ester modifications. Preferably, a lower alkyl is $C_1$-$C_4$ alkyl. Furthermore, one or more functional groups in side chains or terminal groups, may be protected by protective groups known to the skilled worker. In some embodiments, the alpha-carbon or an amino acid may be mono- or di-methylated.

When present, an oxidatively stable Met-replacement amino acid means one which is selected among the group consisting of Met(O) (methionine sulfoxide), Met(O)$_2$ (methionine sulfone), Val, Ile, Ser and preferably Ile, Leu, Val, Lys or Ser.

Lipophilic Substituents

One or more of the amino acid side chains in a compound employed in the context of the invention may be conjugated to a lipophilic substituent $Z^1$. Without wishing to be bound by theory, we believe that a lipophilic substituent binds albumin in the blood stream, thus shielding the compounds employed in the context of the invention from enzymatic degradation, which can enhance the half-life of the compounds. The lipophilic substituent may also modulate the potency of the compound, e.g., with respect to the GLP-2 receptor and/or the GLP-1 receptor.

In certain embodiments, only one amino acid side chain is conjugated to a lipophilic substituent. In other embodiments, two amino acid side chains are each conjugated to a lipophilic substituent. In yet further embodiments, three or even more amino acid side chains are each conjugated to a lipophilic substituent. When a compound contains two or more lipophilic substituents, they may be the same or different substituents.

The lipophilic substituent $Z^1$ may be covalently bonded to an atom in the amino acid side chain, or alternatively may be conjugated to the amino acid side chain by one or more spacers $Z^2$.

The term "conjugated" is used here to describe the covalent attachment of one identifiable chemical moiety to another, and the structural relationship between such moieties. It should not be taken to imply any particular method of synthesis. The one or more spacers $Z^2$, when present, are used to provide a spacing between the compound and the lipophilic moiety.

A lipophilic substituent may be attached to an amino acid side chain or to a spacer via an ester, a sulphonyl ester, a thioester, an amide or a sulphonamide. Accordingly, it will be understood that a lipophilic substituent may include an acyl group, a sulphonyl group, an N atom, an O atom or an S atom which forms part of the ester, sulphonyl ester, thioester, amide or sulphonamide. Preferably, an acyl group in the lipophilic substituent forms part of an amide or ester with the amino acid side chain or the spacer. The lipophilic substituent may include a hydrocarbon chain having 10 to 24 carbon (C) atoms, e.g. 10 to 22 C atoms, e.g. 10 to 20 C atoms. Preferably, it has at least 11 C atoms, and preferably it has 18 C atoms or fewer. For example, the hydrocarbon chain may contain 12, 13, 14, 15, 16, 17 or 18 carbon atoms. The hydrocarbon chain may be linear or branched and may be saturated or unsaturated. From the discussion above, it will be understood that the hydrocarbon chain is preferably substituted with a moiety which forms part of the attachment to the amino acid side chain or the spacer, for example an acyl group, a sulphonyl group, an N atom, an O atom or an S atom. Most preferably, the hydrocarbon chain is substituted with an acyl group, and accordingly the hydrocarbon chain may be part of an alkanoyl group, for example a dodecanoyl, 2-butyloctanoyl, tetradecanoyl, hexadecanoyl, heptadecanoyl, octadecanoyl or eicosanoyl group.

As mentioned above, the lipophilic substituent $Z^1$ may be conjugated to the amino acid side chain by one or more spacers $Z^2$. When present, the spacer is attached to the lipophilic substituent and to the amino acid side chain. The spacer may be attached to the lipophilic substituent and to the amino acid side chain independently by an ester, a sulphonyl ester, a thioester, an amide or a sulphonamide. Accordingly, it may include two moieties independently selected from acyl, sulphonyl, an N atom, an O atom or an S atom. The spacer may consist of a linear $C_{1-10}$ hydrocarbon chain or more preferably a linear $C_{1-5}$ hydrocarbon chain. Furthermore the spacer can be substituted with one or more substituents selected from $C_{1-6}$ alkyl, $C_{1-6}$ alkyl amine, $C_{1-6}$ alkyl hydroxy and $C_{1-6}$ alkyl carboxy.

The spacer may be, for example, a residue of any naturally occurring or unnatural amino acid. For example, the spacer may be a residue of Gly, Pro, Ala, Val, Leu, Ile, Met, Cys, Phe, Tyr, Trp, His, Lys, Arg, Gln, Asn, α-Glu, γ-Glu, ε-Lys, Asp, Ser, Thr, Gaba, Aib, β-Ala (i.e., 3-aminopropanoyl), 4-aminobutanoyl, 5-aminopentanoyl, 6-aminohexanoyl, 7-aminoheptanoyl, 8-aminooctanoyl, 9-aminononanoyl, 10-aminodecanoyl or 8-amino-3,6-dioxaoctanoyl. In certain embodiments, the spacer is a residue of Glu, γ-Glu, ε-Lys, β-Ala (i.e., 3-aminopropanoyl), 4-aminobutanoyl, 8-aminooctanoyl or 8-amino-3,6-dioxaoctanoyl. In the present invention, γ-Glu and isoGlu are used interchangeably. The amino acid side chain to which the lipophilic substituent is conjugated may be a side chain of a Glu, Lys, Ser, Cys, Dbu, Dpr or Orn residue. For example, it may be a side chain of a Lys, Glu or Cys residue. Where two or more side chains carry a lipophilic substituent, they may be independently selected from those residues. Thus, the amino acid side chain includes an carboxy, hydroxyl, thiol, amide or amine group, for forming an ester, a sulphonyl ester, a thioester, an amide, or a sulphonamide with the spacer or lipophilic substituent.

An example of a lipophilic substituent comprising a lipophilic moiety $Z^1$ and spacer $Z^2$ is shown in the formula below:

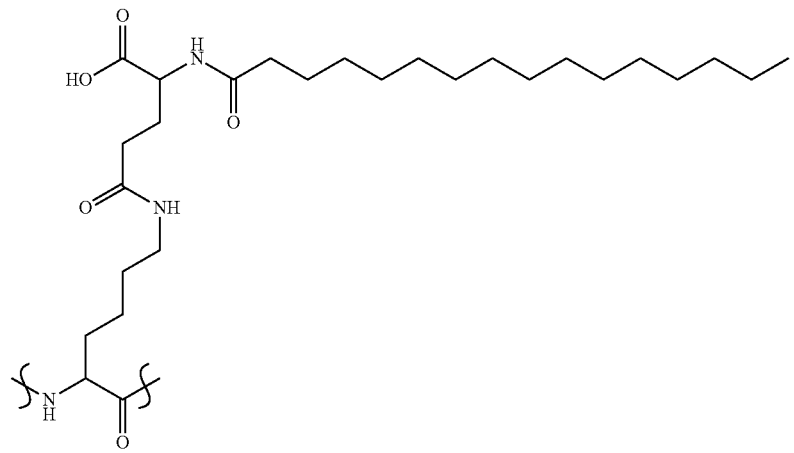 [SMILES: CCCCCCCCCCCCCCCC(=O)NC(CCC(=O)NCCCCC(NC)C(C)=O)C(=O)O]

Here, the side chain of a Lys residue is covalently attached to a γ-Glu spacer ($Z^2$) via an amide linkage. A hexadecanoyl group (Z') is covalently attached to the γ-Glu spacer via an amide linkage. This combination of lipophilic moiety and spacer, conjugated to a Lys residue, may be referred to by the short-hand notation K(Hexadecanoyl-γ-Glu), e.g., when shown in formulae of specific compounds. γ-Glu can also be referred to as isoGlu, and a hexadecanoyl group as a palmitoyl group. Thus it will be apparent that the notation (Hexadecanoyl-γ-Glu) is equivalent to the notations (isoGlu (Palm)) or (isoGlu(Palmitoyl)) as used for example in PCT/GB2008/004121.

The skilled person will be well aware of suitable techniques for preparing the compounds employed in the context of the invention. For examples of suitable chemistry, see WO98/08871, WO00/55184, WO00/55119, Madsen et al., J. Med. Chem. 50:6126-32 (2007), and Knudsen et al., J. Med Chem. 43:1664-1669 (2000), incorporated herein by reference.

In some embodiments, a GLP2-analogue of the invention has a lipophilic substituent as described above conjugated to an amino acid at one or more of positions corresponding to positions 12, 14, 16, 17, 19, 20, 24, 27, 28 and 32 of native GLP-2.

In some embodiments, a GLP2-analogue of the invention has a lipophilic substituent as described above conjugated to an amino acid at one or more of positions corresponding to positions 12, 16, 17, 20, 24, 27, 28 and 32 of native GLP-2.

It should be understood that the peptides of the invention might also be provided in the form of a salt or other derivative. Salts include pharmaceutically acceptable salts such as acid addition salts and basic salts. Examples of acid addition salts include hydrochloride salts, citrate salts, lactate salts, malate salts and acetate salts. Examples of basic salts include salts where the cation is selected from alkali metals, such as sodium and potassium, alkaline earth metals, such as calcium, and ammonium ions $^+N(R^3)_3(R^4)$, where $R^3$ and $R^4$ independently designates optionally substituted $C_{1-6}$-alkyl, optionally substituted $C_{2-6}$-alkenyl, optionally substituted aryl, or optionally substituted heteroaryl. Other examples of pharmaceutically acceptable salts are described in "Remington's Pharmaceutical Sciences", 17$^{th}$ edition. Ed. Alfonso R. Gennaro (Ed.), Mark Publishing Company, Easton, Pa., U.S.A., 1985 and more recent editions, and in the Encyclopaedia of Pharmaceutical Technology.

Other derivatives of the GLP-2 analogues of the invention include coordination complexes with metal ions such as $Mn^{2+}$ and $Zn^{2+}$, esters such as in vivo hydrolysable esters, free acids or bases, hydrates, prodrugs or lipids. Esters can be formed between hydroxyl or carboxylic acid groups present in the compound and an appropriate carboxylic acid or alcohol reaction partner, using techniques well known in the art. Derivatives which are prodrugs of the compounds are convertible in vivo or in vitro into one of the parent compounds. Typically, at least one of the biological activities of compound will be reduced in the prodrug form of the compound, and can be activated by conversion of the prodrug to release the compound or a metabolite of it. Examples of prodrugs include the use of protecting groups which may be removed in situ releasing active compound or serve to inhibit clearance of the drug in vivo.

GLP-2 analogues having an EC50 value of 1 nM or below, and preferably below 1 nM, are defined as GLP-2 agonists.

The present invention includes the following peptides further described in the experiments below.

Synthesis of GLP-2 Analogues

It is preferred to synthesize the analogues of the invention by means of solid phase or liquid phase peptide synthesis. In this context, the skilled worker may look to PCT publication WO 98/11125 and Fields, G B et al., 2002, "Principles and practice of solid-phase peptide synthesis" in: Synthetic Peptides (2$^{nd}$ Edition) (incorporated herein by reference) and to the Examples herein.

Thus, the GLP-2 analogues may be synthesized in a number of ways including, for example, a method comprising:

(a) synthesizing the peptide by means of solid phase or liquid phase peptide synthesis and recovering the synthetic peptide thus obtained;

(b) when the peptide consists of naturally occurring amino acids, expressing a nucleic acid construct that encodes the peptide in a host cell and recovering the expression product from the host cell culture;

(c) when the peptide consists of naturally occurring amino acids, effecting cell-free in vitro expression of a nucleic acid construct that encodes the peptide and recovering the expression product; or a combination of methods of (a), (b), and (c) to obtain fragments of the peptide, subsequently joining (e.g., ligating) the fragments to obtain the peptide, and recovering the peptide.

Thus, for some analogues of the invention it may be advantageous to exploit genetic engineering techniques. This may be the case when the peptide is sufficiently large (or produced as a fusion construct) and when the peptide only includes naturally occurring amino acids that can be translated from RNA in living organisms.

For the purposes of recombinant gene technology, nucleic acid fragments encoding the peptides of the invention are important chemical products. Hence, a further aspect of the present invention provides a nucleic acid molecule comprising a nucleic acid sequence encoding a GLP-2 analogue of the invention, where the peptide preferably is comprised of naturally occurring amino acids. The nucleic acid fragments of the invention may be either DNA or RNA fragments.

The nucleic acid fragments of the invention will normally be inserted in suitable vectors to form cloning or expression vectors carrying the nucleic acid fragments of the invention. Such novel vectors are also part of the invention. Details concerning the construction of these vectors of the invention will be discussed in context of transformed cells and microorganisms below. The vectors can, depending on purpose and type of application, be in the form of plasmids, phages, cosmids, mini-chromosomes, or viruses, but naked DNA which is only expressed transiently in certain cells also is an important vector. Preferred cloning and expression vectors (plasmid vectors) of the invention are capable of autonomous replication, thereby enabling high copy-numbers for the purposes of high-level expression or high-level replication for subsequent cloning.

The general outline of a vector of the invention comprises the following features in the 5' to 3' direction and in operable linkage: a promoter for driving expression of the nucleic acid fragment of the invention, optionally a nucleic acid sequence encoding a leader peptide enabling secretion (to the extracellular phase or, where applicable, into the periplasma) of or a leader peptide for multiple use e.g. combined secretion, purification tag and enzymatic trimming to correct peptide or integration into the membrane of the polypeptide fragment, the nucleic acid fragment encoding the peptide of the invention, and optionally a nucleic acid sequence encoding a terminator. When operating with expression vectors in producer strains or cell lines, it is for the purposes of genetic stability of the transformed cell preferred that the vector when introduced into a host cell is integrated in the host cell genome.

The vectors of the invention may be used to transform host cells to produce a GLP-2 analogue of the invention. Such transformed cells, which are also part of the invention, can be cultured cells or cell lines used for propagation of the nucleic acid fragments and vectors of the invention, or used for recombinant production of the peptides of the invention.

Preferred transformed cells of the invention are microorganisms such as bacteria including, for example, bacteria from the genera *Escherichia* (e.g., *E. coli*), *Bacillus* (e.g., *Bacillus subtilis*), *Salmonella*, or *Mycobacterium* (preferably non-pathogenic, e.g., *M. bovis* BCG)), yeasts (such as *Saccharomyces cerevisiae*), and protozoans. Alternatively, the transformed cells may be derived from a multicellular organism, e.g., fungal cells, insect cells, plant cells, or mammalian cells (e.g., cells derived from a human). For the purposes of cloning and/or optimised expression, it is preferred that the transformed cell is capable of replicating a nucleic acid fragment of the invention. Cells expressing a nucleic fragment of the invention are preferred useful embodiments of the invention. They can be used for small-scale or large-scale preparation of the peptides of the invention.

When producing a peptide of the invention by means of transformed cells, it is convenient, although not essential, for cells to either export the expression product into the culture medium or carry the expression product on the surface of the transformed cell.

When an effective producer cell has been identified it is preferred, on the basis thereof, to establish a stable cell line which carries the vector of the invention and which expresses the nucleic acid fragment encoding the peptide. Preferably, this stable cell line secretes or carries the peptide of the invention, thereby facilitating purification thereof.

In general, plasmid vectors containing replicon and control sequences, which are derived from species compatible with the host cell, are used in connection with a host. The vector ordinarily carries a replication site, as well as marking sequences, which are capable of providing phenotypic selection in transformed cells. For example, *E. coli* may typically be transformed using pBR322 (although numerous other useful plasmids exist), a plasmid derived from an *E. coli* species (see, e.g., Bolivar et al., 1977). The pBR322 plasmid contains genes for ampicillin and tetracycline resistance and, thus, provides easy means for identifying transformed cells. The pBR plasmid, or other microbial plasmid or phage must also contain, or be modified to contain, promoters, which can be used by the prokaryotic microorganism for expression.

Those promoters most commonly used in prokaryotic recombinant DNA construction include the beta-lactamase (penicillinase) and lactose promoter systems (Chang et al., 1978; Itakura et al., 1977; Goeddel et al., 1979) and a tryptophan (trp) promoter system (Goeddel et al., 1979; EP 0 036 776 A). While these are the most commonly used, other microbial promoters have been discovered and utilized, and details concerning their nucleotide sequences have been published, enabling a skilled worker to ligate them functionally with plasmid vectors (Siebwenlist et al., 1980).

In addition to prokaryotes, eukaryotic microbes, such as yeast cultures may also be used. In these embodiments, a promoter also should be capable of driving expression. *Saccharomyces cerevisiae*, or common baker's yeast, is the most commonly used among eukaryotic microorganisms, although a number of other strains are commonly available. For example, *Pichia stiptis* and *Schizosaccharomyces pombe* also may be used. For expression in *Saccharomyces*, the plasmid YRp7, for example, is commonly used (Stinchcomb et al., 1979; Kingsman et al., 1979; Tschemper et al., 1980). This plasmid already contains the trpl gene which provides a selection marker for a mutant strain of yeast lacking the ability to grow in tryptophan (for example ATCC No. 44076 or PEP4-1) (Jones, 1977. The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other promoters, which have the additional advantage of transcription controlled by growth conditions, are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate in culture (tissue culture) has become a routine procedure in recent years (Tissue Culture, 1973). Examples of such useful host cell lines are VERO and HeLa cells, Chinese hamster ovary (CHO) cell lines, and W138, BHK, COS-7 293, *Spodoptera frugiperda* (SF) cells (commercially available as complete expression systems from i.a. Protein Sciences, 1000 Research Parkway, Meriden, Conn. 06450, U.S.A. and from Invitrogen), the *D. melanogaster* cell line $S_2$ available from Invitrogen, PO Box 2312, 9704 CH Groningen. The Netherlands, and MDCK cell lines.

Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment, which also contains the SV40 viral origin of replication (Fiers et al., 1978). Smaller or larger SV40 fragments may also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or another virus (e.g., Polyoma, Adenovirus, VSV, and BPV), or it may be provided by the host cell chromosomal replication mechanism. If the vector is integrated into the host cell chromosome, the latter is often sufficient.

In order to obtain satisfactory yields in a recombinant production process, it may be advantageous to prepare the analogues as fusion proteins, either by fusing the peptide to a fusion partner that can serve as an affinity tag (for ease of purification) and/or by having multiple repeats of the peptide. These methods require presence of a suitable cleavage site for a peptidase. The skilled worker will know how to tailor the underlying genetic constructs.

After recombinant preparation, the peptides of the invention can be purified by methods generally known in the art, including multi-step chromatography (e.g., ion-exchange, size-exclusion, and affinity chromatographic techniques).

Alternatively, peptides comprised of naturally occurring amino acids can be prepared in vitro in cell free systems. This is especially expedient in cases where the peptides could be toxic for putative host cells. Thus, the present invention also contemplates use of cell-free in vitro translation/expression in order to prepare the peptides of the invention. In this context, reference is made to commercially available in vitro translation kits, materials, and technical documentation from e.g. Ambion Inc., 2130 Woodward, Austin, Tex. 78744-1832, USA.

Finally, the available methods can of course be combined to prepare e.g., semi-synthetic analogues. In such a set up, peptide fragments are prepared using at least 2 separate steps or methods, followed by joining (e.g., ligating) the fragments to obtain the final peptide product.

Biological Activity

Typically the GLP-2 analogues of the invention have activity at both the GLP-1 and GLP-2 receptors.

$EC_{50}$ values may be used as a numerical measure of agonist potency at a given receptor. An EC value is a measure of the concentration of a compound required to achieve half of that compound's maximal activity in a particular assay. A compound having an $EC_{50}$ at a particular receptor which is lower than the $EC_{50}$ of a reference compound in the same assay may be considered to have higher potency at that receptor than the reference compound.

The GLP-2 analogues of the invention typically have higher activity at the GLP-1 receptor (e.g. the human GLP-1 receptor) than wild type human GLP-2 (hGLP-2). Thus, in any given assay for GLP-1 activity, the GLP-2 analogues will have a lower $EC_{50}$ than wild type human GLP-2 or [Gly2]-hGLP-2 (i.e. human GLP-2 having glycine at position 2, also known as teduglutide). When assessed in the same GLP-1 activity assay, the ratio of the GLP-2 analogue's $EC_{50}$ to the $EC_{50}$ of hGLP-2 or [Gly2]-hGLP-2 is therefore typically less than 1. It may, for example, be less than 0.5 or less than 0.1, or less than 0.01.

The $EC_{50}$ at the GLP-1 receptor may be below 100 nM, below 50 nM, below 10 nM, or more preferably below 1.0 nM, below 0.9 nM, below 0.8 nM, below 0.7 nM, below 0.6 nM, below 0.5 nM, below 0.4 nM, below 0.3 nM, below 0.2 nM, below 0.1 nM, below 0.09 nM, below 0.08 nM, below 0.07 nM, below 0.06 nM, below 0.05 nM, below 0.04 nM, below 0.03 nM, below 0.02 nM, below 0.01 nM, below 0.009 nM, below 0.008 nM, below 0.007 nM, below 0.006 nM, or below 0.005 nM, e.g. when assessed using the GLP-1 receptor efficacy assay described in Example 1.

The GLP-2 analogues of the invention retain GLP-2 activity, although their potency at the GLP-2 receptor need not be the same as that of hGLP-2 or [Gly2]-hGLP-2. They may have lower potency as long as adequate levels of GLP-2 activity are retained. In any given assay for GLP-2 activity, the GLP-2 analogues may have a lower or higher $EC_{50}$ than wild type human GLP-2 or [Gly2]-hGLP-2. When assessed in the same GLP-2 activity assay, the ratio of the GLP-2 analogue's $EC_{50}$ to the $EC_{50}$ of hGLP-2 or [Gly2]-hGLP-2 in the same assay may, for example, be less than 200, less than 100, less than 10, less than 5, less than 1, less than 0.1, less than 0.5 or less than 0.1.

It may also be desirable to compare the ratio of $EC_{50}$ values at the GLP-2 and GLP-1 receptors for the analogue of the invention and for hGLP-2 or [Gly2]-hGLP-2. Preferably, for any given pair of GLP-2 and GLP-1 assays, the analogue of the invention has an $EC_{50}$[GLP-2]/$EC_{50}$[GLP-1] which is higher than the equivalent ratio for hGLP-2 or [Gly2]-hGLP-2 in the same assays, for example, the ratio for the analogue of the invention may be at least 2, at least 5 or at least 10 times greater than that for hGLP-2 or [Gly2]-hGLP-2.

Pharmaceutical Compositions and Administration

The GLP-2 analogues of the present invention, or salts or derivatives thereof, may be formulated as pharmaceutical compositions prepared for storage or administration, and which comprise a therapeutically effective amount of a GLP-2 peptide of the present invention, or a salt or derivative thereof, in a pharmaceutically acceptable carrier.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy so as to deliver the peptide to the large intestine, but will depend on such factors as weight, diet, concurrent medication and other factors, well known those skilled in the medical arts.

It is within the invention to provide a pharmaceutical composition, wherein a GLP-2 analogue of the invention, or a salt thereof, is present in an amount effective to treat or prevent stomach and bowel-related disorders.

Pharmaceutically acceptable salts of the compounds of the invention having an acidic moiety can be formed using organic and inorganic bases. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di- or trihydroxy lower alkylamine (e.g., mono-, di- or triethanolamine). Internal salts also may be formed. Similarly, when a compound of the present invention contains a basic moiety, salts can be formed using organic and inorganic acids. For example, salts can be formed from the following acids: acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, and camphorsulfonic as well as other known pharmaceutically acceptable acids.

Amino acid addition salts can also be formed with amino acids such as lysine, glycine, and phenylalanine.

As is apparent to one skilled in the art, a "therapeutically effective amount" of the peptides or pharmaceutical compositions of the present invention will vary depending upon the age, weight and mammalian species treated, the particular compounds employed, the particular mode of administration and the desired effects and the therapeutic indication. Because these factors and their relationship to determining this amount are well known, the determination of therapeutically effective dosage levels, the amount necessary to achieve the desired result of preventing and/or treating the intestine and stomach related diseases described herein, as well as other medical indications disclosed herein, will be within the skill of the skilled person.

As used herein, "a therapeutically effective amount" is one which reduces symptoms of a given condition or pathology, and preferably which normalizes physiological responses in an individual with the condition or pathology. Reduction of symptoms or normalization of physiological responses can be determined using methods routine in the art and may vary with a given condition or pathology. In one aspect, a therapeutically effective amount of one or more GLP-2 analogues of the invention or a pharmaceutical composition comprising one or more GLP-2 analogues of the invention is an amount which restores a measurable physiological parameter to substantially the same value (preferably to within 30%, more preferably to within 20%, and still more preferably, to within 10% of the value) of the parameter in an individual without the condition or pathology.

In one embodiment of the invention administration of the compounds or pharmaceutical composition of the present invention is commenced at lower dosage levels, with dosage levels being increased until the desired effect of preventing/treating the relevant medical indication, such as intestine and stomach related diseases is achieved. This may define a therapeutically effective amount. For the peptides of the present invention, alone or as part of a pharmaceutical composition, such doses may be between about 0.01 mg/kg and 100 mg/kg body weight, such as between about 0.01 mg/kg and 10 mg/kg body weight, for example between 10-100 micrograms/kg body weight.

For therapeutic use, a GLP-2 analogue of the invention may be formulated with a carrier that is pharmaceutically acceptable and is appropriate for delivering the peptide by the chosen route of administration. For the purpose of the present invention, peripheral parenteral routes include intravenous, intramuscular, subcutaneous, and intra peritoneal routes of administration. Certain compounds used in the present invention may also be amenable to administration by the oral, rectal, nasal, or lower respiratory routes. These are so-called non-parenteral routes. The present pharmaceutical composition comprises a GLP-2 analogue of the invention, or a salt or derivative thereof and a pharmaceutically acceptable carrier. Suitable pharmaceutically acceptable carriers are those used conventionally with peptide-based drugs, such as diluents, excipients and the like. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. Suitable pH buffering agents may be phosphate, citrate, acetate, tris/hydroxymethyl)aminomethane (TRIS), N-Tris(hydroxymethyl)methyl-3-aminopropanesulphonic acid (TAPS), ammonium bicarbonate, diethanolamine, histidine, which is a preferred buffer, arginine, lysine, or acetate or mixtures thereof. Preferred buffer ranges in certain embodiments are pH 4-8, pH 6.5-8, and more preferably pH 7-7.5. Preservatives, such as pars, meta, and ortho-cresol, methyl- and propylparaben, phenol, benzyl alcohol, sodium benzoate, benzoic acid, benzyl-benzoate, sorbic acid, propanoic acid, esters of p-hydroxybenzoic acid may be provided in the pharmaceutical composition. Stabilizers preventing oxidation, deamidation, isomerisation, racemisation, cyclisation, peptide hydrolysis, such as e.g. ascorbic acid, methionine, tryptophane. EDTA, asparagine, lysine, arginine, glutamine and glycine may be provided in the pharmaceutical composition. Stabilizers, preventing aggregation, fibrillation and precipitation, such as Sodium dodecyl sulphate, polyethylene glycol, carboxymethyl cellulose, cyclodextrine may also be provided in the pharmaceutical composition. Organic modifiers for solubilization or preventing aggregation, such as ethanol, acetic acid or acetate and salts thereof may be provided in the pharmaceutical composition. Isotonicity makers such as salts e.g. sodium chloride or most preferred carbohydrates e.g. dextrose, mannitol, lactose, trehalose, sucrose or mixtures thereof may be provided in the pharmaceutical composition. Detergents, such as Tween 20, Tween 80, SDS, Poloxamers e.g. Pluronic F-68, Pluronic F-127, may be provided in a pharmaceutical composition of the invention. Dyes and flavoring agents also may be provided in the pharmaceutical composition. In another embodiment, a pharmaceutically acceptable acid addition salt of a GLP-2 analogue of the invention is provided for. Suspending agents also may be used.

Organic modifiers, such as ethanol, tertiary-buthanol, 2-propanol, ethanol, glycerol, and polyethylene glycol may be provided in a pharmaceutical formulation for lyophilization of a lyophilized product. Bulking agents and isotonicity makers such as salt e.g. sodium chloride, carbohydrates e.g. dextrose, mannitol, lactose, trehalose, sucrose or mixtures thereof, amino acids (e.g., glycine and glutamate), or excipients such as cysteine, lecithin or human serum albumin, or mixtures thereof, may be provided in the pharmaceutical composition for lyophilization.

The pharmaceutical compositions of the present invention may be formulated and used as tablets, capsules or elixirs for oral administration; suppositories for rectal administration; preferably sterile solutions or sterile powder or suspensions for injectable administration; and the like. The dose and method of administration may be tailored to achieve optimal efficacy, but will depend on factors such as weight, diet, concurrent medication, which are recognizable to the skilled worker.

When administration is to be parenteral, such as intravenous and subcutaneous administration, injectable pharmaceutical compositions can be prepared in conventional forms, either as aqueous solutions or suspensions; lyophilized, solid forms suitable for reconstitution immediately before use or suspension in liquid prior to injection, or as emulsions.

Diluents for reconstitution of the lyophilized product may be, for example, chosen from the buffers listed above, or selected from water, saline, dextrose, mannitol, lactose, trehalose, sucrose, lecithin, albumin, sodium glutamate, cysteine hydrochloride, or water for injection with the addition of detergents, such as Tween 20, Tween 80, poloxamers (e.g., pluronic F-68 or pluronic F-127), polyethylene glycol, and/or with the addition of preservatives such as para-, meta-, and ortho-cresol, methyl- and propylparaben, phenol, benzyl alcohol, sodium benzoate, benzoic acid, benzyl-benzoate, sorbic acid, propanoic acid, esters of p-hydroxybenzoic acid, and/or with addition of an organic modifier such as ethanol, acitic acid, citric acid, lactic acid or salts thereof.

In addition, if desired, the injectable pharmaceutical compositions may contain minor amounts of non-toxic auxiliary substances, such as wetting agents, or pH buffering agents. Absorption enhancing preparations (e.g., liposomes, detergents and organic acids) also may be utilized.

In one embodiment of the invention, the compounds are formulated for administration by infusion, e.g., when used as liquid nutritional supplements for patients on total parenteral nutrition therapy (for example neonatals, or patients suffering from cachexia or anorexia), or by injection, for example subcutaneously, intraperitoneal or intravenously, and are accordingly utilized as aqueous solutions in sterile and pyrogen-free form and optionally buffered to physiologically tolerable pH, e.g., a slightly acidic or physiological pH. Formulation for intramuscular administration may be based on solutions or suspensions in plant oil, e.g. canola oil, corn oil or soy bean oil. These oil based formulations may be stabilized by antioxidants, e.g. BHA (butylated hydroxianisole) and BHT (butylated hydroxytoluene).

Thus, the GLP-2 analogues of the invention may be administered in a vehicle, such as distilled water or in saline, phosphate buffered saline, 5% dextrose solutions or oils. The solubility of a GLP-2 analogue of the invention may be enhanced, if desired, by incorporating a solubility enhancer, such as a detergents and/or emulsifier.

The aqueous carrier or vehicle can be supplemented for injectable use with an amount of gelatin that serves to depot the GLP-2 analogue at or near the site of injection, to provide a slow release to the desired site of action. Alternative gelling agents, such as hyaluronic acid, may also be useful as depot agents.

The peptide compounds of the present invention may be used alone, or in combination with compounds having an anti-inflammatory effect. Without being bound by theory, such a combination treatment may reinforce the beneficial treatment effects of the peptide analogues of the invention.

The therapeutic dosing and regimen most appropriate for patient treatment will, of course, vary with the disease or condition to be treated, and according to the patient's weight and other parameters. Without wishing to be bound by any particular theory, it is expected that doses, in the microgram/kg or mg/kg range, and shorter or longer duration or frequency of treatment may produce therapeutically useful results, such as a statistically significant increase, particularly in small bowel mass. In some instances, the therapeutic regimen may include the administration of maintenance doses appropriate for preventing tissue regression that occurs following cessation of initial treatment. The dosage sizes and dosing regimen most appropriate for human use may be guided by the results obtained by the present invention, and may be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person.

A human dose of a GLP-2 peptide according to the invention may in one embodiment be from about 10 microgram/kg body weight/day to about 10 mg/kg/day, preferably from about 50 microgram/kg/day to about 5 mg/kg/day, and most preferably about 100 microgram/kg/day to 1 mg/kg/day.

Medical Conditions

The GLP-2 analogues of the present invention are useful as a pharmaceutical agent for preventing or treating an individual suffering from low grade inflammation, e.g., local or systemic low grade inflammation. Low grade inflammation may include, but is not limited to: metabolic syndrome, obesity (e.g. abdominal obesity), diabetes, cardiovascular diseases, gastrointestinal inflammation, depression, alzheimer, arthritis, hypertension, dyslipidaemia and stroke. Gastrointestinal disorders, include the disorders of the upper gastrointestinal tract of the oesophagus, may be treated by administering an effective amount of a GLP-2 analogue of the invention, or a salt thereof as described herein. Stomach and intestinal-related disorders include ulcers of any aetiology (e.g., peptic ulcers, Zollinger-Ellison Syndrome, drug-induced ulcers, ulcers related to infections or other pathogens), digestion disorders, malabsorption syndromes, short-bowel syndrome, cul-de-sac syndrome, inflammatory bowel disease (Crohns disease and ulcerative colitis), celiac sprue (for example arising from gluten induced enteropathy or celiac disease), tropical sprue, hypogammaglobulinemic sprue, and chemotherapy and/or radiationhemotherapy induced mucositis and diarrhea.

For patients having gastrointestinal mucosal neoplasia, or an increased risk of gastrointestinal mucosal neoplasia, it may be desirable to select a compound so as to reduce or abrogate the risk of reduced side effects such as stimulation or aggravation of gastrointestinal mucosal neoplasia.

Particular conditions that may be treated with a GLP-2 analogue of the invention include the various forms of sprue including celiac sprue which results from a toxic reaction to alpha-gliadin from heat and may be a result of gluten-induced enteropathy or celiac disease, and is marked by a significant loss of villae of the small bowel; tropical sprue which results from infection and is marked by partial flattening of the villae; hypogammaglobulinemic sprue which is observed commonly in patients with common variable immunodeficiency or hypogammaglobulinemia and is marked by significant decrease in villus height. The therapeutic efficacy of the GLP-2 analogue treatment may be monitored by enteric biopsy to examine the villus morphology, by biochemical assessment of nutrient absorption, by non invasive determination of intestinal permeability, by patient weight gain, or by amelioration of the symptoms associated with these conditions.

The GLP-2 analogues of the present invention may be useful as pharmaceutical agents for preventing or treating stomach related disorders including ulcers of any aetiology (e.g., peptic ulcers, Zollinger-Ellison Syndrome, drug-induced ulcers, ulcers related to infections or other pathogens), Other conditions that may be treated with the GLP-2 analogues of the invention, or for which the GLP-2 analogues may be useful prophylactically, include in addition to the above mentioned radiation enteritis, infectious or post-infectious enteritis, and small intestinal damage due to cancer-chemotherapeutic or toxic agents.

The GLP-2 analogues may also be used for the treatment of malnutrition, for example cachexia and anorexia.

A particular embodiment of the invention is concerned with using the present peptides for the prevention and/or treatment of intestinal damage and dysfunction. The stem cells of the small intestinal mucosa are particularly susceptible to the cytotoxic effects of chemotherapy due to their rapid rate of proliferation (Keefe et al., Gut 2000; 47:

632-7). Administration of the present GLP-2 peptide agonists may enhance trophic effect in the intestinal crypts and rapidly provide new cells to replace the damaged intestinal epithelium following chemotherapy and/or radiation therapy. A goal to be achieved by administering the GLP-2 analogues of the invention is to reduce morbidity related to gastrointestinal damage of patients undergoing chemotherapy treatment while increasing tolerance to more aggressive chemotherapy, radiation and combination chemotherapy and radiation therapies. Concomitant prophylactic or therapeutic treatment may be provided in accordance with the present invention to patients undergoing or about to undergo radiation therapy.

Gastrointestinal mucositis after anti-cancer chemotherapy is an increasing problem that is essentially untreatable once established, although it gradually remits. Studies conducted with the commonly used cytostatic cancer drugs 5-FU and irinotecan have demonstrated that effective chemotherapy with these drugs predominantly affects structural integrity and function of the small intestine, while the colon is less sensitive and mainly responds with increased mucus formation (Gibson et al., J Gastroenterol Hepatol. 18(9):1095-1100, 2003; Tamaki et al., J Int Med Res. 31(1):6-16, 2003).

In another embodiment, the invention describes a method of treating DPP-IV (dipeptidylpeptidase-IV) mediated conditions by administering to a patient in need thereof an effective amount of a GLP-2 analogue, or a salt thereof. Such diseases include conditions in which the DPP-IV enzyme is over expressed.

The pharmaceutical composition may in one embodiment be formulated to cause slow release of said GLP-2 analogue, or a salt or derivative thereof as described above.

It is envisaged that the present peptides may be employed in a method of treating neo-natals by administering an effective amount of a GLP-2 analogue, or a salt thereof, of the invention. Complications with feeding neonatals due to the lack of development of the intestine may be overcome by using the peptide agonists of the invention.

In some embodiments, the invention describes a method of treating DPP-IV (dipeptidylpeptidase-IV) mediated conditions by administering to a patient in need thereof an effective amount of a GLP-2 analogue, or a salt thereof, of the invention. Such diseases include conditions in which the DPP-IV enzyme is over expressed.

EXAMPLES

The following examples are provided to illustrate preferred aspects of the invention and are not intended to limit the scope of the invention.
General Peptide Synthesis—
Apparatus and Synthetic Strategy Peptides were synthesized batchwise in a polyethylene vessel equipped with a polypropylene filter for filtration using 9-fluorenylmethyloxycarbonyl (Fmoc) as N-α-amino protecting group and suitable common protection groups for side-chain functionalities.

Solid phase peptide synthesis was performed on a CEM Liberty Peptide Synthesizer using standard Fmoc chemistry. TentaGel S Ram resin (1 g; 0.25 mmol/g) was swelled in NMP (10 ml) prior to use and transferred between tube and reaction vessel using DCM and NMP.
Coupling An Fmoc-amino acid in NMP/DMF/DCM (1:1:1; 0.2 M; 5 ml) was added to the resin in a CEM Discover microwave unit together with HATU/NMP (0.5 M; 2 ml) and DIPEA/NMP (2.0 M; 1 ml). The coupling mixture was heated to 75° C. for 5 min while nitrogen was bubbled through the mixture. The resin was then washed with NMP (4×10 ml).

Alternatively, an Fmoc-amino acid in DMF/DCM (2:1; 0.2 M; 5 ml) was added to the resin in a CEM Discover microwave unit together with COMU/DMF (0.5 M; 2 ml) and DIPEA/DMF (2.0 M; 1 ml). The coupling mixture was heated to 75° C. for 5 min while nitrogen was bubbled through the mixture. The resin was then washed with NMP (4×10 ml).
Deprotection Piperidine/NMP (20%; 10 ml) was added to the resin for initial deprotection and the mixture was heated by microwaves (30 sec; 40° C.). The reaction vessel was drained and a second portion of piperidine/NMP (20%; 10 ml) was added and heated (75° C.; 3 min.) again. The resin was then washed with NMP (6×10 ml).

Alternatively, piperidine/DMF (20%; 10 ml) was added to the resin for initial deprotection and the mixture was heated by microwaves (30 sec; 40° C.). The reaction vessel was drained and a second portion of piperidine/DMF (20%; 10 ml) was added and heated (75° C.; 3 min.) again. The resin was then washed with DMF (6×10 ml).
Side Chain Acylation (Optional)

Fmoc-Lys(ivDde)-OH or alternatively another amino acid with an orthogonal side chain protective group is introduced at the position of the acylation. The N-terminal of the peptide backbone is then Boc-protected using Boc2O or alternatively by using a Boc-protected amino acid in the last coupling. While the peptide is still attached to the resin, the orthogonal side chain protective group is selectively cleaved using freshly prepared hydrazine hydrate (2-4%) in NMP for 2×15 min. The unprotected lysine side chain is first coupled with Fmoc-Glu-OtBu or another spacer amino acid, which is deprotected with piperidine and acylated with a lipophilic moiety using the peptide coupling methodology as described above. Abbreviations employed are as follows:
ivDde: 1-(4,4-dimethyl-2,6-dioxocyclohexylidene)3-methyl-butyl
Dde: 1-(4,4-dimethyl-2,6-dioxocyclohexylidene)-ethyl
DCM: dichloromethane
DMF: N,N-dimethylformamide
DIPEA: diisopropylethylamine
EtOH: ethanol
Et2O: diethyl ether
HATU: N-[(dimethylamino)-1H-1,2,3-triazol[4,5-b]pyridine-1-ylmethylene]-N-methylmethanaminium hexafluorophosphate N-oxide
MeCN: acetonitrile
NMP: N-methylpyrrolidone
TFA: trifluoroacetic acid
TIS: triisopropylsilane
Cleavage The resin was washed with EtOH (3×10 ml) and Et2O (3×19 ml) and dried to constant weight at room temperature (r.t.). The crude peptide was cleaved from the resin by treatment with TFA/TIS/water (9512.5/2.5; 40 ml, 2 h; r.t.) or TFA/DODT (95/5; 40 ml, 2 h; r.t.). Most of the TFA was removed at reduced pressure and the crude peptide was precipitated and washed three times with diethylether and dried to constant weight at room temperature.
HPLC Purification of the Crude Peptide The crude peptide was purified to approximately or greater than 90% by preparative reverse phase HPLC using a PerSeptive Biosystems VISION Workstation equipped with a C-18 column (5 cm; 10 μm) and a fraction collector and run at 35 ml/min with a gradient of buffer A (0.1% TFA, aq.) and buffer B (0.1% TFA, 90% MeCN, aq.). Fractions were analyzed by analytical HPLC and MS and relevant fractions were pooled and lyophilized. The final product was characterized by HPLC and MS.

Fmoc-protected amino acids were purchased from Advanced ChemTech (ACT) in suitable side-chain protected forms.

Coupling Reagents

Coupling reagent diisopropylcarbodiimide (DIC) was purchased from Riedel de-Häen, Germany.

Solid Supports

Peptides were synthesized on TentaGel S resins 0.22-0.31 mmol/g. TentaGel S-Ram, TentaGel S RAM-Lys(Boc)Fmoc (Rapp polymere, Germany) were used in cases where a C-terminal amidated peptide was preferred, while TentaGel S PHB, for example TentaGel S PHB Asp(Boc)Fmoc were used when a C-terminal free carboxylic acid was preferred.

Deprotection of Asp (e.g. in position 15) was performed using 0.1 M formic acid in 30% Piperidine/NMP when the amino acid in the following position (e.g, position 16) was Gly and no heating during synthesis or deprotection.

Catalysts and Other Reagents

Dilsopropylethylamine (DIEA) was purchased from Aldrich, Germany, piperidine and pyridine from Riedel-de Häen, Frankfurt, Germany. Ethandithiol was purchased from Riedel-de Häen, Frankfurt, Germany. 3,4-dihydro-3-hydroxy-4-oxo-1,2,3-benzotrazine (Dhbt-OH), 1-hydroxybenzotriazole (HOBt) (HOAt) were obtained from Fluka, Switzerland. Coupling procedures The amino acids were coupled as in situ generated HObt or HOAt esters made from appropriate N-α-protected amino acids and HObt or HOAt by means of DIC in DMF. Acylations were checked by the ninhydrin test performed at 80° C. in order to prevent Fmoc deprotection during the test (Larsen, B. D. and Holm, A., Int J. Peptide Protein Res. 43, 1994, 1-9).

Deprotection of the N-α-Amino Protecting Group (Fmoc).

HPLC Purification of the Crude Peptide

The crude peptide products were purified PerSeptive Biosystems VISION Workstation. VISION 3.0 software was used for instrument control and data acquisition. The following column and HPLC buffer system was used:

Column: Kromasil KR 100 Å, 10 mm C-8, 250×50.8 mm.
Buffer system: Buffers: A: 0.1% TFA in MQV; B: 0.085% TFA, 10% MQV, 90% MeCN.
Gradient: 0-37 min. 0-40% B
Flow 35 ml/min, UV detection: I=215 nm and 280 nm.

Mass Spectroscopy

The peptides were dissolved in super gradient methanol (Labscan, Dublin, Ireland), milli-Q water (Millipore, Bedford, Mass.) and formic acid (Merck, Damstadt, Germany) (50:50:0.1 v/v/v) to give concentrations between 1 and 10 mg/mi. The peptide solutions (20 ml) were analysed in positive polarity mode by ESI-TOF-MS using a LCT mass spectrometer (Micromass, Manchester, UK) accuracy of +/−0.1 m/z.

After purification using preparative HPLC as described above, the peptide product was collected and the identity of the peptide was confirmed by ES-MS. This procedure was used for the synthesis of all peptides exemplified further below.

Compounds Synthesised

The compounds of Table 1 were synthesized using the above techniques.

TABLE 1

Compounds synthesized

| Compound | Sequence |
|---|---|
| 1 | Hy-H-Aib-DGSFSDEMNTILDNQAARDFINWLIQTKITD-OH |
| 2 | Hy-HGDGSFSDEMNTILDNKAARDFINWLIQTKITD-OH |
| 3 | Hy-HGDGSFSDEMNTILDGQAARDFINWLIQTK-NH$_2$ |
| 4 | Hy-HGDGSFSSEMNTILDSQAARDFINWLIQTKITD-OH |
| 5 | Hy-HGEGTFTSDLSKQMEGQAVRDFIEWLIQTKITD-OH |
| 6 | Hy-HGEGTFTSDLSKQMESKAARDFIEWLIQTKITD-OH |
| 7 | Hy-HGDGSFSSELATILDGKAARDFINWLIQTKITD-OH |
| 8 | Hy-HGEGTFTSDLSTILENKAARDFIEWLIQTKITD-OH |
| 9 | Hy-HGEGSFSSDLSTILENKAARDFIEWLIQTKITD-OH |
| 10 | Hy-H-Aib-DGSFSDELNTILDGKAARDFINWLIQTK-NH$_2$ |
| 11 | Hy-HGDGSFSSELATILDGQAARDFIAWLIQTKITD-OH |
| 12 | Hy-HGDGSFSDEMNTILDGQAARDFINWLIQTK-NH$_2$ |
| 13 | Hy-HGEGSFSSDLSTILEGKAARDFIEWLIQTKITD-OH |

Example 1 Synthesis of Compound 12

Solid phase peptide synthesis was performed on a CEM Liberty Peptide Synthesizer using standard Fmoc chemistry. TentaGel S Ram S resin (1.33 g; 0.25 mmol/g) was swelled in DMF (10 ml) prior to use and transferred between tube and reaction vessel using DCM and DMF.

Coupling

An Fmoc-amino acid in DMF/DCM (2:1; 0.2 M; 5 ml) was added to the resin in a CEM Discover microwave unit together with COMU/DMF (0.5 M; 2 ml) and DIPEA&DMF (2.0 M; 1 ml). The coupling mixture was heated to 75° C. for 5 min while nitrogen was bubbled through the mixture. The resin was then washed with DMF (4×10 ml). Fmoc-Phe-Ser(Psi Me,Me,Pro)-OH pseudoproline was used for amino acid number six and seven.

Deprotection

Piperidine/DMF (20%; 10 ml) was added to the resin for initial deprotection and the mixture was heated by microwaves (30 sec; 40° C.). The reaction vessel was drained and a second portion of piperidine/DMF (20%; 10 ml) was added and heated (75° C.; 3 min.) again. The resin was then washed with DMF (6×10 ml).

The resin was washed with EtOH (3×10 ml) and Et2O (3×10 ml) and dried to constant weight at room temperature (r.t.). The crude peptide was cleaved from the resin by treatment with TFA/DODT (95/5; 60 ml, 2 h; r.t.). Most of the TFA was removed at reduced pressure and the crude peptide was precipitated and washed three times with diethylether and dried to constant weight at room temperature.

HPLC Purification of the Crude Peptide

The crude peptide was first purified to 45% by preparative reverse phase HPLC using a PerSeptive Biosystems VISION Workstation equipped with a Gemini NX 5 μC-18 110A, 10×250 mm column and a fraction collector and run at 35 ml/min with a gradient of buffer A (0.1% TFA, aq.) and buffer B (0.1% TFA, 90% MeCN, aq.). Fractions were analyzed by analytical HPLC and MS and relevant fractions were pooled and lyophilized. The product (143 mg) was purified a second time with a C4 Jupiter 2, 12×25 cm column, to yield 27 mg, with a purity of 89% as characterized by HPLC and MS. Calculated monoisotopic MW=3377.61, found 3377.57.

Example 2. GLP-2-Receptor Efficacy Assays

A cAMP AlphaScreen® assay from Perkin Elmer was used to quantitate a cAMP response to a GLP-2 analogue. Teduglutide was the reference compound in this assay and has an $EC_{50}$ of approximately 0.01 nM. Test compounds inducing an increase in the intracellular level of cAMP were tested in this assay, and the response normalized relative to a positive and negative control to calculate the $EC_{50}$ and maximal response from the concentration response curve. The results are listed in Table 2.

Generation of Cell Line Expressing Human GLP-1 Receptors

The cDNA encoding the human glucagon-like peptide 1 receptor (GLP-1R) (primary accession number P43220) was cloned from the cDNA BC112126 (MGC:138331/IMAGE: 8327594). The DNA encoding the GLP-1-R was amplified by PCR using primers encoding terminal restriction sites for subcloning. The 5'-end primers additionally encoded a near Kozak consensus sequence to ensure efficient translation. The fidelity of the DNA encoding the GLP-1-R was confirmed by DNA sequencing. The PCR products encoding the GLP-1-R were subcloned into a mammalian expression vector containing a neomycin (G418) resistance marker. The mammalian expression vectors encoding the GLP-1-R were transfected into HEK293 cells by a standard calcium phosphate transfection method. 48 hours after transfection, cells were seeded for limited dilution cloning and selected with 1 mg/ml G418 in the culture medium. Three weeks later, 12 surviving colonies of GLP-1-R expressing cells were picked, propagated and tested in the GLP-1 receptor efficacy assays as described below. One GLP-1-R expressing clone was selected for compound profiling.

Generation of Cell Line Expressing Human GLP-2 Receptors

The hGLP2-R was purchased from MRC-geneservice, Babraham, Cambridge as an image clone: 5363415 (11924-117). For subcloning into an mammalian expression vector, primers for subcloning were obtained from DNA-Technology, Risskov, Denmark. The 5' and 3' primers used for the PCR reaction include terminal restriction sites for cloning and the context of the 5' primer is modified to a Kozak consensus without changing the sequence of the product encoded by the ORF. A standard PCR reaction was run using image clone 5363415 (11924-117) as a template with the above mentioned primers and Polymerase Herculase II Fusion in a total vol, of 50 µl. The generated PCR product was purified using GFX PCR and Gel band purification kit, digested with restriction enzymes and cloned into the mammalian expression vector using Rapid DNA Ligation Kit. Ligation reaction was transformed to XL10 Gold Ultracompetent cells and colonies were picked for DNA production using Endofree Plasmid maxi kit. Subsequent sequence analysis was conducted by MWG Eurofins, Germany. The done was confirmed to be the hGLP-2 receptor, splice variant rs17681684.

HEK293 cells were transfected using the Lipofectamine PLUS transfection method. The day before transfection, HEK293 cells were seeded in two T75 flasks at a density of $2 \times 10^6$ cells/T75 flask in cell culturing medium without antibiotics. On the day of transfection, cells were washed with 1×DPBS and medium was replaced with Optimem to a volume of 5 mL/T75 flask before addition of Lipofectamine-plasmid complexes were added gently and drop wise to the cells in T75 flasks and replaced with growth medium after 3 hours and again to growth medium supplemented with 500 µg/mL G418 after 24 hours. After 4 weeks in G418 selection, colonies were picked and tested in a functional assay. One colony was selected for use in compound profiling.

GLP-1-Receptor Efficacy Assays

The cAMP AlphaScreen® assay from Perkin Elmer was used to quantitate the cAMP response to activation of the GLP1 and GLP2 receptor, respectively. Exendin-4 (ZP24) was used as reference compound for GLP1 receptor activation and Teduglutide (ZP1559) as reference compound for GLP2 receptor activation. Data from test compounds eliciting an increase in the intracellular level of cAMP were normalized relative to the positive and negative control (vehicle) to calculate the $EC_{50}$ and maximal response from the concentration response curve. The results are listed in Table 2.

TABLE 2

GLP-1R and GLP-2R EC50 measurements

| Compound | Sequence | GLP-2R EC50 (nM) | GLP-1R EC50 (nM) |
|---|---|---|---|
| GLP-1 | | >1000 | 0.01 |
| GLP-2 (Gly2) | | 0.06 | >200/1000 |
| 1 | Hy-H-Aib-DGSFSDEMN TILDNQAARDFINWLIQT KITD-OH | 0.12 | 44 |
| 2 | Hy-HGDGSFSDEMNTILD NKAARDFINWLIQTKIT D-OH | 0.02 | 77 |
| 3 | Hy-HGDGSFSDEMNTILD GQAARDFINWLIQTK-NH$_2$ | 0.07 | 9 |
| 4 | Hy-HGDGSFSSEMNTILD SQAARDFINWLIQTKIT D-OH | 0.06 | 25 |
| 5 | Hy-HGEGTFTSDLSKQME GQAVRDFIEWLIQTKIT D-OH | 0.2 | 1.0 |
| 6 | Hy-HGEGTFTSDLSKQME SKAARDFIEWLIQTKIT D-OH | 0.2 | 110 |
| 7 | Hy-HGDGSFSSELATILD GKAARDFINWLIQTKIT D-OH | 0.2 | 0.78 |
| 8 | Hy-HGEGTFTSDLSTILE NKAARDFIEWLIQTKIT D-OH | 0.008 | 16 |
| 9 | Hy-HGEGSFSSDLSTILE NKAARDFIEWLIQTKIT D-OH | 0.2 | 9.10 |
| 10 | Hy-H-Aib-DGSFSDELN TILDGKAARDFINWLIQT K-NH$_2$ | 3.5 | 0.03 |
| 11 | Hy-HGDGSFSSELATILD GQAARDFIAWLIQTKIT D-OH | 0.2 | 0.34 |

TABLE 2-continued

GLP-1R and GLP-2R EC50 measurements

| Com-pound | Sequence | GLP-2R EC50 (nM) | GLP-1R EC50 (nM) |
|---|---|---|---|
| 12 | Hy-HGDGSFSDEMNTILDGQAARDFINWLIQTK-NH$_2$ | 9.0 | 0.07 |
| 13 | Hy-HGEGSFSSDLSTILEGKAARDFIEWLIQTKITD-OH | 0.1 | 18 |

Example 3: Effect on Glucose Tolerance in Normal Mice

Normal chow-fed C57BL/6J male mice were used. The mice were kept in standard housing conditions (light-, temperature-, and humidity-controlled room (12:12 h light-dark cycle, with lights on at 06.00-18.00 h; 24° C.; 50% relative humidity)), and each dosing group consisted of 10 animals.

Prior to the oral glucose tolerance test (OGTT), animals were fasted for 5 h. One hour before glucose challenge (time t=−60 min) baseline blood glucose was measured. Immediately after the blood sample, the animals were dosed once subcutaneously with compound at the indicated amount or PBS (vehicle). One hour later at t=0 min, a 2 g/kg oral gavage of glucose (0.4 g/ml in water diluted from glucose SAD 0.456 g/l; dose volume 5 ml/kg) was given to the animals. After glucose administration, tail vein blood was drawn for glucose measurements at t=15, 30, 60, 120 min.

Results

Figure 2:
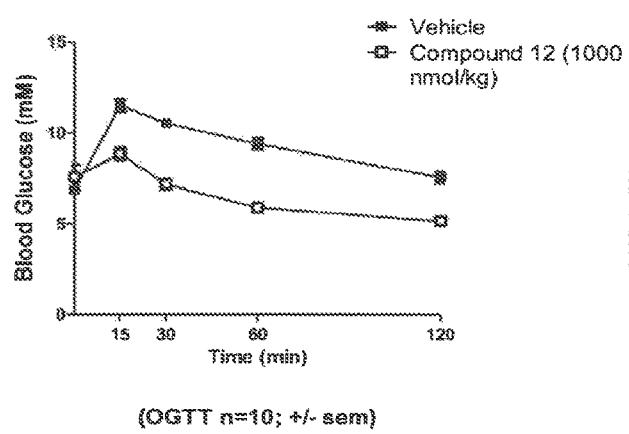
FIG. 2 shows the effects of Compound 12 or vehicle administration on the oral glucose tolerance test (OGTT). One hour before glucose challenge, baseline measurements were taken and Compound 12/vehicle was administered. (A) Blood glucose levels during the experimental period (B) AUC of blood glucose measurements.
Figure 2:
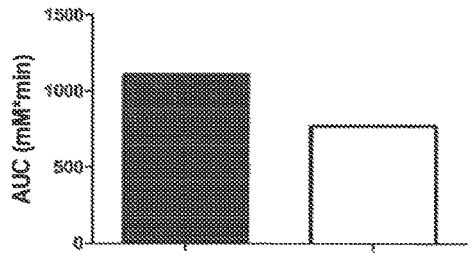

Vehicle treated mice displayed a typical response to glucose challenge, with an increase in blood glucose levels in the first 30 minutes, followed by return to baseline levels after 120 minutes. Test compound significantly reduced the blood glucose response (FIG. 2).

Example 4: Effect on Intestinal Weight in Normal Rats

Normal chow-fed Wistar male rats were used. The rats were kept in standard housing conditions (light-, temperature-, and humidity-controlled room (12:12 h light-dark cycle, with lights on at 06.00-18.00 h; 24° C.; 50% relative humidity)), and each dosing group consisted of 6 animals. Rats were dosed once daily via the subcutaneous route, for four days with compound at the indicated amount or PBS (vehicle). On day five, rats were sacrificed and small intestinal weight wet measured.

Results

Figure 3:
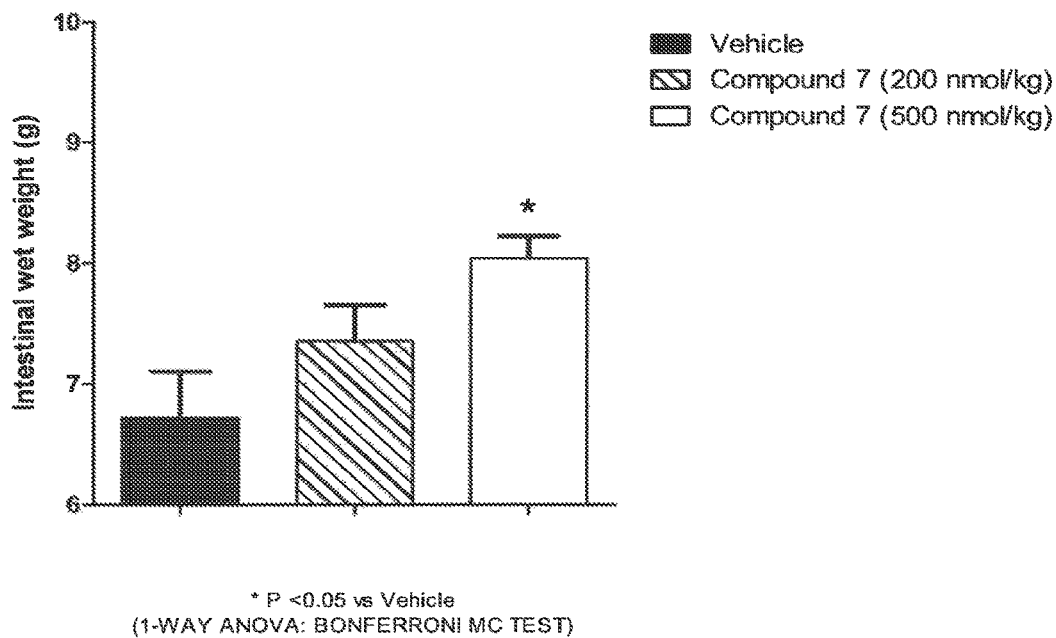
FIG. 3 shows the effects of Compound 7 or vehicle administration on intestinal wet weight. Animals were treated with compound 7 or vehicle once daily, for four days and on day 5 the small intestine was removed and weighed.

Test compound increased intestinal weight in a dose dependant manner (FIG. 3).

Example 5: Effect of Compound 7 in Diet-Induced Obese Mice

Diet-induced obesity was generated by feeding C57BL/6J male mice with high fat diet (Research Diet 60% fat (D12492) Research Diet Inc., New Brunswick, USA). The mice were kept in standard housing conditions (light-, temperature-, and humidity-controlled room (12:12 h light-dark cycle, with lights on at 06.00-18.00 h; 24° C.; 50% relative humidity)).

The vehicle treated dosing group contained 8 animals and the compound 7 treated groups consisted of 12 animals/group. All animals were mock treated for 7 days (once daily, SC, 100 µl vehicle) to acclimatize the animals to handling and injections, followed by treatment (vehicle or compound 7) for 14 days (twice daily, SC, 5 ml/kg). Animals were fasted overnight (day 11-12) and blood was drawn for analysis of glucose and insulin. On day 14, animals were sacrificed and small and large intestines removed, washed and weighed.

Results

Figure 4:
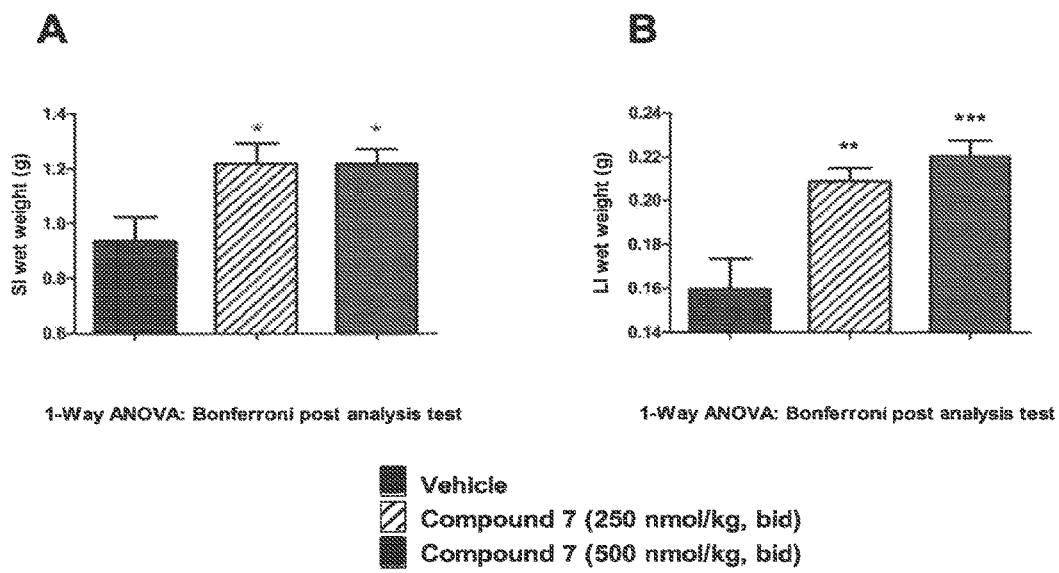
FIG. 4 shows effects of two weeks administration of test compound 7 or vehicle administration on intestinal weight. (A) Small intestinal wet weight (B) Large intestinal wet weight.

Compound 7, dosed twice daily for 14 days, significantly increased the small and large intestinal mass when compared to vehicle treated controls (FIG. 4).

Figure 5:
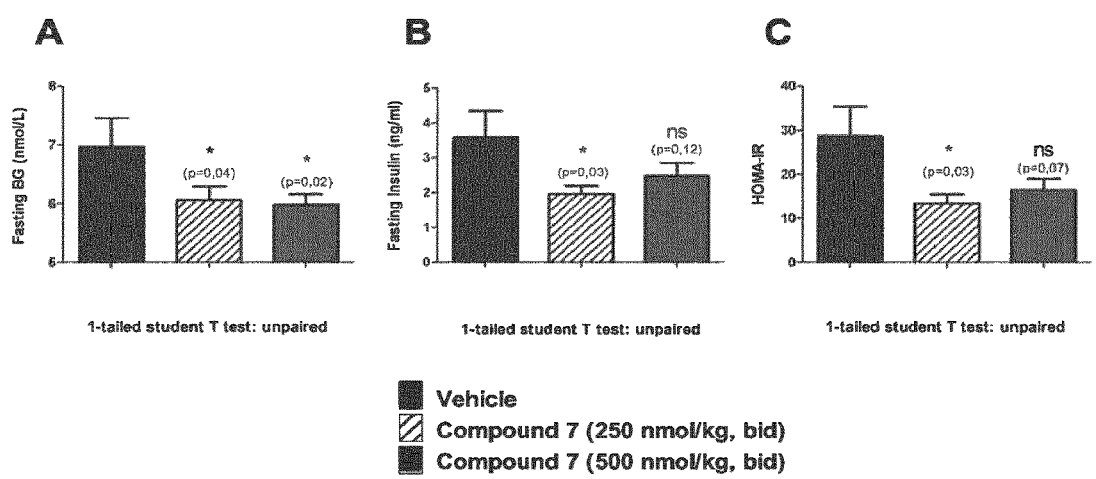
FIG. 5 shows effects of two weeks administration of test compound 7 or vehicle administration on glucose homeostasis. Animals were fasted overnight, and blood drawn for analysis of (A) fasting blood glucose (B) fasting plasma insulin and (C) homeostatic model assessment-insulin resistance (HOMA-IR).

Compound 7, dosed twice daily for 14 days, reduced fasting blood glucose and plasma insulin levels, and gave a lower HOMA-IR index than vehicle treated controls (FIG. 5).

While the invention has been described in conjunction with the exemplary embodiments described above, many equivalent modifications and variations will be apparent to those skilled in the art when given this disclosure. Accordingly, the exemplary embodiments of the invention set forth are considered to be illustrative and not limiting. Various changes to the described embodiments may be made without departing from the spirit and scope of the invention. All documents cited herein are expressly incorporated by reference.

The invention claimed is:

1. A GLP-2 analogue represented by the general Formula 1:

$$R^1\text{-His-X2-X3-Gly-X5-Phe-X7-X8-X9-X10-X11-X12-X13-X14-X15-X16-X17-Ala-X19-X20-X21-Phe-Ile-X24-Trp-Leu-X27-X28-X29-X30-X31-X32-X33-X34-}R^2 \quad (I)$$

or a pharmaceutically acceptable salt thereof, wherein: $R^1$ is hydrogen, $C_{1-4}$ alkyl, acetyl, formyl, or benzoyl;
X2 is Gly, Ala or Aib;
X3 is Glu, Gln or Asp;
X5 is Ser or Thr;
X7 is Ser or Thr;
X8 is Asp, Glu or Ser; X9 is Glu or Asp;
X10 is Met, Val, Leu or Tyr;
X11 is Asn, Ser or Ala;
X12 is Thr, Ser or Lys;
X13 is Ile, Leu, Val, Tyr, Phe or Gln; X14 is Leu or Met;
X15 is Asp or Glu;
X16 is Asn, Gln, Gly, Ser, Ala, Glu or Lys; X17 is Gln, Lys, Arg, His or Glu;
X19 is Ala or Val;
X20 is Arg, Lys or His; X21 is Asp, Glu or Leu;
X24 is Asn, Ala, Glu or Lys;
X27 is Ile, Leu, Val, Glu or Lys:
X28 is Gln, Asn, Lys, Ser, Gly, Y1 or absent;
X29 is Thr, Ala, Y1 or absent;
X30 is Lys, Y1 or absent;
X31 is Ile, Pro, Y1 or absent;
X32 is Thr, Y1 or absent;
X33 is Asp, Asn, Y1 or absent;
X34 is Y1 or absent;
Y1 is Gly-Gly-Pro-Ser-Ser-Gly Ala-Pro-Pro-Pro-Ser, or Lys-Asn-Gly-Gly-Pro-Ser-Ser- Gly-Ala-Pro-Pro-Pro-Ser; and
$R^2$ Is $NH_2$ or OH; wherein
the GLP-2 analogue contains no more than one Y1;
if any of X28 to X33 is Y1, those positions X29 to X34 downstream of that Y1 are absent;
if any of X28 to X33 is absent, those positions X29 to X33 downstream of that position are also absent; and
with the proviso that the GLP-2 analogue of Formula I is not

```
                                        (SEQ ID NO: 3)
HGDGSFSDEMNTILDGQAARDFINWLIQTKITD;

(SEQ ID NO: 4)
HGDGSFSDEMNTILDNQAARDFINWLIQTKITD;
or (SEQ ID NO: 5)
HGDGSFSDEMNTILDSQAARDFINWLIQTK.
```

2. The GLP-2 analogue according to claim 1, wherein:
X2 is Gly, Ala or Aib;
X3 is Glu, Gln or Asp;
X5 is Ser or Thr;

X7 is Ser or Thr;
X8 is Asp, Glu or Ser; X9 is Glu or Asp;
X10 is Met, Val, Leu or Tyr;
X11 is Asn or Ser;
X13 is Ile, Leu, Val, Tyr, Phe or Gln;
X14 is Leu or Met; X12 is Thr or Lys; X15 is Asp or Glu;
X16 is Asn, Gln, Gly, Ser, Ala, Glu or Lys;
X17 is Gln or Lys;
X19 is Ala or Val;
X20 is Arg, Lys or His;
X21 is Asp, Glu or Leu;
X24 is Asn, Ala, Glu or Lys;
X27 is Ile, Leu, Val or Lys:
X28 is Gln, Asn, Gly, Y1 or absent; X29 is Thr, Ala, Y1 or absent;
X30 is Lys, Y1 or absent;
X31 is Ile, Pro, Y1 or absent; X32 is Thr, Y1 or absent;
X33 is Asp, Asn, Y1 or absent;
X34 is Y1 or absent;
Y1 is -Gly-Gly-Pro-Ser-Ser-Gly-Ala-Pro-Pro-Pro-Ser; and
R² is NH₂ or OH; wherein
the GLP-2 analogue contains no more than one Y1;
if any of X28 to X33 is Y1, those positions X29 to X34 downstream of that Y1 are absent;
if any of X28 to X33 is absent, those positions X29 to X33 downstream of that position are also absent; and
with the proviso that the GLP-2 analogue of Formula I is not

```
                                               (SEQ ID NO: 3)
HGDGSFSDEMNTILDGQAARDFINWLIQTKITD;

(SEQ ID NO: 4)
HGDGSFSDEMNTILDNQAARDFINWLIQTKITD;
or (SEQ ID NO: 5)
HGDGSFSDEMNTILDSQAARDFINWLIQTK.
```

3. A GLP-2 analogue represented by the general Formula Ia:

$$R^1\text{-His-X2-X3-Gly-X5-Phe-X7-X8-X9-X10-X11-X12-X13-}$$
$$\text{Leu-X15-X16-X17-Ala-Ala-X20-X21-Phe-Ile-X24-Trp-}$$
$$\text{Leu-X27-X28-X29-X30-X31-X32-X33-}R^2 \quad \text{(Ia)}$$

or a pharmaceutically acceptable salt thereof, wherein: R¹ is hydrogen, C₁₋₄ alkyl, acetyl, formyl, or benzoyl;
X2 is Gly, Ala or Aib;
X3 is Glu, Gln or Asp;
X5 is Ser or Thr;
X7 is Ser or Thr;
X8 is Asp, Glu or Ser; X9 is Glu or Asp;
X10 is Met, Val, Leu or Tyr;
X11 is Asn or Ser;
X12 is Thr, Ser or Lys;
X13 is Ile, Leu, Val, Tyr, Phe or Gln; X15 is Asp or Glu;
X16 is Asn, Gln, Gly, Ser, Ala, Glu or Lys; X17 is Gln, Lys, Arg, His or Glu;
X20 is Arg, Lys or His; X2i is Asp, Glu or Leu;
X24 is Asn, Ala, Glu or Lys;
X27 is Ile, Leu, Val, Glu or Lys:
X28 is Gln, Asn, Lys, Ser, Gly, Y1 or absent; X29 is Thr, Y1 or absent;
X30 is Lys, Y1 or absent;
X31 is Ile, Pro, Y1 or absent;
X32 is Thr, Y1 or absent;
X33 is Asp, Asn, Y1 or absent;
Y1 is Gly-Gly-Pro-Ser-Ser-Gly-Ala-Pro-Pro-Pro-Ser; and
R² is NH₂ or OH; wherein
the GLP-2 analogue contains no more than one Y1;
if any of X28 to X33 is Y1, those positions X29 to X34 downstream of that Y1 are absent;
if any of X28 to X33 is absent, those positions X29 to X33 downstream of that position are also absent; and
with the proviso that the GLP-2 analogue of Formula Ia is not

```
                                               (SEQ ID NO: 3)
HGDGSFSDEMNTILDGQAARDFINWLIQTKITD;

(SEQ ID NO: 4)
HGDGSFSDEMNTILDNQAARDFINWLIQTKITD;
or (SEQ ID NO: 5)
HGDGSFSDEMNTILDSQAARDFINWLIQTK.
```

4. The GLP-2 analogue according to claim 3, wherein:
X2 is Gly, Ala or Aib;
X3 is Glu, Gln or Asp;
X5 is Ser or Thr;
X7 is Ser or Thr;
X8 is Asp, Glu or Ser; X9 is Glu or Asp;
X10 is Met, Val, Leu or Tyr;
X11 is Asn or Ser; X12 is Thr or Lys;
X13 is Ile, Leu, Val, Tyr, Phe or Gln;
X15 is Asp or Glu;
X16 is Asn, Gln, Gly, Ser, Ala, Glu or Lys;
X17 is Gln or Lys;
X20 is Arg, Lys or His;
X21 is Asp, Glu or Leu;
X24 is Asn, Ala, Glu or Lys;
X27 is Ile, Leu, Val or Lys:
X28 is Gln, Asn, Gly, Y1 or absent;
X29 is Thr, Y1 or absent;
X30 is Lys, Y1 or absent;
X31 is Ile, Pro, Y1 or absent;
X32 is Thr, Y1 or absent;
X33 is Asp, Asn, Y1 or absent;
Y1 is Gly-Gly-Pro-Ser-Ser-Gly-Ala-Pro-Pro-Pro-Ser; and
R² is NH₂ or OH; wherein
the GLP-2 analogue contains no more than one Y1;
if any of X28 to X33 is Y1, those positions X29 to X34 downstream of that Y1 are absent;
if any of X28 to X33 is absent, those positions X29 to X33 downstream of that position are also absent; and
with the proviso that the GLP-2 analogue of Formula Ia is not

```
                                               (SEQ ID NO: 3)
HGDGSFSDEMNTILDGQAARDFINWLIQTKITD;

(SEQ ID NO: 4)
HGDGSFSDEMNTILDNQAARDFINWLIQTKITD;
or (SEQ ID NO: 5)
HGDGSFSDEMNTILDSQAARDFINWLIQTK.
```

5. The GLP-2 analogue according to claim 1, wherein X17 is Gln.

6. The GLP-2 analogue according to claim 1, wherein X17 is Lys.

7. The GLP-2 analogue according to claim 1, wherein X17 is Glu.

8. The GLP-2 analogue according to claim 1, wherein X14 is Leu.

9. The GLP-2 analogue according to claim 1, wherein X14 is Met.

10. The GLP-2 analogue according to claim 1, wherein:
   (i) X16 is Gly and X17 is Gln;
   (ii) X16 is Gly and X17 is Lys; or
   (iii) X16 is Gly and X17 is Glu.

11. The GLP-2 analogue according to claim 1, wherein X2 is Aib.

12. The GLP-2 analogue according to claim 1, wherein X19 is Ala.

13. The GLP-2 analogue according to claim 1, wherein X19 is Val.

14. A GLP-2 analogue represented by the general Formula II:

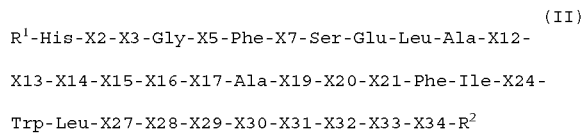

R$^1$-His-X2-X3-Gly-X5-Phe-X7-Ser-Glu-Leu-Ala-X12-X13-X14-X15-X16-X17-Ala-X19-X20-X21-Phe-Ile-X24-Trp-Leu-X27-X28-X29-X30-X31-X32-X33-X34-R$^2$ (II)

or a pharmaceutically acceptable salt thereof, wherein: R$^1$ is hydrogen, C$_{1-4}$ alkyl, acetyl, formyl, or benzoyl;
X2 is Gly, Ala or Aib;
X3 is Glu, Gln or Asp; X5 is Ser or Thr;
X7 is Ser or Thr;
X12 is Thr, Ser or Lys;
X13 is Ile, Leu, Val, Tyr, Phe or Gln;
X14 is Leu or Met;
X15 is Asp or Glu;
X16 is Gly, Ser, Ala, Glu or Lys; X17 is Gln or Lys;
X19 is Ala or Val;
X20 is Arg, Lys or His; X21 is Asp, Glu or Leu;
X24 is Asn, Ala, Glu or Lys; X27 is Ile, Leu, Val, Glu or Lys:
X28 is Gln, Asn, Lys, Ser, Y1 or absent; X29 Is Thr, Ala, Y1 or absent;
X30 is Lys, Y1 or absent; X31 is Ile, Pro, Y1 or absent; X32 is Thr, Y1 or absent;
X33 is Asp, Asn, Y1 or absent;
X34 is Y1 or absent;
Y1 is Gly-Gly-Pro-Ser-Ser-Gly-Ala-Pro-Pro-Pro-Ser, or Lys-Asn-Gry-Gly-Pro-Ser-Ser-Gly-Ala-Pro-Pro-Pro-Ser; and
R$^2$ is NH$_2$ or OH; wherein
the GLP-2 analogue contains no more than one Y1;
if any of X28 to X33 is Y1, those positions X29 to X34 downstream of that Y1 are absent;
if any of X28 to X33 is absent, those positions X29 to X33 downstream of that position are also absent.

15. The GLP-2 analogue according to claim 14, wherein X16 of Formula II is Gly, Ser or Ala.

16. A GLP-2 analogue according to claim 14 wherein:
R$^1$ is hydrogen, C$_{1-4}$ alkyl (e.g. methyl), acetyl, formyl, or benzoyl;
X2 is Gly or Aib;
X3 is Glu or Asp; X5 is Ser or Thr; X7 is Ser or Thr;
X12 is Thr, Ser or Lys;
X13 is Ile, Leu, Val, Tyr, Phe or Gln;
X14 is Leu or Met;
X15 is Asp or Glu;
X16 is Gly, Ser or Ala;
X17 is Gln or Lys;
X19 is Ala or Val;
X20 is Arg, Lys or His; X21 is Asp, Glu or Leu;
X24 is Asn, Ala, Glu or Lys;
X27 is Ile, Leu, Val, Glu or Lys:
X28 is Gln, Asn, Lys, Ser, Y1 or absent;
X29 is Thr, Ala, Y1 or absent;
X30 is Lys, Y1 or absent;
X31 is Ile, Pro, Y1 or absent;
X32 is Thr, Y1 or absent;
X33 is Asp, Asn, Y1 or absent;
X34 is Y1 or absent;
Y1 is Gly-Gly-Pro-Ser-Ser-Gly-Ala-Pro-Pro-Pro-Ser, or Lys-Asn-Gly-Gly-Pro-Ser-Ser-Gly-Ala-Pro-Pro-Pro-Ser; and
R$^2$ is NH$_2$ or OH; wherein
the GLP-2 analogue contains no more than one Y1;
if any of X28 to X33 is Y1, those positions X29 to X34 downstream of that Y1 are absent;
if any of X28 to X33 is absent, those positions X29 to X33 downstream of that position are also absent.

17. A GLP-2 analogue according to claim 14, wherein:
   (i) X16 is Gly and X17 Is Gln; or
   (ii) X16 is Gly and X17 is Lys.

18. A GLP-2 analogue according to claim 14, wherein:
   (i) X2 is Gly; or
   (ii) X2 is Aib.

19. A GLP-2 analogue represented by the general Formula III:

R$^1$-His-Gly-X3-Gly-X5-Phe-X7-Ser-Glu-Leu-Ala-X12-X13-Leu-X15-Gly-X17-Ala-X19-X20-X21-Phe-Ile-X24-Trp-Leu-X27-X28-X29-X30-X31-X32-X33-X34-R$^2$ (III)

or a pharmaceutically acceptable salt thereof, wherein: R$^1$ is hydrogen, C$_{1-4}$ alkyl, acetyl, formyl, or benzoyl;
X3 is Glu or Asp;
X5 is Ser or Thr;
X7 is Ser or Thr;
X12 is Thr, Ser or Lys;
X13 is Ile, Tyr, or Gln;
X15 is Asp or Glu;
X17 is Gln or Lys;
X19 is Ala or Val;
X20 is Arg, Lys or His;
X21 is Asp, Glu or Leu;
X24 is Asn, Ala, Glu;
X27 is Ile, Leu, Glu or Lys:
X28 is Gln, Lys, Ser, Gly, Y1 or absent;
X29 is Thr, Ala, Y1 or absent;
X30 is Lys, Y1 or absent;
X31 is Ile, Pro, Y1 or absent;
X32 is Thr, Y1 or absent;
X33 is Asp, Asn, Y1 or absent;
X34 is Y1 or absent;
Y1 is Gly-Gly-Pro-Ser-Ser-Gly-Ala-Pro-Pro-Pro-Ser, or Lys-Asn-Gly-Gly-Pro-Ser-Ser-Gly-Ala-Pro-Pro-Pro-Ser; and
R$^2$ is NH$_2$ or OH; wherein
the GLP-2 analogue contains no more than one Y1;
if any of X28 to X33 is Y1, those positions X29 to X34 downstream of that Y1 are absent;

if any of X28 to X33 is absent, those positions X29 to X33 downstream of that position are also absent.

20. The GLP-2 analogue claim 1, wherein the GLP-2 analogue is selected from the croup consisting of:

H-Aib-DGSFSDEMNTILDNQAARDFINWLIQTKITD; (SEQ ID NO: 8)

HGDGSFSDEMNTILDNKAARDFINWLIQTKITD; (SEQ ID NO: 9)

HGDGSFSDEMNTILDGQAARDFINWLIQTK; (SEQ ID NO: 10)

HGDGSFSSEMNTILDSQAARDFINWLIQTKITD; (SEQ ID NO: 11)

HGEGTFTSDLSKQMEGQAVRDFIEWLIQTKITD; (SEQ ID NO: 12)

HGEGTFTSDLSKQMESKAARDFIEWLIQTKITD; (SEQ ID NO: 13)

HGDGSFSSELATILDGKAARDFINWLIQTKITD; (SEQ ID NO: 14)

HGEGTFTSDLSTILENKAARDFIEWLIQTKITD; (SEQ ID NO: 15)

HGEGSFSSDLSTILENKAARDFIEWLIQTKITD; (SEQ ID NO: 16)

H-Aib-DGSFSDELNTILDGKAARDFINWLIQTK; (SEQ ID NO: 17)

HGDGSFSSELATILDGQAARDFIAWLIQTKITD; (SEQ ID NO: 18)

HGDGSFSDEMNTILDGQAARDFINWLIQTK; (SEQ ID NO: 19)
and

HGEGSFSSDLSTILEGKAARDFIEWLIQTKITD; (SEQ ID NO: 20)

or a pharmaceutically acceptable salt thereof.

21. The GLP-2 analogue claim 1, wherein a lipophilic substituent is conjugated to one or more of positions 12, 14, 16, 17, 19, 20, 24, 27, 28 and 32.

22. The GLP-2 analogue of claim 1, wherein the GLP-2 analogue is a pharmaceutically acceptable acid addition salt.

23. The GLP-2 analogue of claim 1, wherein $R^1$ is methyl.

24. The GLP-2 analogue of claim 3, wherein $R^1$ is methyl.

25. The GLP-2 analogue of claim 14, wherein $R^1$ is methyl.

26. The GLP-2 analogue of claim 19, wherein $R^1$ is methyl.

27. A pharmaceutical composition comprising a GLP-2 analogue of claim 1 in admixture with a carrier.

28. The pharmaceutical composition of claim 27, which is formulated as a liquid suitable for administration by injection or infusion, or which is formulated to cause slow release of said GLP-2 analogue.

29. A method of treating or preventing low grade inflammation, said method comprising administering a GLP-2 analogue of claim 1.

30. The method of claim 29, wherein said low grade inflammation is related to diabetes.

31. The method of claim 30, wherein the low grade inflammation related to diabetes is associated with a condition selected from the group consisting of metabolic syndrome; obesity; diabetes; cardiovascular diseases; gastrointestinal inflammation; depression; Alzheimer's disease; arthritis; hypertension; dyslipidemia; stroke; gastro-intestinal disorders in the upper gastrointestinal tract of the esophagus, the stomach, duodenum, the small intestine, colon and rectum; ulcers of any etiology; digestion disorders; malabsorption syndromes; short-bowel syndrome; cul-de-sac syndrome; inflammatory bowel disease; celiac sprue; tropical sprue; hypogammaglobulinemic sprue; and chemotherapy and/or radiation therapy induced mucositis, and diarrhea.

32. A method of treating a gastrointestinal related disorder in a patient in need thereof, said method comprising administering an effective amount of a GLP-2 analogue of claim 1.

33. The method of claim 32, wherein the gastrointestinal related disorder is low grade inflammation associated with a condition selected from the group consisting of metabolic syndrome; obesity; diabetes; cardiovascular diseases; gastrointestinal inflammation; depression; Alzheimer's disease; arthritis; hypertension; dyslipidemia; stroke; gastrointestinal disorders in the upper gastrointestinal tract of the esophagus, the stomach, duodenum, the small intestine, colon and rectum; ulcers of any etiology; digestion disorders; malabsorption syndromes; short-bowel syndrome; cul-de-sac syndrome; inflammatory bowel disease; celiac sprue; tropical sprue; hypogammaglobulinemic sprue; and chemotherapy and/or radiation therapy induced mucositis, and diarrhea.

34. The method of claim 31, wherein the type of obesity is abdominal obesity.

35. The method of claim 33, wherein the type of obesity is abdominal obesity.

* * * * *

SEQUENCE LISTING

```
<160> NUMBER OF SEQ ID NOS: 27

<210> SEQ ID NO 1
<211> LENGTH: 33
<212> TYPE: PRT
<213> ORGANISM: Homo sapiens

<400> SEQUENCE: 1

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp
```

```
<210> SEQ ID NO 2
<211> LENGTH: 110
<212> TYPE: PRT
<213> ORGANISM: Artificial sequence
<220> FEATURE:
<223> OTHER INFORMATION: Synthetic sequence: GLP-2 analogue: General
      Formula I of PCT/EP2013/059320
<220> FEATURE:
<221> NAME/KEY: VARIANT
<222> LOCATION: (2)..(2)
<223> OTHER INFORMATION: Xaa is Gly, Ala or Aib
<220> FEATURE:
<221> NAME/KEY: VARIANT
<222> LOCATION: (3)..(3)
<223> OTHER INFORMATION: Xaa is Glu, Gln or Asp
<220> FEATURE:
<221> NAME/KEY: VARIANT
<222> LOCATION: (5)..(5)
<223> OTHER INFORMATION: Xaa is Ser or Thr
<220> FEATURE:
<221> NAME/KEY: VARIANT
<222> LOCATION: (7)..(7)
<223> OTHER INFORMATION: Xaa is Ser or Thr
<220> FEATURE:
<221> NAME/KEY: VARIANT
<222> LOCATION: (8)..(8)
<223> OTHER INFORMATION: Xaa is Asp, Glu or Ser
<220> FEATURE:
<221> NAME/KEY: VARIANT
<222> LOCATION: (9)..(9)
<223> OTHER INFORMATION: Xaa is Glu or Asp
<220> FEATURE:
<221> NAME/KEY: VARIANT
<222> LOCATION: (10)..(10)
<223> OTHER INFORMATION: Xaa is Met, Val, Leu or Tyr
<220> FEATURE:
<221> NAME/KEY: VARIANT
<222> LOCATION: (11)..(11)
<223> OTHER INFORMATION: Xaa is Asn, Ser or Ala
<220> FEATURE:
<221> NAME/KEY: VARIANT
<222> LOCATION: (12)..(12)
<223> OTHER INFORMATION: Xaa is Thr, Ser or Lys
<220> FEATURE:
<221> NAME/KEY: VARIANT
<222> LOCATION: (13)..(13)
<223> OTHER INFORMATION: Xaa is Ile, Leu, Val, Tyr, Phe or Gln
<220> FEATURE:
<221> NAME/KEY: VARIANT
<222> LOCATION: (14)..(14)
<223> OTHER INFORMATION: Xaa is Leu or Met
<220> FEATURE:
<221> NAME/KEY: VARIANT
<222> LOCATION: (15)..(15)
<223> OTHER INFORMATION: Xaa is Asp or Glu
<220> FEATURE:
<221> NAME/KEY: VARIANT
<222> LOCATION: (16)..(16)
<223> OTHER INFORMATION: Xaa is Asn, Gln, Gly, Ser, Ala, Glu or Lys
<220> FEATURE:
<221> NAME/KEY: VARIANT
<222> LOCATION: (17)..(17)
<223> OTHER INFORMATION: Xaa is Gln, Lys, Arg, His or Glu
<220> FEATURE:
<221> NAME/KEY: VARIANT
<222> LOCATION: (19)..(19)
<223> OTHER INFORMATION: Xaa is Ala or Val
<220> FEATURE:
<221> NAME/KEY: VARIANT
<222> LOCATION: (20)..(20)
<223> OTHER INFORMATION: Xaa is Arg, Lys or His
<220> FEATURE:
<221> NAME/KEY: VARIANT
<222> LOCATION: (21)..(21)
<223> OTHER INFORMATION: Xaa is Asp, Glu or Leu
<220> FEATURE:
<221> NAME/KEY: VARIANT
<222> LOCATION: (24)..(24)
<223> OTHER INFORMATION: Xaa is Asn, Ala, Glu or Lys
```

```
<220> FEATURE:
<221> NAME/KEY: VARIANT
<222> LOCATION: (27)..(27)
<223> OTHER INFORMATION: Xaa is Ile, Leu, Val, Glu or Lys
<220> FEATURE:
<221> NAME/KEY: VARIANT
<222> LOCATION: (28)..(28)
<223> OTHER INFORMATION: Xaa is Gln, Asn, Lys, Ser, Gly, or absent.
<220> FEATURE:
<221> NAME/KEY: VARIANT
<222> LOCATION: (28)..(39)
<223> OTHER INFORMATION: If Xaa at position 28 is any of the amino acids
      listed (as in, the position is not absent), then the Xaa's from
      positions 29-39 are absent; if Xaa at position 28 is absent, then
      the Xaa's from positions 29-39 are not absent.
<220> FEATURE:
<221> NAME/KEY: VARIANT
<222> LOCATION: (29)..(29)
<223> OTHER INFORMATION: Xaa is Gly or absent
<220> FEATURE:
<221> NAME/KEY: VARIANT
<222> LOCATION: (30)..(30)
<223> OTHER INFORMATION: Xaa is Gly or absent
<220> FEATURE:
<221> NAME/KEY: VARIANT
<222> LOCATION: (31)..(31)
<223> OTHER INFORMATION: Xaa is Pro or absent
<220> FEATURE:
<221> NAME/KEY: VARIANT
<222> LOCATION: (32)..(32)
<223> OTHER INFORMATION: Xaa is Ser or absent
<220> FEATURE:
<221> NAME/KEY: VARIANT
<222> LOCATION: (33)..(33)
<223> OTHER INFORMATION: Xaa is Ser or absent
<220> FEATURE:
<221> NAME/KEY: VARIANT
<222> LOCATION: (34)..(34)
<223> OTHER INFORMATION: Xaa is Gly or absent
<220> FEATURE:
<221> NAME/KEY: VARIANT
<222> LOCATION: (35)..(35)
<223> OTHER INFORMATION: Xaa is Ala or absent
<220> FEATURE:
<221> NAME/KEY: VARIANT
<222> LOCATION: (36)..(36)
<223> OTHER INFORMATION: Xaa is Pro or absent
<220> FEATURE:
<221> NAME/KEY: VARIANT
<222> LOCATION: (37)..(37)
<223> OTHER INFORMATION: Xaa is Pro or absent
<220> FEATURE:
<221> NAME/KEY: VARIANT
<222> LOCATION: (38)..(38)
<223> OTHER INFORMATION: Xaa is Pro or absent
<220> FEATURE:
<221> NAME/KEY: VARIANT
<222> LOCATION: (39)..(39)
<223> OTHER INFORMATION: Xaa is Ser or absent
<220> FEATURE:
<221> NAME/KEY: VARIANT
<222> LOCATION: (40)..(40)
<223> OTHER INFORMATION: Xaa is Thr, Ala, or absent.
<220> FEATURE:
<221> NAME/KEY: VARIANT
<222> LOCATION: (40)..(51)
<223> OTHER INFORMATION: If Xaa at position 40 is any of the amino acids
      listed (as in, the position is not absent), then the Xaa's from
      positions 41-51 are absent; if Xaa at position 40 is absent, then
      the Xaa's from positions 41-51 are not absent.
<220> FEATURE:
<221> NAME/KEY: VARIANT
<222> LOCATION: (41)..(41)
<223> OTHER INFORMATION: Xaa is Gly or absent
<220> FEATURE:
<221> NAME/KEY: VARIANT
<222> LOCATION: (42)..(42)
<223> OTHER INFORMATION: Xaa is Gly or absent
<220> FEATURE:
```

```
<221> NAME/KEY: VARIANT
<222> LOCATION: (43)..(43)
<223> OTHER INFORMATION: Xaa is Pro or absent
<220> FEATURE:
<221> NAME/KEY: VARIANT
<222> LOCATION: (44)..(44)
<223> OTHER INFORMATION: Xaa is Ser or absent
<220> FEATURE:
<221> NAME/KEY: VARIANT
<222> LOCATION: (45)..(45)
<223> OTHER INFORMATION: Xaa is Ser or absent
<220> FEATURE:
<221> NAME/KEY: VARIANT
<222> LOCATION: (46)..(46)
<223> OTHER INFORMATION: Xaa is Gly or absent
<220> FEATURE:
<221> NAME/KEY: VARIANT
<222> LOCATION: (47)..(47)
<223> OTHER INFORMATION: Xaa is Ala or absent
<220> FEATURE:
<221> NAME/KEY: VARIANT
<222> LOCATION: (48)..(48)
<223> OTHER INFORMATION: Xaa is Pro or absent
<220> FEATURE:
<221> NAME/KEY: VARIANT
<222> LOCATION: (49)..(49)
<223> OTHER INFORMATION: Xaa is Pro or absent
<220> FEATURE:
<221> NAME/KEY: VARIANT
<222> LOCATION: (50)..(50)
<223> OTHER INFORMATION: Xaa is Pro or absent
<220> FEATURE:
<221> NAME/KEY: VARIANT
<222> LOCATION: (51)..(51)
<223> OTHER INFORMATION: Xaa is Ser or absent
<220> FEATURE:
<221> NAME/KEY: VARIANT
<222> LOCATION: (52)..(52)
<223> OTHER INFORMATION: Xaa is Lys or absent.
<220> FEATURE:
<221> NAME/KEY: VARIANT
<222> LOCATION: (52)..(63)
<223> OTHER INFORMATION: If Xaa at position 52 is any of the amino acids
      listed (as in, the position is not absent), then the Xaa's from
      positions 53-63 are absent; if Xaa at position 52 is absent, then
      the Xaa's from positions 53-63 are not absent.
<220> FEATURE:
<221> NAME/KEY: VARIANT
<222> LOCATION: (53)..(53)
<223> OTHER INFORMATION: Xaa is Gly or absent
<220> FEATURE:
<221> NAME/KEY: VARIANT
<222> LOCATION: (54)..(54)
<223> OTHER INFORMATION: Xaa is Gly or absent
<220> FEATURE:
<221> NAME/KEY: VARIANT
<222> LOCATION: (55)..(55)
<223> OTHER INFORMATION: Xaa is Pro or absent
<220> FEATURE:
<221> NAME/KEY: VARIANT
<222> LOCATION: (56)..(56)
<223> OTHER INFORMATION: Xaa is Ser or absent
<220> FEATURE:
<221> NAME/KEY: VARIANT
<222> LOCATION: (57)..(57)
<223> OTHER INFORMATION: Xaa is Ser or absent
<220> FEATURE:
<221> NAME/KEY: VARIANT
<222> LOCATION: (58)..(58)
<223> OTHER INFORMATION: Xaa is Gly or absent
<220> FEATURE:
<221> NAME/KEY: VARIANT
<222> LOCATION: (59)..(59)
<223> OTHER INFORMATION: Xaa is Ala or absent
<220> FEATURE:
<221> NAME/KEY: VARIANT
<222> LOCATION: (60)..(60)
<223> OTHER INFORMATION: Xaa is Pro or absent
<220> FEATURE:
```

```
<221> NAME/KEY: VARIANT
<222> LOCATION: (61)..(61)
<223> OTHER INFORMATION: Xaa is Pro or absent
<220> FEATURE:
<221> NAME/KEY: VARIANT
<222> LOCATION: (62)..(62)
<223> OTHER INFORMATION: Xaa is Pro or absent
<220> FEATURE:
<221> NAME/KEY: VARIANT
<222> LOCATION: (63)..(63)
<223> OTHER INFORMATION: Xaa is Ser or absent
<220> FEATURE:
<221> NAME/KEY: VARIANT
<222> LOCATION: (64)..(64)
<223> OTHER INFORMATION: Xaa is Ile, Pro, or absent.
<220> FEATURE:
<221> NAME/KEY: VARIANT
<222> LOCATION: (64)..(75)
<223> OTHER INFORMATION: If Xaa at position 64 is any of the amino acids
      listed (as in, the position is not absent), then the Xaa's from
      positions 65-75 are absent; if Xaa at position 64 is absent, then
      the Xaa's from positions 65-75 are not absent.
<220> FEATURE:
<221> NAME/KEY: VARIANT
<222> LOCATION: (65)..(65)
<223> OTHER INFORMATION: Xaa is Gly or absent
<220> FEATURE:
<221> NAME/KEY: VARIANT
<222> LOCATION: (66)..(66)
<223> OTHER INFORMATION: Xaa is Gly or absent
<220> FEATURE:
<221> NAME/KEY: VARIANT
<222> LOCATION: (67)..(67)
<223> OTHER INFORMATION: Xaa is Pro or absent
<220> FEATURE:
<221> NAME/KEY: VARIANT
<222> LOCATION: (68)..(68)
<223> OTHER INFORMATION: Xaa is Ser or absent
<220> FEATURE:
<221> NAME/KEY: VARIANT
<222> LOCATION: (69)..(69)
<223> OTHER INFORMATION: Xaa is Ser or absent
<220> FEATURE:
<221> NAME/KEY: VARIANT
<222> LOCATION: (70)..(70)
<223> OTHER INFORMATION: Xaa is Gly or absent
<220> FEATURE:
<221> NAME/KEY: VARIANT
<222> LOCATION: (71)..(71)
<223> OTHER INFORMATION: Xaa is Ala or absent
<220> FEATURE:
<221> NAME/KEY: VARIANT
<222> LOCATION: (72)..(72)
<223> OTHER INFORMATION: Xaa is Pro or absent
<220> FEATURE:
<221> NAME/KEY: VARIANT
<222> LOCATION: (73)..(73)
<223> OTHER INFORMATION: Xaa is Pro or absent
<220> FEATURE:
<221> NAME/KEY: VARIANT
<222> LOCATION: (74)..(74)
<223> OTHER INFORMATION: Xaa is Pro or absent
<220> FEATURE:
<221> NAME/KEY: VARIANT
<222> LOCATION: (75)..(75)
<223> OTHER INFORMATION: Xaa is Ser or absent
<220> FEATURE:
<221> NAME/KEY: VARIANT
<222> LOCATION: (76)..(76)
<223> OTHER INFORMATION: Xaa is Thr or absent.
<220> FEATURE:
<221> NAME/KEY: VARIANT
<222> LOCATION: (76)..(87)
<223> OTHER INFORMATION: If Xaa at position 76 is any of the amino acids
      listed (as in, the position is not absent), then the Xaa's from
      positions 77-87 are absent; if Xaa at position 76 is absent, then
      the Xaa's from positions 77-87 are not absent.
<220> FEATURE:
<221> NAME/KEY: VARIANT
```

```
<222> LOCATION: (77)..(77)
<223> OTHER INFORMATION: Xaa is Gly or absent
<220> FEATURE:
<221> NAME/KEY: VARIANT
<222> LOCATION: (78)..(78)
<223> OTHER INFORMATION: Xaa is Gly or absent
<220> FEATURE:
<221> NAME/KEY: VARIANT
<222> LOCATION: (79)..(79)
<223> OTHER INFORMATION: Xaa is Pro or absent
<220> FEATURE:
<221> NAME/KEY: VARIANT
<222> LOCATION: (80)..(80)
<223> OTHER INFORMATION: Xaa is Ser or absent
<220> FEATURE:
<221> NAME/KEY: VARIANT
<222> LOCATION: (81)..(81)
<223> OTHER INFORMATION: Xaa is Ser or absent
<220> FEATURE:
<221> NAME/KEY: VARIANT
<222> LOCATION: (82)..(82)
<223> OTHER INFORMATION: Xaa is Gly or absent
<220> FEATURE:
<221> NAME/KEY: VARIANT
<222> LOCATION: (83)..(83)
<223> OTHER INFORMATION: Xaa is Ala or absent
<220> FEATURE:
<221> NAME/KEY: VARIANT
<222> LOCATION: (84)..(84)
<223> OTHER INFORMATION: Xaa is Pro or absent
<220> FEATURE:
<221> NAME/KEY: VARIANT
<222> LOCATION: (85)..(85)
<223> OTHER INFORMATION: Xaa is Pro or absent
<220> FEATURE:
<221> NAME/KEY: VARIANT
<222> LOCATION: (86)..(86)
<223> OTHER INFORMATION: Xaa is Pro or absent
<220> FEATURE:
<221> NAME/KEY: VARIANT
<222> LOCATION: (87)..(87)
<223> OTHER INFORMATION: Xaa is Ser or absent
<220> FEATURE:
<221> NAME/KEY: VARIANT
<222> LOCATION: (88)..(88)
<223> OTHER INFORMATION: Xaa is Asp, Asn, or absent.
<220> FEATURE:
<221> NAME/KEY: VARIANT
<222> LOCATION: (88)..(99)
<223> OTHER INFORMATION: If Xaa at position 88 is any of the amino acids
      listed (as in, the position is not absent), then the Xaa's from
      positions 89-99 are absent; if Xaa at position 88 is absent, then
      the Xaa's from positions 89-99 are not absent.
<220> FEATURE:
<221> NAME/KEY: VARIANT
<222> LOCATION: (89)..(89)
<223> OTHER INFORMATION: Xaa is Gly or absent
<220> FEATURE:
<221> NAME/KEY: VARIANT
<222> LOCATION: (90)..(90)
<223> OTHER INFORMATION: Xaa is Gly or absent
<220> FEATURE:
<221> NAME/KEY: VARIANT
<222> LOCATION: (91)..(91)
<223> OTHER INFORMATION: Xaa is Pro or absent
<220> FEATURE:
<221> NAME/KEY: VARIANT
<222> LOCATION: (92)..(92)
<223> OTHER INFORMATION: Xaa is Ser or absent
<220> FEATURE:
<221> NAME/KEY: VARIANT
<222> LOCATION: (93)..(93)
<223> OTHER INFORMATION: Xaa is Ser or absent
<220> FEATURE:
<221> NAME/KEY: VARIANT
<222> LOCATION: (94)..(94)
<223> OTHER INFORMATION: Xaa is Gly or absent
<220> FEATURE:
<221> NAME/KEY: VARIANT
```

```
<222> LOCATION: (95)..(95)
<223> OTHER INFORMATION: Xaa is Ala or absent
<220> FEATURE:
<221> NAME/KEY: VARIANT
<222> LOCATION: (96)..(96)
<223> OTHER INFORMATION: Xaa is Pro or absent
<220> FEATURE:
<221> NAME/KEY: VARIANT
<222> LOCATION: (97)..(97)
<223> OTHER INFORMATION: Xaa is Pro or absent
<220> FEATURE:
<221> NAME/KEY: VARIANT
<222> LOCATION: (98)..(98)
<223> OTHER INFORMATION: Xaa is Pro or absent
<220> FEATURE:
<221> NAME/KEY: VARIANT
<222> LOCATION: (99)..(99)
<223> OTHER INFORMATION: Xaa is Ser or absent
<220> FEATURE:
<221> NAME/KEY: VARIANT
<222> LOCATION: (100)..(100)
<223> OTHER INFORMATION: Xaa is Gly or absent
<220> FEATURE:
<221> NAME/KEY: VARIANT
<222> LOCATION: (100)..(110)
<223> OTHER INFORMATION: If Xaa at position 100 is absent, then Xaa's
      from positions 101-110 are also absent; if Xaa at position 100 is
      not absent, then Xaa's from positions 101-110 are also not absent.
<220> FEATURE:
<221> NAME/KEY: VARIANT
<222> LOCATION: (101)..(101)
<223> OTHER INFORMATION: Xaa is Gly or absent
<220> FEATURE:
<221> NAME/KEY: VARIANT
<222> LOCATION: (102)..(102)
<223> OTHER INFORMATION: Xaa is Pro or absent
<220> FEATURE:
<221> NAME/KEY: VARIANT
<222> LOCATION: (103)..(103)
<223> OTHER INFORMATION: Xaa is Ser or absent
<220> FEATURE:
<221> NAME/KEY: VARIANT
<222> LOCATION: (104)..(104)
<223> OTHER INFORMATION: Xaa is Ser or absent
<220> FEATURE:
<221> NAME/KEY: VARIANT
<222> LOCATION: (105)..(105)
<223> OTHER INFORMATION: Xaa is Gly or absent
<220> FEATURE:
<221> NAME/KEY: VARIANT
<222> LOCATION: (106)..(106)
<223> OTHER INFORMATION: Xaa is Ala or absent
<220> FEATURE:
<221> NAME/KEY: VARIANT
<222> LOCATION: (107)..(107)
<223> OTHER INFORMATION: Xaa is Pro or absent
<220> FEATURE:
<221> NAME/KEY: VARIANT
<222> LOCATION: (108)..(108)
<223> OTHER INFORMATION: Xaa is Pro or absent
<220> FEATURE:
<221> NAME/KEY: VARIANT
<222> LOCATION: (109)..(109)
<223> OTHER INFORMATION: Xaa is Pro or absent
<220> FEATURE:
<221> NAME/KEY: VARIANT
<222> LOCATION: (110)..(110)
<223> OTHER INFORMATION: Xaa is Ser or absent

<400> SEQUENCE: 2

His Xaa Xaa Gly Xaa Phe Xaa Xaa Xaa Xaa Xaa Xaa Xaa Xaa Xaa
1               5                   10                  15

Xaa Ala Xaa Xaa Xaa Phe Ile Xaa Trp Leu Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45
```

```
Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa
            100                 105                 110

<210> SEQ ID NO 3
<211> LENGTH: 124
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (2)..(2)
<223> OTHER INFORMATION: Xaa is Gly, Ala or Aib
<220> FEATURE:
<221> NAME/KEY: VARIANT
<222> LOCATION: (3)..(3)
<223> OTHER INFORMATION: Xaa is Glu, Gln or Asp
<220> FEATURE:
<221> NAME/KEY: VARIANT
<222> LOCATION: (5)..(5)
<223> OTHER INFORMATION: Xaa is Ser or Thr
<220> FEATURE:
<221> NAME/KEY: VARIANT
<222> LOCATION: (7)..(7)
<223> OTHER INFORMATION: Xaa is Ser or Thr
<220> FEATURE:
<221> NAME/KEY: VARIANT
<222> LOCATION: (8)..(8)
<223> OTHER INFORMATION: Xaa is Asp, Glu or Ser
<220> FEATURE:
<221> NAME/KEY: VARIANT
<222> LOCATION: (9)..(9)
<223> OTHER INFORMATION: Xaa is Glu or Asp
<220> FEATURE:
<221> NAME/KEY: VARIANT
<222> LOCATION: (10)..(10)
<223> OTHER INFORMATION: Xaa is Met, Val, Leu or Tyr
<220> FEATURE:
<221> NAME/KEY: VARIANT
<222> LOCATION: (11)..(11)
<223> OTHER INFORMATION: Xaa is Asn, Ser or Ala
<220> FEATURE:
<221> NAME/KEY: VARIANT
<222> LOCATION: (12)..(12)
<223> OTHER INFORMATION: Xaa is Thr, Ser or Lys
<220> FEATURE:
<221> NAME/KEY: VARIANT
<222> LOCATION: (13)..(13)
<223> OTHER INFORMATION: Xaa is Ile, Leu, Val, Tyr, Phe or Gln
<220> FEATURE:
<221> NAME/KEY: VARIANT
<222> LOCATION: (14)..(14)
<223> OTHER INFORMATION: Xaa is Leu or Met
<220> FEATURE:
<221> NAME/KEY: VARIANT
<222> LOCATION: (15)..(15)
<223> OTHER INFORMATION: Xaa is Asp or Glu
<220> FEATURE:
<221> NAME/KEY: VARIANT
<222> LOCATION: (16)..(16)
<223> OTHER INFORMATION: Xaa is Asn, Gln, Gly, Ser, Ala, Glu or Lys
<220> FEATURE:
<221> NAME/KEY: VARIANT
<222> LOCATION: (17)..(17)
<223> OTHER INFORMATION: Xaa is Gln, Lys, Arg, His or Glu
<220> FEATURE:
<221> NAME/KEY: VARIANT
<222> LOCATION: (19)..(19)
```

```
<223> OTHER INFORMATION: Xaa is Ala or Val
<220> FEATURE:
<221> NAME/KEY: VARIANT
<222> LOCATION: (20)..(20)
<223> OTHER INFORMATION: Xaa is Arg, Lys or His
<220> FEATURE:
<221> NAME/KEY: VARIANT
<222> LOCATION: (21)..(21)
<223> OTHER INFORMATION: Xaa is Asp, Glu or Leu
<220> FEATURE:
<221> NAME/KEY: VARIANT
<222> LOCATION: (24)..(24)
<223> OTHER INFORMATION: Xaa is Asn, Ala, Glu or Lys
<220> FEATURE:
<221> NAME/KEY: VARIANT
<222> LOCATION: (27)..(27)
<223> OTHER INFORMATION: Xaa is Ile, Leu, Val, Glu or Lys
<220> FEATURE:
<221> NAME/KEY: VARIANT
<222> LOCATION: (28)..(28)
<223> OTHER INFORMATION: Xaa is Gln, Asn, Lys, Ser, Gly, or absent.
<220> FEATURE:
<221> NAME/KEY: VARIANT
<222> LOCATION: (28)..(41)
<223> OTHER INFORMATION: If Xaa at position 28 is any of the amino acids
      listed (as in, the position is not absent), then the Xaa's from
      positions 29-41 are absent; if Xaa at position 28 is absent, then
      the Xaa's from positions 29-41 are not absent.
<220> FEATURE:
<221> NAME/KEY: VARIANT
<222> LOCATION: (29)..(29)
<223> OTHER INFORMATION: Xaa is Lys or absent
<220> FEATURE:
<221> NAME/KEY: VARIANT
<222> LOCATION: (30)..(30)
<223> OTHER INFORMATION: Xaa is Asn or absent
<220> FEATURE:
<221> NAME/KEY: VARIANT
<222> LOCATION: (31)..(31)
<223> OTHER INFORMATION: Xaa is Gly or absent
<220> FEATURE:
<221> NAME/KEY: VARIANT
<222> LOCATION: (32)..(32)
<223> OTHER INFORMATION: Xaa is Gly or absent
<220> FEATURE:
<221> NAME/KEY: VARIANT
<222> LOCATION: (33)..(33)
<223> OTHER INFORMATION: Xaa is Pro or absent
<220> FEATURE:
<221> NAME/KEY: VARIANT
<222> LOCATION: (34)..(34)
<223> OTHER INFORMATION: Xaa is Ser or absent
<220> FEATURE:
<221> NAME/KEY: VARIANT
<222> LOCATION: (35)..(35)
<223> OTHER INFORMATION: Xaa is Ser or absent
<220> FEATURE:
<221> NAME/KEY: VARIANT
<222> LOCATION: (36)..(36)
<223> OTHER INFORMATION: Xaa is Gly or absent
<220> FEATURE:
<221> NAME/KEY: VARIANT
<222> LOCATION: (37)..(37)
<223> OTHER INFORMATION: Xaa is Ala or absent
<220> FEATURE:
<221> NAME/KEY: VARIANT
<222> LOCATION: (38)..(38)
<223> OTHER INFORMATION: Xaa is Pro or absent
<220> FEATURE:
<221> NAME/KEY: VARIANT
<222> LOCATION: (39)..(39)
<223> OTHER INFORMATION: Xaa is Pro or absent
<220> FEATURE:
<221> NAME/KEY: VARIANT
<222> LOCATION: (40)..(40)
<223> OTHER INFORMATION: Xaa is Pro or absent
<220> FEATURE:
<221> NAME/KEY: VARIANT
<222> LOCATION: (41)..(41)
```

```
<223> OTHER INFORMATION: Xaa is Ser or absent
<220> FEATURE:
<221> NAME/KEY: VARIANT
<222> LOCATION: (42)..(42)
<223> OTHER INFORMATION: Xaa is Thr, Ala, or absent.
<220> FEATURE:
<221> NAME/KEY: VARIANT
<222> LOCATION: (42)..(55)
<223> OTHER INFORMATION: If Xaa at position 42 is any of the amino acids
      listed (as in, the position is not absent), then the Xaa's from
      positions 43-55 are absent; if Xaa at position 42 is absent, then
      the Xaa's from positions 43-55 are not absent.
<220> FEATURE:
<221> NAME/KEY: VARIANT
<222> LOCATION: (43)..(43)
<223> OTHER INFORMATION: Xaa is Lys or absent
<220> FEATURE:
<221> NAME/KEY: VARIANT
<222> LOCATION: (44)..(44)
<223> OTHER INFORMATION: Xaa is Asn or absent
<220> FEATURE:
<221> NAME/KEY: VARIANT
<222> LOCATION: (45)..(45)
<223> OTHER INFORMATION: Xaa is Gly or absent
<220> FEATURE:
<221> NAME/KEY: VARIANT
<222> LOCATION: (46)..(46)
<223> OTHER INFORMATION: Xaa is Gly or absent
<220> FEATURE:
<221> NAME/KEY: VARIANT
<222> LOCATION: (47)..(47)
<223> OTHER INFORMATION: Xaa is Pro or absent
<220> FEATURE:
<221> NAME/KEY: VARIANT
<222> LOCATION: (48)..(48)
<223> OTHER INFORMATION: Xaa is Ser or absent
<220> FEATURE:
<221> NAME/KEY: VARIANT
<222> LOCATION: (49)..(49)
<223> OTHER INFORMATION: Xaa is Ser or absent
<220> FEATURE:
<221> NAME/KEY: VARIANT
<222> LOCATION: (50)..(50)
<223> OTHER INFORMATION: Xaa is Gly or absent
<220> FEATURE:
<221> NAME/KEY: VARIANT
<222> LOCATION: (51)..(51)
<223> OTHER INFORMATION: Xaa is Ala or absent
<220> FEATURE:
<221> NAME/KEY: VARIANT
<222> LOCATION: (52)..(52)
<223> OTHER INFORMATION: Xaa is Pro or absent
<220> FEATURE:
<221> NAME/KEY: VARIANT
<222> LOCATION: (53)..(53)
<223> OTHER INFORMATION: Xaa is Pro or absent
<220> FEATURE:
<221> NAME/KEY: VARIANT
<222> LOCATION: (54)..(54)
<223> OTHER INFORMATION: Xaa is Pro or absent
<220> FEATURE:
<221> NAME/KEY: VARIANT
<222> LOCATION: (55)..(55)
<223> OTHER INFORMATION: Xaa is Ser or absent
<220> FEATURE:
<221> NAME/KEY: VARIANT
<222> LOCATION: (56)..(56)
<223> OTHER INFORMATION: Xaa is Lys or absent.
<220> FEATURE:
<221> NAME/KEY: VARIANT
<222> LOCATION: (56)..(69)
<223> OTHER INFORMATION: If Xaa at position 56 is any of the amino acids
      listed (as in, the position is not absent), then the Xaa's from
      positions 57-69 are absent; if Xaa at position 56 is absent, then
      the Xaa's from positions 57-69 are not absent.
<220> FEATURE:
<221> NAME/KEY: VARIANT
<222> LOCATION: (57)..(57)
<223> OTHER INFORMATION: Xaa is Lys or absent
```

```
<220> FEATURE:
<221> NAME/KEY: VARIANT
<222> LOCATION: (58)..(58)
<223> OTHER INFORMATION: Xaa is Asn or absent
<220> FEATURE:
<221> NAME/KEY: VARIANT
<222> LOCATION: (59)..(59)
<223> OTHER INFORMATION: Xaa is Gly or absent
<220> FEATURE:
<221> NAME/KEY: VARIANT
<222> LOCATION: (60)..(60)
<223> OTHER INFORMATION: Xaa is Gly or absent
<220> FEATURE:
<221> NAME/KEY: VARIANT
<222> LOCATION: (61)..(61)
<223> OTHER INFORMATION: Xaa is Pro or absent
<220> FEATURE:
<221> NAME/KEY: VARIANT
<222> LOCATION: (62)..(62)
<223> OTHER INFORMATION: Xaa is Ser or absent
<220> FEATURE:
<221> NAME/KEY: VARIANT
<222> LOCATION: (63)..(63)
<223> OTHER INFORMATION: Xaa is Ser or absent
<220> FEATURE:
<221> NAME/KEY: VARIANT
<222> LOCATION: (64)..(64)
<223> OTHER INFORMATION: Xaa is Gly or absent
<220> FEATURE:
<221> NAME/KEY: VARIANT
<222> LOCATION: (65)..(65)
<223> OTHER INFORMATION: Xaa is Ala or absent
<220> FEATURE:
<221> NAME/KEY: VARIANT
<222> LOCATION: (66)..(66)
<223> OTHER INFORMATION: Xaa is Pro or absent
<220> FEATURE:
<221> NAME/KEY: VARIANT
<222> LOCATION: (67)..(67)
<223> OTHER INFORMATION: Xaa is Pro or absent
<220> FEATURE:
<221> NAME/KEY: VARIANT
<222> LOCATION: (68)..(68)
<223> OTHER INFORMATION: Xaa is Pro or absent
<220> FEATURE:
<221> NAME/KEY: VARIANT
<222> LOCATION: (69)..(69)
<223> OTHER INFORMATION: Xaa is Ser or absent
<220> FEATURE:
<221> NAME/KEY: VARIANT
<222> LOCATION: (70)..(70)
<223> OTHER INFORMATION: Xaa is Ile, Pro, or absent.
<220> FEATURE:
<221> NAME/KEY: VARIANT
<222> LOCATION: (70)..(83)
<223> OTHER INFORMATION: If Xaa at position 70 is any of the amino acids
      listed (as in, the position is not absent), then the Xaa's from
      positions 71-83 are absent; if Xaa at position 70 is absent, then
      the Xaa's from positions 71-83 are not absent.
<220> FEATURE:
<221> NAME/KEY: VARIANT
<222> LOCATION: (71)..(71)
<223> OTHER INFORMATION: Xaa is Lys or absent
<220> FEATURE:
<221> NAME/KEY: VARIANT
<222> LOCATION: (72)..(72)
<223> OTHER INFORMATION: Xaa is Asn or absent
<220> FEATURE:
<221> NAME/KEY: VARIANT
<222> LOCATION: (73)..(73)
<223> OTHER INFORMATION: Xaa is Gly or absent
<220> FEATURE:
<221> NAME/KEY: VARIANT
<222> LOCATION: (74)..(74)
<223> OTHER INFORMATION: Xaa is Gly or absent
<220> FEATURE:
<221> NAME/KEY: VARIANT
<222> LOCATION: (75)..(75)
<223> OTHER INFORMATION: Xaa is Pro or absent
```

```
<220> FEATURE:
<221> NAME/KEY: VARIANT
<222> LOCATION: (76)..(76)
<223> OTHER INFORMATION: Xaa is Ser or absent
<220> FEATURE:
<221> NAME/KEY: VARIANT
<222> LOCATION: (77)..(77)
<223> OTHER INFORMATION: Xaa is Ser or absent
<220> FEATURE:
<221> NAME/KEY: VARIANT
<222> LOCATION: (78)..(78)
<223> OTHER INFORMATION: Xaa is Gly or absent
<220> FEATURE:
<221> NAME/KEY: VARIANT
<222> LOCATION: (79)..(79)
<223> OTHER INFORMATION: Xaa is Ala or absent
<220> FEATURE:
<221> NAME/KEY: VARIANT
<222> LOCATION: (80)..(80)
<223> OTHER INFORMATION: Xaa is Pro or absent
<220> FEATURE:
<221> NAME/KEY: VARIANT
<222> LOCATION: (81)..(81)
<223> OTHER INFORMATION: Xaa is Pro or absent
<220> FEATURE:
<221> NAME/KEY: VARIANT
<222> LOCATION: (82)..(82)
<223> OTHER INFORMATION: Xaa is Pro or absent
<220> FEATURE:
<221> NAME/KEY: VARIANT
<222> LOCATION: (83)..(83)
<223> OTHER INFORMATION: Xaa is Ser or absent
<220> FEATURE:
<221> NAME/KEY: VARIANT
<222> LOCATION: (84)..(84)
<223> OTHER INFORMATION: Xaa is Thr or absent.
<220> FEATURE:
<221> NAME/KEY: VARIANT
<222> LOCATION: (84)..(97)
<223> OTHER INFORMATION: If Xaa at position 84 is any of the amino acids
      listed (as in, the position is not absent), then the Xaa's from
      positions 85-97 are absent; if Xaa at position 84 is absent, then
      the Xaa's from positions 85-97 are not absent.
<220> FEATURE:
<221> NAME/KEY: VARIANT
<222> LOCATION: (85)..(85)
<223> OTHER INFORMATION: Xaa is Lys or absent
<220> FEATURE:
<221> NAME/KEY: VARIANT
<222> LOCATION: (86)..(86)
<223> OTHER INFORMATION: Xaa is Asn or absent
<220> FEATURE:
<221> NAME/KEY: VARIANT
<222> LOCATION: (87)..(87)
<223> OTHER INFORMATION: Xaa is Gly or absent
<220> FEATURE:
<221> NAME/KEY: VARIANT
<222> LOCATION: (88)..(88)
<223> OTHER INFORMATION: Xaa is Gly or absent
<220> FEATURE:
<221> NAME/KEY: VARIANT
<222> LOCATION: (89)..(89)
<223> OTHER INFORMATION: Xaa is Pro or absent
<220> FEATURE:
<221> NAME/KEY: VARIANT
<222> LOCATION: (90)..(90)
<223> OTHER INFORMATION: Xaa is Ser or absent
<220> FEATURE:
<221> NAME/KEY: VARIANT
<222> LOCATION: (91)..(91)
<223> OTHER INFORMATION: Xaa is Ser or absent
<220> FEATURE:
<221> NAME/KEY: VARIANT
<222> LOCATION: (92)..(92)
<223> OTHER INFORMATION: Xaa is Gly or absent
<220> FEATURE:
<221> NAME/KEY: VARIANT
<222> LOCATION: (93)..(93)
<223> OTHER INFORMATION: Xaa is Ala or absent
```

```
<220> FEATURE:
<221> NAME/KEY: VARIANT
<222> LOCATION: (94)..(94)
<223> OTHER INFORMATION: Xaa is Pro or absent
<220> FEATURE:
<221> NAME/KEY: VARIANT
<222> LOCATION: (95)..(95)
<223> OTHER INFORMATION: Xaa is Pro or absent
<220> FEATURE:
<221> NAME/KEY: VARIANT
<222> LOCATION: (96)..(96)
<223> OTHER INFORMATION: Xaa is Pro or absent
<220> FEATURE:
<221> NAME/KEY: VARIANT
<222> LOCATION: (97)..(97)
<223> OTHER INFORMATION: Xaa is Ser or absent
<220> FEATURE:
<221> NAME/KEY: VARIANT
<222> LOCATION: (98)..(98)
<223> OTHER INFORMATION: Xaa is Asp, Asn, or absent.
<220> FEATURE:
<221> NAME/KEY: VARIANT
<222> LOCATION: (98)..(111)
<223> OTHER INFORMATION: If Xaa at position 98 is any of the amino acids
      listed (as in, the position is not absent), then the Xaa's from
      positions 99-111 are absent; if Xaa at position 98 is absent, then
      the Xaa's from positions 99-111 are not absent.
<220> FEATURE:
<221> NAME/KEY: VARIANT
<222> LOCATION: (99)..(99)
<223> OTHER INFORMATION: Xaa is Lys or absent
<220> FEATURE:
<221> NAME/KEY: VARIANT
<222> LOCATION: (100)..(100)
<223> OTHER INFORMATION: Xaa is Asn or absent
<220> FEATURE:
<221> NAME/KEY: VARIANT
<222> LOCATION: (101)..(101)
<223> OTHER INFORMATION: Xaa is Gly or absent
<220> FEATURE:
<221> NAME/KEY: VARIANT
<222> LOCATION: (102)..(102)
<223> OTHER INFORMATION: Xaa is Gly or absent
<220> FEATURE:
<221> NAME/KEY: VARIANT
<222> LOCATION: (103)..(103)
<223> OTHER INFORMATION: Xaa is Pro or absent
<220> FEATURE:
<221> NAME/KEY: VARIANT
<222> LOCATION: (104)..(104)
<223> OTHER INFORMATION: Xaa is Ser or absent
<220> FEATURE:
<221> NAME/KEY: VARIANT
<222> LOCATION: (105)..(105)
<223> OTHER INFORMATION: Xaa is Ser or absent
<220> FEATURE:
<221> NAME/KEY: VARIANT
<222> LOCATION: (106)..(106)
<223> OTHER INFORMATION: Xaa is Gly or absent
<220> FEATURE:
<221> NAME/KEY: VARIANT
<222> LOCATION: (107)..(107)
<223> OTHER INFORMATION: Xaa is Ala or absent
<220> FEATURE:
<221> NAME/KEY: VARIANT
<222> LOCATION: (108)..(108)
<223> OTHER INFORMATION: Xaa is Pro or absent
<220> FEATURE:
<221> NAME/KEY: VARIANT
<222> LOCATION: (109)..(109)
<223> OTHER INFORMATION: Xaa is Pro or absent
<220> FEATURE:
<221> NAME/KEY: VARIANT
<222> LOCATION: (110)..(110)
<223> OTHER INFORMATION: Xaa is Pro or absent
<220> FEATURE:
<221> NAME/KEY: VARIANT
<222> LOCATION: (111)..(111)
<223> OTHER INFORMATION: Xaa is Ser or absent
```

-continued

```
<220> FEATURE:
<221> NAME/KEY: VARIANT
<222> LOCATION: (112)..(112)
<223> OTHER INFORMATION: Xaa is Lys or is absent
<220> FEATURE:
<221> NAME/KEY: VARIANT
<222> LOCATION: (112)..(124)
<223> OTHER INFORMATION: If Xaa at position 112 is absent, then Xaa's
      from positions 113-124 are also absent; if Xaa at position 112 is
      not absent, then Xaa's from positions 113-124 are also not absent.
<220> FEATURE:
<221> NAME/KEY: VARIANT
<222> LOCATION: (113)..(113)
<223> OTHER INFORMATION: Xaa is Asn or absent
<220> FEATURE:
<221> NAME/KEY: VARIANT
<222> LOCATION: (114)..(114)
<223> OTHER INFORMATION: Xaa is Gly or absent
<220> FEATURE:
<221> NAME/KEY: VARIANT
<222> LOCATION: (115)..(115)
<223> OTHER INFORMATION: Xaa is Gly or absent
<220> FEATURE:
<221> NAME/KEY: VARIANT
<222> LOCATION: (116)..(116)
<223> OTHER INFORMATION: Xaa is Pro or absent
<220> FEATURE:
<221> NAME/KEY: VARIANT
<222> LOCATION: (117)..(117)
<223> OTHER INFORMATION: Xaa is Ser or absent
<220> FEATURE:
<221> NAME/KEY: VARIANT
<222> LOCATION: (118)..(118)
<223> OTHER INFORMATION: Xaa is Ser or absent
<220> FEATURE:
<221> NAME/KEY: VARIANT
<222> LOCATION: (119)..(119)
<223> OTHER INFORMATION: Xaa is Gly or absent
<220> FEATURE:
<221> NAME/KEY: VARIANT
<222> LOCATION: (120)..(120)
<223> OTHER INFORMATION: Xaa is Ala or absent
<220> FEATURE:
<221> NAME/KEY: VARIANT
<222> LOCATION: (121)..(121)
<223> OTHER INFORMATION: Xaa is Pro or absent
<220> FEATURE:
<221> NAME/KEY: VARIANT
<222> LOCATION: (122)..(122)
<223> OTHER INFORMATION: Xaa is Pro or absent
<220> FEATURE:
<221> NAME/KEY: VARIANT
<222> LOCATION: (123)..(123)
<223> OTHER INFORMATION: Xaa is Pro or absent
<220> FEATURE:
<221> NAME/KEY: VARIANT
<222> LOCATION: (124)..(124)
<223> OTHER INFORMATION: Xaa is Ser or absent

<400> SEQUENCE: 3

His Xaa Xaa Gly Xaa Phe Xaa Xaa Xaa Xaa Xaa Xaa Xaa Xaa Xaa
1               5                   10                  15

Xaa Ala Xaa Xaa Xaa Phe Ile Xaa Trp Leu Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95
```

```
Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa
        115                 120

<210> SEQ ID NO 4
<211> LENGTH: 33
<212> TYPE: PRT
<213> ORGANISM: Artificial sequence
<220> FEATURE:
<223> OTHER INFORMATION: Synthetic sequence

<400> SEQUENCE: 4

His Gly Asp Gly Ser Phe Ser Asp Glu Met Asn Thr Ile Leu Asp Gly
1               5                   10                  15

Gln Ala Ala Arg Asp Phe Ile Asn Trp Leu Ile Gln Thr Lys Ile Thr
            20                  25                  30

Asp

<210> SEQ ID NO 5
<211> LENGTH: 33
<212> TYPE: PRT
<213> ORGANISM: Artificial sequence
<220> FEATURE:
<223> OTHER INFORMATION: Synthetic sequence

<400> SEQUENCE: 5

His Gly Asp Gly Ser Phe Ser Asp Glu Met Asn Thr Ile Leu Asp Asn
1               5                   10                  15

Gln Ala Ala Arg Asp Phe Ile Asn Trp Leu Ile Gln Thr Lys Ile Thr
            20                  25                  30

Asp

<210> SEQ ID NO 6
<211> LENGTH: 30
<212> TYPE: PRT
<213> ORGANISM: Artificial sequence
<220> FEATURE:
<223> OTHER INFORMATION: Synthetic sequence

<400> SEQUENCE: 6

His Gly Asp Gly Ser Phe Ser Asp Glu Met Asn Thr Ile Leu Asp Ser
1               5                   10                  15

Gln Ala Ala Arg Asp Phe Ile Asn Trp Leu Ile Gln Thr Lys
            20                  25                  30

<210> SEQ ID NO 7
<211> LENGTH: 110
<212> TYPE: PRT
<213> ORGANISM: Artificial sequence
<220> FEATURE:
<223> OTHER INFORMATION: Synthetic sequence: GLP-2 analogue: General
      Formula Ia of PCT/EP2013/059320
<220> FEATURE:
<221> NAME/KEY: VARIANT
<222> LOCATION: (2)..(2)
<223> OTHER INFORMATION: Xaa is Gly, Ala or Aib
<220> FEATURE:
<221> NAME/KEY: VARIANT
<222> LOCATION: (3)..(3)
<223> OTHER INFORMATION: Xaa is Glu, Gln or Asp
<220> FEATURE:
<221> NAME/KEY: VARIANT
<222> LOCATION: (5)..(5)
<223> OTHER INFORMATION: Xaa is Ser or Thr
<220> FEATURE:
```

```
<221> NAME/KEY: VARIANT
<222> LOCATION: (7)..(7)
<223> OTHER INFORMATION: Xaa is Ser or Thr
<220> FEATURE:
<221> NAME/KEY: VARIANT
<222> LOCATION: (8)..(8)
<223> OTHER INFORMATION: Xaa is Asp, Glu or Ser
<220> FEATURE:
<221> NAME/KEY: VARIANT
<222> LOCATION: (9)..(9)
<223> OTHER INFORMATION: Xaa is Glu or Asp
<220> FEATURE:
<221> NAME/KEY: VARIANT
<222> LOCATION: (10)..(10)
<223> OTHER INFORMATION: Xaa is Met, Val, Leu or Tyr
<220> FEATURE:
<221> NAME/KEY: VARIANT
<222> LOCATION: (11)..(11)
<223> OTHER INFORMATION: Xaa is Asn or Ser
<220> FEATURE:
<221> NAME/KEY: VARIANT
<222> LOCATION: (12)..(12)
<223> OTHER INFORMATION: Xaa is Thr, Ser or Lys
<220> FEATURE:
<221> NAME/KEY: VARIANT
<222> LOCATION: (13)..(13)
<223> OTHER INFORMATION: Xaa is Ile, Leu, Val, Tyr, Phe or Gln
<220> FEATURE:
<221> NAME/KEY: VARIANT
<222> LOCATION: (15)..(15)
<223> OTHER INFORMATION: Xaa is Asp or Glu
<220> FEATURE:
<221> NAME/KEY: VARIANT
<222> LOCATION: (16)..(16)
<223> OTHER INFORMATION: Xaa is Asn, Gln, Gly, Ser, Ala, Glu or Lys
<220> FEATURE:
<221> NAME/KEY: VARIANT
<222> LOCATION: (17)..(17)
<223> OTHER INFORMATION: Xaa is Gln, Lys, Arg, His or Glu
<220> FEATURE:
<221> NAME/KEY: VARIANT
<222> LOCATION: (20)..(20)
<223> OTHER INFORMATION: Xaa is Arg, Lys or His
<220> FEATURE:
<221> NAME/KEY: VARIANT
<222> LOCATION: (21)..(21)
<223> OTHER INFORMATION: Xaa is Asp, Glu or Leu
<220> FEATURE:
<221> NAME/KEY: VARIANT
<222> LOCATION: (24)..(24)
<223> OTHER INFORMATION: Xaa is Asn, Ala, Glu or Lys
<220> FEATURE:
<221> NAME/KEY: VARIANT
<222> LOCATION: (27)..(27)
<223> OTHER INFORMATION: Xaa is Ile, Leu, Val, Glu or Lys
<220> FEATURE:
<221> NAME/KEY: VARIANT
<222> LOCATION: (28)..(28)
<223> OTHER INFORMATION: Xaa is Gln, Asn, Lys, Ser, Gly, or absent.
<220> FEATURE:
<221> NAME/KEY: VARIANT
<222> LOCATION: (28)..(39)
<223> OTHER INFORMATION: If Xaa at position 28 is any of the amino acids
      listed (as in, the position is not absent), then the Xaa's from
      positions 29-39 are absent; if Xaa at position 28 is absent, then
      the Xaa's from positions 29-39 are not absent.
<220> FEATURE:
<221> NAME/KEY: VARIANT
<222> LOCATION: (29)..(29)
<223> OTHER INFORMATION: Xaa is Gly or absent
<220> FEATURE:
<221> NAME/KEY: VARIANT
<222> LOCATION: (30)..(30)
<223> OTHER INFORMATION: Xaa is Gly or absent
<220> FEATURE:
<221> NAME/KEY: VARIANT
<222> LOCATION: (31)..(31)
<223> OTHER INFORMATION: Xaa is Pro or absent
<220> FEATURE:
```

```
<221> NAME/KEY: VARIANT
<222> LOCATION: (32)..(32)
<223> OTHER INFORMATION: Xaa is Ser or absent
<220> FEATURE:
<221> NAME/KEY: VARIANT
<222> LOCATION: (33)..(33)
<223> OTHER INFORMATION: Xaa is Ser or absent
<220> FEATURE:
<221> NAME/KEY: VARIANT
<222> LOCATION: (34)..(34)
<223> OTHER INFORMATION: Xaa is Gly or absent
<220> FEATURE:
<221> NAME/KEY: VARIANT
<222> LOCATION: (35)..(35)
<223> OTHER INFORMATION: Xaa is Ala or absent
<220> FEATURE:
<221> NAME/KEY: VARIANT
<222> LOCATION: (36)..(36)
<223> OTHER INFORMATION: Xaa is Pro or absent
<220> FEATURE:
<221> NAME/KEY: VARIANT
<222> LOCATION: (37)..(37)
<223> OTHER INFORMATION: Xaa is Pro or absent
<220> FEATURE:
<221> NAME/KEY: VARIANT
<222> LOCATION: (38)..(38)
<223> OTHER INFORMATION: Xaa is Pro or absent
<220> FEATURE:
<221> NAME/KEY: VARIANT
<222> LOCATION: (39)..(39)
<223> OTHER INFORMATION: Xaa is Ser or absent
<220> FEATURE:
<221> NAME/KEY: VARIANT
<222> LOCATION: (40)..(40)
<223> OTHER INFORMATION: Xaa is Thr, Ala, or absent.
<220> FEATURE:
<221> NAME/KEY: VARIANT
<222> LOCATION: (40)..(51)
<223> OTHER INFORMATION: If Xaa at position 40 is any of the amino acids
      listed (as in, the position is not absent), then the Xaa's from
      positions 41-51 are absent; if Xaa at position 40 is absent, then
      the Xaa's from positions 41-51 are not absent.
<220> FEATURE:
<221> NAME/KEY: VARIANT
<222> LOCATION: (41)..(41)
<223> OTHER INFORMATION: Xaa is Gly or absent
<220> FEATURE:
<221> NAME/KEY: VARIANT
<222> LOCATION: (42)..(42)
<223> OTHER INFORMATION: Xaa is Gly or absent
<220> FEATURE:
<221> NAME/KEY: VARIANT
<222> LOCATION: (43)..(43)
<223> OTHER INFORMATION: Xaa is Pro or absent
<220> FEATURE:
<221> NAME/KEY: VARIANT
<222> LOCATION: (44)..(44)
<223> OTHER INFORMATION: Xaa is Ser or absent
<220> FEATURE:
<221> NAME/KEY: VARIANT
<222> LOCATION: (45)..(45)
<223> OTHER INFORMATION: Xaa is Ser or absent
<220> FEATURE:
<221> NAME/KEY: VARIANT
<222> LOCATION: (46)..(46)
<223> OTHER INFORMATION: Xaa is Gly or absent
<220> FEATURE:
<221> NAME/KEY: VARIANT
<222> LOCATION: (47)..(47)
<223> OTHER INFORMATION: Xaa is Ala or absent
<220> FEATURE:
<221> NAME/KEY: VARIANT
<222> LOCATION: (48)..(48)
<223> OTHER INFORMATION: Xaa is Pro or absent
<220> FEATURE:
<221> NAME/KEY: VARIANT
<222> LOCATION: (49)..(49)
<223> OTHER INFORMATION: Xaa is Pro or absent
<220> FEATURE:
```

```
<221> NAME/KEY: VARIANT
<222> LOCATION: (50)..(50)
<223> OTHER INFORMATION: Xaa is Pro or absent
<220> FEATURE:
<221> NAME/KEY: VARIANT
<222> LOCATION: (51)..(51)
<223> OTHER INFORMATION: Xaa is Ser or absent
<220> FEATURE:
<221> NAME/KEY: VARIANT
<222> LOCATION: (52)..(52)
<223> OTHER INFORMATION: Xaa is Lys or absent.
<220> FEATURE:
<221> NAME/KEY: VARIANT
<222> LOCATION: (52)..(63)
<223> OTHER INFORMATION: If Xaa at position 52 is any of the amino acids
      listed (as in, the position is not absent), then the Xaa's from
      positions 53-63 are absent; if Xaa at position 52 is absent, then
      the Xaa's from positions 53-63 are not absent.
<220> FEATURE:
<221> NAME/KEY: VARIANT
<222> LOCATION: (53)..(53)
<223> OTHER INFORMATION: Xaa is Gly or absent
<220> FEATURE:
<221> NAME/KEY: VARIANT
<222> LOCATION: (54)..(54)
<223> OTHER INFORMATION: Xaa is Gly or absent
<220> FEATURE:
<221> NAME/KEY: VARIANT
<222> LOCATION: (55)..(55)
<223> OTHER INFORMATION: Xaa is Pro or absent
<220> FEATURE:
<221> NAME/KEY: VARIANT
<222> LOCATION: (56)..(56)
<223> OTHER INFORMATION: Xaa is Ser or absent
<220> FEATURE:
<221> NAME/KEY: VARIANT
<222> LOCATION: (57)..(57)
<223> OTHER INFORMATION: Xaa is Ser or absent
<220> FEATURE:
<221> NAME/KEY: VARIANT
<222> LOCATION: (58)..(58)
<223> OTHER INFORMATION: Xaa is Gly or absent
<220> FEATURE:
<221> NAME/KEY: VARIANT
<222> LOCATION: (59)..(59)
<223> OTHER INFORMATION: Xaa is Ala or absent
<220> FEATURE:
<221> NAME/KEY: VARIANT
<222> LOCATION: (60)..(60)
<223> OTHER INFORMATION: Xaa is Pro or absent
<220> FEATURE:
<221> NAME/KEY: VARIANT
<222> LOCATION: (61)..(61)
<223> OTHER INFORMATION: Xaa is Pro or absent
<220> FEATURE:
<221> NAME/KEY: VARIANT
<222> LOCATION: (62)..(62)
<223> OTHER INFORMATION: Xaa is Pro or absent
<220> FEATURE:
<221> NAME/KEY: VARIANT
<222> LOCATION: (63)..(63)
<223> OTHER INFORMATION: Xaa is Ser or absent
<220> FEATURE:
<221> NAME/KEY: VARIANT
<222> LOCATION: (64)..(64)
<223> OTHER INFORMATION: Xaa is Ile, Pro, or absent.
<220> FEATURE:
<221> NAME/KEY: VARIANT
<222> LOCATION: (64)..(75)
<223> OTHER INFORMATION: If Xaa at position 64 is any of the amino acids
      listed (as in, the position is not absent), then the Xaa's from
      positions 65-75 are absent; if Xaa at position 64 is absent, then
      the Xaa's from positions 65-75 are not absent.
<220> FEATURE:
<221> NAME/KEY: VARIANT
<222> LOCATION: (65)..(65)
<223> OTHER INFORMATION: Xaa is Gly or absent
<220> FEATURE:
<221> NAME/KEY: VARIANT
```

```
<222> LOCATION: (66)..(66)
<223> OTHER INFORMATION: Xaa is Gly or absent
<220> FEATURE:
<221> NAME/KEY: VARIANT
<222> LOCATION: (67)..(67)
<223> OTHER INFORMATION: Xaa is Pro or absent
<220> FEATURE:
<221> NAME/KEY: VARIANT
<222> LOCATION: (68)..(68)
<223> OTHER INFORMATION: Xaa is Ser or absent
<220> FEATURE:
<221> NAME/KEY: VARIANT
<222> LOCATION: (69)..(69)
<223> OTHER INFORMATION: Xaa is Ser or absent
<220> FEATURE:
<221> NAME/KEY: VARIANT
<222> LOCATION: (70)..(70)
<223> OTHER INFORMATION: Xaa is Gly or absent
<220> FEATURE:
<221> NAME/KEY: VARIANT
<222> LOCATION: (71)..(71)
<223> OTHER INFORMATION: Xaa is Ala or absent
<220> FEATURE:
<221> NAME/KEY: VARIANT
<222> LOCATION: (72)..(72)
<223> OTHER INFORMATION: Xaa is Pro or absent
<220> FEATURE:
<221> NAME/KEY: VARIANT
<222> LOCATION: (73)..(73)
<223> OTHER INFORMATION: Xaa is Pro or absent
<220> FEATURE:
<221> NAME/KEY: VARIANT
<222> LOCATION: (74)..(74)
<223> OTHER INFORMATION: Xaa is Pro or absent
<220> FEATURE:
<221> NAME/KEY: VARIANT
<222> LOCATION: (75)..(75)
<223> OTHER INFORMATION: Xaa is Ser or absent
<220> FEATURE:
<221> NAME/KEY: VARIANT
<222> LOCATION: (76)..(76)
<223> OTHER INFORMATION: Xaa is Thr or absent.
<220> FEATURE:
<221> NAME/KEY: VARIANT
<222> LOCATION: (76)..(87)
<223> OTHER INFORMATION: If Xaa at position 76 is any of the amino acids
      listed (as in, the position is not absent), then the Xaa's from
      positions 77-87 are absent; if Xaa at position 76 is absent, then
      the Xaa's from positions 77-87 are not absent.
<220> FEATURE:
<221> NAME/KEY: VARIANT
<222> LOCATION: (77)..(77)
<223> OTHER INFORMATION: Xaa is Gly or absent
<220> FEATURE:
<221> NAME/KEY: VARIANT
<222> LOCATION: (78)..(78)
<223> OTHER INFORMATION: Xaa is Gly or absent
<220> FEATURE:
<221> NAME/KEY: VARIANT
<222> LOCATION: (79)..(79)
<223> OTHER INFORMATION: Xaa is Pro or absent
<220> FEATURE:
<221> NAME/KEY: VARIANT
<222> LOCATION: (80)..(80)
<223> OTHER INFORMATION: Xaa is Ser or absent
<220> FEATURE:
<221> NAME/KEY: VARIANT
<222> LOCATION: (81)..(81)
<223> OTHER INFORMATION: Xaa is Ser or absent
<220> FEATURE:
<221> NAME/KEY: VARIANT
<222> LOCATION: (82)..(82)
<223> OTHER INFORMATION: Xaa is Gly or absent
<220> FEATURE:
<221> NAME/KEY: VARIANT
<222> LOCATION: (83)..(83)
<223> OTHER INFORMATION: Xaa is Ala or absent
<220> FEATURE:
<221> NAME/KEY: VARIANT
```

```
<222> LOCATION: (84)..(84)
<223> OTHER INFORMATION: Xaa is Pro or absent
<220> FEATURE:
<221> NAME/KEY: VARIANT
<222> LOCATION: (85)..(85)
<223> OTHER INFORMATION: Xaa is Pro or absent
<220> FEATURE:
<221> NAME/KEY: VARIANT
<222> LOCATION: (86)..(86)
<223> OTHER INFORMATION: Xaa is Pro or absent
<220> FEATURE:
<221> NAME/KEY: VARIANT
<222> LOCATION: (87)..(87)
<223> OTHER INFORMATION: Xaa is Ser or absent
<220> FEATURE:
<221> NAME/KEY: VARIANT
<222> LOCATION: (88)..(88)
<223> OTHER INFORMATION: Xaa is Asp, Asn, or absent.
<220> FEATURE:
<221> NAME/KEY: VARIANT
<222> LOCATION: (88)..(99)
<223> OTHER INFORMATION: If Xaa at position 88 is any of the amino acids
      listed (as in, the position is not absent), then the Xaa's from
      positions 89-99 are absent; if Xaa at position 88 is absent, then
      the Xaa's from positions 89-99 are not absent.
<220> FEATURE:
<221> NAME/KEY: VARIANT
<222> LOCATION: (89)..(89)
<223> OTHER INFORMATION: Xaa is Gly or absent
<220> FEATURE:
<221> NAME/KEY: VARIANT
<222> LOCATION: (90)..(90)
<223> OTHER INFORMATION: Xaa is Gly or absent
<220> FEATURE:
<221> NAME/KEY: VARIANT
<222> LOCATION: (91)..(91)
<223> OTHER INFORMATION: Xaa is Pro or absent
<220> FEATURE:
<221> NAME/KEY: VARIANT
<222> LOCATION: (92)..(92)
<223> OTHER INFORMATION: Xaa is Ser or absent
<220> FEATURE:
<221> NAME/KEY: VARIANT
<222> LOCATION: (93)..(93)
<223> OTHER INFORMATION: Xaa is Ser or absent
<220> FEATURE:
<221> NAME/KEY: VARIANT
<222> LOCATION: (94)..(94)
<223> OTHER INFORMATION: Xaa is Gly or absent
<220> FEATURE:
<221> NAME/KEY: VARIANT
<222> LOCATION: (95)..(95)
<223> OTHER INFORMATION: Xaa is Ala or absent
<220> FEATURE:
<221> NAME/KEY: VARIANT
<222> LOCATION: (96)..(96)
<223> OTHER INFORMATION: Xaa is Pro or absent
<220> FEATURE:
<221> NAME/KEY: VARIANT
<222> LOCATION: (97)..(97)
<223> OTHER INFORMATION: Xaa is Pro or absent
<220> FEATURE:
<221> NAME/KEY: VARIANT
<222> LOCATION: (98)..(98)
<223> OTHER INFORMATION: Xaa is Pro or absent
<220> FEATURE:
<221> NAME/KEY: VARIANT
<222> LOCATION: (99)..(99)
<223> OTHER INFORMATION: Xaa is Ser or absent
<220> FEATURE:
<221> NAME/KEY: VARIANT
<222> LOCATION: (100)..(100)
<223> OTHER INFORMATION: Xaa is Gly or absent
<220> FEATURE:
<221> NAME/KEY: VARIANT
<222> LOCATION: (100)..(110)
<223> OTHER INFORMATION: If Xaa at position 100 is absent, then Xaa's
      from positions 101-110 are also absent; if Xaa at position 100 is
      not absent, then Xaa's from positions 101-110 are also not absent.
```

```
-continued

<220> FEATURE:
<221> NAME/KEY: VARIANT
<222> LOCATION: (101)..(101)
<223> OTHER INFORMATION: Xaa is Gly or absent
<220> FEATURE:
<221> NAME/KEY: VARIANT
<222> LOCATION: (102)..(102)
<223> OTHER INFORMATION: Xaa is Pro or absent
<220> FEATURE:
<221> NAME/KEY: VARIANT
<222> LOCATION: (103)..(103)
<223> OTHER INFORMATION: Xaa is Ser or absent
<220> FEATURE:
<221> NAME/KEY: VARIANT
<222> LOCATION: (104)..(104)
<223> OTHER INFORMATION: Xaa is Ser or absent
<220> FEATURE:
<221> NAME/KEY: VARIANT
<222> LOCATION: (105)..(105)
<223> OTHER INFORMATION: Xaa is Gly or absent
<220> FEATURE:
<221> NAME/KEY: VARIANT
<222> LOCATION: (106)..(106)
<223> OTHER INFORMATION: Xaa is Ala or absent
<220> FEATURE:
<221> NAME/KEY: VARIANT
<222> LOCATION: (107)..(107)
<223> OTHER INFORMATION: Xaa is Pro or absent
<220> FEATURE:
<221> NAME/KEY: VARIANT
<222> LOCATION: (108)..(108)
<223> OTHER INFORMATION: Xaa is Pro or absent
<220> FEATURE:
<221> NAME/KEY: VARIANT
<222> LOCATION: (109)..(109)
<223> OTHER INFORMATION: Xaa is Pro or absent
<220> FEATURE:
<221> NAME/KEY: VARIANT
<222> LOCATION: (110)..(110)
<223> OTHER INFORMATION: Xaa is Ser or absent

<400> SEQUENCE: 7

His Xaa Xaa Gly Xaa Phe Xaa Xaa Xaa Xaa Xaa Xaa Leu Xaa Xaa
 1               5                  10                  15

Xaa Ala Ala Xaa Xaa Phe Ile Xaa Trp Leu Xaa Xaa Xaa Xaa Xaa
                 20                  25                  30

Xaa Xaa Xaa Xaa Xaa Xaa Xaa Xaa Xaa Xaa Xaa Xaa Xaa Xaa Xaa
             35                  40                  45

Xaa Xaa Xaa Xaa Xaa Xaa Xaa Xaa Xaa Xaa Xaa Xaa Xaa Xaa Xaa
         50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa
                 85                  90                  95

Xaa Xaa Xaa Xaa Xaa Xaa Xaa Xaa Xaa Xaa Xaa Xaa Xaa Xaa
            100                 105                 110

<210> SEQ ID NO 8
<211> LENGTH: 124
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (2)..(2)
<223> OTHER INFORMATION: Xaa is Gly, Ala or Aib
<220> FEATURE:
<221> NAME/KEY: VARIANT
<222> LOCATION: (3)..(3)
<223> OTHER INFORMATION: Xaa is Glu, Gln or Asp
```

-continued

```
<220> FEATURE:
<221> NAME/KEY: VARIANT
<222> LOCATION: (5)..(5)
<223> OTHER INFORMATION: Xaa is Ser or Thr
<220> FEATURE:
<221> NAME/KEY: VARIANT
<222> LOCATION: (7)..(7)
<223> OTHER INFORMATION: Xaa is Ser or Thr
<220> FEATURE:
<221> NAME/KEY: VARIANT
<222> LOCATION: (8)..(8)
<223> OTHER INFORMATION: Xaa is Asp, Glu or Ser
<220> FEATURE:
<221> NAME/KEY: VARIANT
<222> LOCATION: (9)..(9)
<223> OTHER INFORMATION: Xaa is Glu or Asp
<220> FEATURE:
<221> NAME/KEY: VARIANT
<222> LOCATION: (10)..(10)
<223> OTHER INFORMATION: Xaa is Met, Val, Leu or Tyr
<220> FEATURE:
<221> NAME/KEY: VARIANT
<222> LOCATION: (11)..(11)
<223> OTHER INFORMATION: Xaa is Asn or Ser
<220> FEATURE:
<221> NAME/KEY: VARIANT
<222> LOCATION: (12)..(12)
<223> OTHER INFORMATION: Xaa is Thr, Ser or Lys
<220> FEATURE:
<221> NAME/KEY: VARIANT
<222> LOCATION: (13)..(13)
<223> OTHER INFORMATION: Xaa is Ile, Leu, Val, Tyr, Phe or Gln
<220> FEATURE:
<221> NAME/KEY: VARIANT
<222> LOCATION: (15)..(15)
<223> OTHER INFORMATION: Xaa is Asp or Glu
<220> FEATURE:
<221> NAME/KEY: VARIANT
<222> LOCATION: (16)..(16)
<223> OTHER INFORMATION: Xaa is Asn, Gln, Gly, Ser, Ala, Glu or Lys
<220> FEATURE:
<221> NAME/KEY: VARIANT
<222> LOCATION: (17)..(17)
<223> OTHER INFORMATION: Xaa is Gln, Lys, Arg, His or Glu
<220> FEATURE:
<221> NAME/KEY: VARIANT
<222> LOCATION: (20)..(20)
<223> OTHER INFORMATION: Xaa is Arg, Lys or His
<220> FEATURE:
<221> NAME/KEY: VARIANT
<222> LOCATION: (21)..(21)
<223> OTHER INFORMATION: Xaa is Asp, Glu or Leu
<220> FEATURE:
<221> NAME/KEY: VARIANT
<222> LOCATION: (24)..(24)
<223> OTHER INFORMATION: Xaa is Asn, Ala, Glu or Lys
<220> FEATURE:
<221> NAME/KEY: VARIANT
<222> LOCATION: (27)..(27)
<223> OTHER INFORMATION: Xaa is Ile, Leu, Val, Glu or Lys
<220> FEATURE:
<221> NAME/KEY: VARIANT
<222> LOCATION: (28)..(28)
<223> OTHER INFORMATION: Xaa is Gln, Asn, Lys, Ser, Gly, or absent.
<220> FEATURE:
<221> NAME/KEY: VARIANT
<222> LOCATION: (28)..(41)
<223> OTHER INFORMATION: If Xaa at position 28 is any of the amino acids
      listed (as in, the position is not absent), then the Xaa's from
      positions 29-41 are absent; if Xaa at position 28 is absent, then
      the Xaa's from positions 29-41 are not absent.
<220> FEATURE:
<221> NAME/KEY: VARIANT
<222> LOCATION: (29)..(29)
<223> OTHER INFORMATION: Xaa is Lys or absent
<220> FEATURE:
<221> NAME/KEY: VARIANT
<222> LOCATION: (30)..(30)
<223> OTHER INFORMATION: Xaa is Asn or absent
```

-continued

```
<220> FEATURE:
<221> NAME/KEY: VARIANT
<222> LOCATION: (31)..(31)
<223> OTHER INFORMATION: Xaa is Gly or absent
<220> FEATURE:
<221> NAME/KEY: VARIANT
<222> LOCATION: (32)..(32)
<223> OTHER INFORMATION: Xaa is Gly or absent
<220> FEATURE:
<221> NAME/KEY: VARIANT
<222> LOCATION: (33)..(33)
<223> OTHER INFORMATION: Xaa is Pro or absent
<220> FEATURE:
<221> NAME/KEY: VARIANT
<222> LOCATION: (34)..(34)
<223> OTHER INFORMATION: Xaa is Ser or absent
<220> FEATURE:
<221> NAME/KEY: VARIANT
<222> LOCATION: (35)..(35)
<223> OTHER INFORMATION: Xaa is Ser or absent
<220> FEATURE:
<221> NAME/KEY: VARIANT
<222> LOCATION: (36)..(36)
<223> OTHER INFORMATION: Xaa is Gly or absent
<220> FEATURE:
<221> NAME/KEY: VARIANT
<222> LOCATION: (37)..(37)
<223> OTHER INFORMATION: Xaa is Ala or absent
<220> FEATURE:
<221> NAME/KEY: VARIANT
<222> LOCATION: (38)..(38)
<223> OTHER INFORMATION: Xaa is Pro or absent
<220> FEATURE:
<221> NAME/KEY: VARIANT
<222> LOCATION: (39)..(39)
<223> OTHER INFORMATION: Xaa is Pro or absent
<220> FEATURE:
<221> NAME/KEY: VARIANT
<222> LOCATION: (40)..(40)
<223> OTHER INFORMATION: Xaa is Pro or absent
<220> FEATURE:
<221> NAME/KEY: VARIANT
<222> LOCATION: (41)..(41)
<223> OTHER INFORMATION: Xaa is Ser or absent
<220> FEATURE:
<221> NAME/KEY: VARIANT
<222> LOCATION: (42)..(42)
<223> OTHER INFORMATION: Xaa is Thr, Ala, or absent.
<220> FEATURE:
<221> NAME/KEY: VARIANT
<222> LOCATION: (42)..(55)
<223> OTHER INFORMATION: If Xaa at position 42 is any of the amino acids
      listed (as in, the position is not absent), then the Xaa's from
      positions 43-55 are absent; if Xaa at position 42 is absent, then
      the Xaa's from positions 43-55 are not absent.
<220> FEATURE:
<221> NAME/KEY: VARIANT
<222> LOCATION: (43)..(43)
<223> OTHER INFORMATION: Xaa is Lys or absent
<220> FEATURE:
<221> NAME/KEY: VARIANT
<222> LOCATION: (44)..(44)
<223> OTHER INFORMATION: Xaa is Asn or absent
<220> FEATURE:
<221> NAME/KEY: VARIANT
<222> LOCATION: (45)..(45)
<223> OTHER INFORMATION: Xaa is Gly or absent
<220> FEATURE:
<221> NAME/KEY: VARIANT
<222> LOCATION: (46)..(46)
<223> OTHER INFORMATION: Xaa is Gly or absent
<220> FEATURE:
<221> NAME/KEY: VARIANT
<222> LOCATION: (47)..(47)
<223> OTHER INFORMATION: Xaa is Pro or absent
<220> FEATURE:
<221> NAME/KEY: VARIANT
<222> LOCATION: (48)..(48)
<223> OTHER INFORMATION: Xaa is Ser or absent
```

```
<220> FEATURE:
<221> NAME/KEY: VARIANT
<222> LOCATION: (49)..(49)
<223> OTHER INFORMATION: Xaa is Ser or absent
<220> FEATURE:
<221> NAME/KEY: VARIANT
<222> LOCATION: (50)..(50)
<223> OTHER INFORMATION: Xaa is Gly or absent
<220> FEATURE:
<221> NAME/KEY: VARIANT
<222> LOCATION: (51)..(51)
<223> OTHER INFORMATION: Xaa is Ala or absent
<220> FEATURE:
<221> NAME/KEY: VARIANT
<222> LOCATION: (52)..(52)
<223> OTHER INFORMATION: Xaa is Pro or absent
<220> FEATURE:
<221> NAME/KEY: VARIANT
<222> LOCATION: (53)..(53)
<223> OTHER INFORMATION: Xaa is Pro or absent
<220> FEATURE:
<221> NAME/KEY: VARIANT
<222> LOCATION: (54)..(54)
<223> OTHER INFORMATION: Xaa is Pro or absent
<220> FEATURE:
<221> NAME/KEY: VARIANT
<222> LOCATION: (55)..(55)
<223> OTHER INFORMATION: Xaa is Ser or absent
<220> FEATURE:
<221> NAME/KEY: VARIANT
<222> LOCATION: (56)..(56)
<223> OTHER INFORMATION: Xaa is Lys, or absent.
<220> FEATURE:
<221> NAME/KEY: VARIANT
<222> LOCATION: (56)..(69)
<223> OTHER INFORMATION: If Xaa at position 56 is any of the amino acids
      listed (as in, the position is not absent), then the Xaa's from
      positions 57-69 are absent; if Xaa at position 56 is absent, then
      the Xaa's from positions 57-69 are not absent.
<220> FEATURE:
<221> NAME/KEY: VARIANT
<222> LOCATION: (57)..(57)
<223> OTHER INFORMATION: Xaa is Lys or absent
<220> FEATURE:
<221> NAME/KEY: VARIANT
<222> LOCATION: (58)..(58)
<223> OTHER INFORMATION: Xaa is Asn or absent
<220> FEATURE:
<221> NAME/KEY: VARIANT
<222> LOCATION: (59)..(59)
<223> OTHER INFORMATION: Xaa is Gly or absent
<220> FEATURE:
<221> NAME/KEY: VARIANT
<222> LOCATION: (60)..(60)
<223> OTHER INFORMATION: Xaa is Gly or absent
<220> FEATURE:
<221> NAME/KEY: VARIANT
<222> LOCATION: (61)..(61)
<223> OTHER INFORMATION: Xaa is Pro or absent
<220> FEATURE:
<221> NAME/KEY: VARIANT
<222> LOCATION: (62)..(62)
<223> OTHER INFORMATION: Xaa is Ser or absent
<220> FEATURE:
<221> NAME/KEY: VARIANT
<222> LOCATION: (63)..(63)
<223> OTHER INFORMATION: Xaa is Ser or absent
<220> FEATURE:
<221> NAME/KEY: VARIANT
<222> LOCATION: (64)..(64)
<223> OTHER INFORMATION: Xaa is Gly or absent
<220> FEATURE:
<221> NAME/KEY: VARIANT
<222> LOCATION: (65)..(65)
<223> OTHER INFORMATION: Xaa is Ala or absent
<220> FEATURE:
<221> NAME/KEY: VARIANT
<222> LOCATION: (66)..(66)
<223> OTHER INFORMATION: Xaa is Pro or absent
```

```
<220> FEATURE:
<221> NAME/KEY: VARIANT
<222> LOCATION: (67)..(67)
<223> OTHER INFORMATION: Xaa is Pro or absent
<220> FEATURE:
<221> NAME/KEY: VARIANT
<222> LOCATION: (68)..(68)
<223> OTHER INFORMATION: Xaa is Pro or absent
<220> FEATURE:
<221> NAME/KEY: VARIANT
<222> LOCATION: (69)..(69)
<223> OTHER INFORMATION: Xaa is Ser or absent
<220> FEATURE:
<221> NAME/KEY: VARIANT
<222> LOCATION: (70)..(70)
<223> OTHER INFORMATION: Xaa is Ile, Pro, or absent.
<220> FEATURE:
<221> NAME/KEY: VARIANT
<222> LOCATION: (70)..(83)
<223> OTHER INFORMATION: If Xaa at position 70 is any of the amino acids
      listed (as in, the position is not absent), then the Xaa's from
      positions 71-83 are absent; if Xaa at position 70 is absent, then
      the Xaa's from positions 71-83 are not absent.
<220> FEATURE:
<221> NAME/KEY: VARIANT
<222> LOCATION: (71)..(71)
<223> OTHER INFORMATION: Xaa is Lys or absent
<220> FEATURE:
<221> NAME/KEY: VARIANT
<222> LOCATION: (72)..(72)
<223> OTHER INFORMATION: Xaa is Asn or absent
<220> FEATURE:
<221> NAME/KEY: VARIANT
<222> LOCATION: (73)..(73)
<223> OTHER INFORMATION: Xaa is Gly or absent
<220> FEATURE:
<221> NAME/KEY: VARIANT
<222> LOCATION: (74)..(74)
<223> OTHER INFORMATION: Xaa is Gly or absent
<220> FEATURE:
<221> NAME/KEY: VARIANT
<222> LOCATION: (75)..(75)
<223> OTHER INFORMATION: Xaa is Pro or absent
<220> FEATURE:
<221> NAME/KEY: VARIANT
<222> LOCATION: (76)..(76)
<223> OTHER INFORMATION: Xaa is Ser or absent
<220> FEATURE:
<221> NAME/KEY: VARIANT
<222> LOCATION: (77)..(77)
<223> OTHER INFORMATION: Xaa is Ser or absent
<220> FEATURE:
<221> NAME/KEY: VARIANT
<222> LOCATION: (78)..(78)
<223> OTHER INFORMATION: Xaa is Gly or absent
<220> FEATURE:
<221> NAME/KEY: VARIANT
<222> LOCATION: (79)..(79)
<223> OTHER INFORMATION: Xaa is Ala or absent
<220> FEATURE:
<221> NAME/KEY: VARIANT
<222> LOCATION: (80)..(80)
<223> OTHER INFORMATION: Xaa is Pro or absent
<220> FEATURE:
<221> NAME/KEY: VARIANT
<222> LOCATION: (81)..(81)
<223> OTHER INFORMATION: Xaa is Pro or absent
<220> FEATURE:
<221> NAME/KEY: VARIANT
<222> LOCATION: (82)..(82)
<223> OTHER INFORMATION: Xaa is Pro or absent
<220> FEATURE:
<221> NAME/KEY: VARIANT
<222> LOCATION: (83)..(83)
<223> OTHER INFORMATION: Xaa is Ser or absent
<220> FEATURE:
<221> NAME/KEY: VARIANT
<222> LOCATION: (84)..(84)
<223> OTHER INFORMATION: Xaa is Thr or absent.
```

```
<220> FEATURE:
<221> NAME/KEY: VARIANT
<222> LOCATION: (84)..(97)
<223> OTHER INFORMATION: If Xaa at position 84 is any of the amino acids
      listed (as in, the position is not absent), then the Xaa's from
      positions 85-97 are absent; if Xaa at position 84 is absent, then
      the Xaa's from positions 85-97 are not absent.
<220> FEATURE:
<221> NAME/KEY: VARIANT
<222> LOCATION: (85)..(85)
<223> OTHER INFORMATION: Xaa is Lys or absent
<220> FEATURE:
<221> NAME/KEY: VARIANT
<222> LOCATION: (86)..(86)
<223> OTHER INFORMATION: Xaa is Asn or absent
<220> FEATURE:
<221> NAME/KEY: VARIANT
<222> LOCATION: (87)..(87)
<223> OTHER INFORMATION: Xaa is Gly or absent
<220> FEATURE:
<221> NAME/KEY: VARIANT
<222> LOCATION: (88)..(88)
<223> OTHER INFORMATION: Xaa is Gly or absent
<220> FEATURE:
<221> NAME/KEY: VARIANT
<222> LOCATION: (89)..(89)
<223> OTHER INFORMATION: Xaa is Pro or absent
<220> FEATURE:
<221> NAME/KEY: VARIANT
<222> LOCATION: (90)..(90)
<223> OTHER INFORMATION: Xaa is Ser or absent
<220> FEATURE:
<221> NAME/KEY: VARIANT
<222> LOCATION: (91)..(91)
<223> OTHER INFORMATION: Xaa is Ser or absent
<220> FEATURE:
<221> NAME/KEY: VARIANT
<222> LOCATION: (92)..(92)
<223> OTHER INFORMATION: Xaa is Gly or absent
<220> FEATURE:
<221> NAME/KEY: VARIANT
<222> LOCATION: (93)..(93)
<223> OTHER INFORMATION: Xaa is Ala or absent
<220> FEATURE:
<221> NAME/KEY: VARIANT
<222> LOCATION: (94)..(94)
<223> OTHER INFORMATION: Xaa is Pro or absent
<220> FEATURE:
<221> NAME/KEY: VARIANT
<222> LOCATION: (95)..(95)
<223> OTHER INFORMATION: Xaa is Pro or absent
<220> FEATURE:
<221> NAME/KEY: VARIANT
<222> LOCATION: (96)..(96)
<223> OTHER INFORMATION: Xaa is Pro or absent
<220> FEATURE:
<221> NAME/KEY: VARIANT
<222> LOCATION: (97)..(97)
<223> OTHER INFORMATION: Xaa is Ser or absent
<220> FEATURE:
<221> NAME/KEY: VARIANT
<222> LOCATION: (98)..(98)
<223> OTHER INFORMATION: Xaa is Asp, Asn, or absent.
<220> FEATURE:
<221> NAME/KEY: VARIANT
<222> LOCATION: (98)..(111)
<223> OTHER INFORMATION: If Xaa at position 98 is any of the amino acids
      listed (as in, the position is not absent), then the Xaa's from
      positions 99-111 are absent; if Xaa at position 98 is absent, then
      the Xaa's from positions 99-111 are not absent.
<220> FEATURE:
<221> NAME/KEY: VARIANT
<222> LOCATION: (99)..(99)
<223> OTHER INFORMATION: Xaa is Lys or absent
<220> FEATURE:
<221> NAME/KEY: VARIANT
<222> LOCATION: (100)..(100)
<223> OTHER INFORMATION: Xaa is Asn or absent
<220> FEATURE:
```

```
<221> NAME/KEY: VARIANT
<222> LOCATION: (101)..(101)
<223> OTHER INFORMATION: Xaa is Gly or absent
<220> FEATURE:
<221> NAME/KEY: VARIANT
<222> LOCATION: (102)..(102)
<223> OTHER INFORMATION: Xaa is Gly or absent
<220> FEATURE:
<221> NAME/KEY: VARIANT
<222> LOCATION: (103)..(103)
<223> OTHER INFORMATION: Xaa is Pro or absent
<220> FEATURE:
<221> NAME/KEY: VARIANT
<222> LOCATION: (104)..(104)
<223> OTHER INFORMATION: Xaa is Ser or absent
<220> FEATURE:
<221> NAME/KEY: VARIANT
<222> LOCATION: (105)..(105)
<223> OTHER INFORMATION: Xaa is Ser or absent
<220> FEATURE:
<221> NAME/KEY: VARIANT
<222> LOCATION: (106)..(106)
<223> OTHER INFORMATION: Xaa is Gly or absent
<220> FEATURE:
<221> NAME/KEY: VARIANT
<222> LOCATION: (107)..(107)
<223> OTHER INFORMATION: Xaa is Ala or absent
<220> FEATURE:
<221> NAME/KEY: VARIANT
<222> LOCATION: (108)..(108)
<223> OTHER INFORMATION: Xaa is Pro or absent
<220> FEATURE:
<221> NAME/KEY: VARIANT
<222> LOCATION: (109)..(109)
<223> OTHER INFORMATION: Xaa is Pro or absent
<220> FEATURE:
<221> NAME/KEY: VARIANT
<222> LOCATION: (110)..(110)
<223> OTHER INFORMATION: Xaa is Pro or absent
<220> FEATURE:
<221> NAME/KEY: VARIANT
<222> LOCATION: (111)..(111)
<223> OTHER INFORMATION: Xaa is Ser or absent
<220> FEATURE:
<221> NAME/KEY: VARIANT
<222> LOCATION: (112)..(112)
<223> OTHER INFORMATION: Xaa is Lys or absent
<220> FEATURE:
<221> NAME/KEY: VARIANT
<222> LOCATION: (112)..(124)
<223> OTHER INFORMATION: If Xaa at position 112 is absent, then Xaa's
      from positions 113-124 are also absent; if Xaa at position 112 is
      not absent, then Xaa's from positions 113-124 are also not absent.
<220> FEATURE:
<221> NAME/KEY: VARIANT
<222> LOCATION: (113)..(113)
<223> OTHER INFORMATION: Xaa is Asn or absent
<220> FEATURE:
<221> NAME/KEY: VARIANT
<222> LOCATION: (114)..(114)
<223> OTHER INFORMATION: Xaa is Gly or absent
<220> FEATURE:
<221> NAME/KEY: VARIANT
<222> LOCATION: (115)..(115)
<223> OTHER INFORMATION: Xaa is Gly or absent
<220> FEATURE:
<221> NAME/KEY: VARIANT
<222> LOCATION: (116)..(116)
<223> OTHER INFORMATION: Xaa is Pro or absent
<220> FEATURE:
<221> NAME/KEY: VARIANT
<222> LOCATION: (117)..(117)
<223> OTHER INFORMATION: Xaa is Ser or absent
<220> FEATURE:
<221> NAME/KEY: VARIANT
<222> LOCATION: (118)..(118)
<223> OTHER INFORMATION: Xaa is Ser or absent
<220> FEATURE:
<221> NAME/KEY: VARIANT
```

<222> LOCATION: (119)..(119)
<223> OTHER INFORMATION: Xaa is Gly or absent
<220> FEATURE:
<221> NAME/KEY: VARIANT
<222> LOCATION: (120)..(120)
<223> OTHER INFORMATION: Xaa is Ala or absent
<220> FEATURE:
<221> NAME/KEY: VARIANT
<222> LOCATION: (121)..(121)
<223> OTHER INFORMATION: Xaa is Pro or absent
<220> FEATURE:
<221> NAME/KEY: VARIANT
<222> LOCATION: (122)..(122)
<223> OTHER INFORMATION: Xaa is Pro or absent
<220> FEATURE:
<221> NAME/KEY: VARIANT
<222> LOCATION: (123)..(123)
<223> OTHER INFORMATION: Xaa is Pro or absent
<220> FEATURE:
<221> NAME/KEY: VARIANT
<222> LOCATION: (124)..(124)
<223> OTHER INFORMATION: Xaa is Ser or absent

<400> SEQUENCE: 8

His Xaa Xaa Gly Xaa Phe Xaa Xaa Xaa Xaa Xaa Xaa Leu Xaa Xaa
1               5                   10                  15

Xaa Ala Ala Xaa Xaa Phe Ile Xaa Trp Leu Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa
        115                 120

<210> SEQ ID NO 9
<211> LENGTH: 110
<212> TYPE: PRT
<213> ORGANISM: Artificial sequence
<220> FEATURE:
<223> OTHER INFORMATION: Synthetic sequence: GLP-2 analogue: General
      Formula II of PCT/EP2013/059320
<220> FEATURE:
<221> NAME/KEY: VARIANT
<222> LOCATION: (2)..(2)
<223> OTHER INFORMATION: Xaa is Gly, Ala or Aib
<220> FEATURE:
<221> NAME/KEY: VARIANT
<222> LOCATION: (3)..(3)
<223> OTHER INFORMATION: Xaa is Glu, Gln or Asp
<220> FEATURE:
<221> NAME/KEY: VARIANT
<222> LOCATION: (5)..(5)
<223> OTHER INFORMATION: Xaa is Ser or Thr
<220> FEATURE:
<221> NAME/KEY: VARIANT
<222> LOCATION: (7)..(7)
<223> OTHER INFORMATION: Xaa is Ser or Thr
<220> FEATURE:
<221> NAME/KEY: VARIANT
<222> LOCATION: (12)..(12)
<223> OTHER INFORMATION: Xaa is Thr, Ser or Lys
<220> FEATURE:
<221> NAME/KEY: VARIANT -continued

```
<222> LOCATION: (13)..(13)
<223> OTHER INFORMATION: Xaa is Ile, Leu, Val, Tyr, Phe or Gln
<220> FEATURE:
<221> NAME/KEY: VARIANT
<222> LOCATION: (14)..(14)
<223> OTHER INFORMATION: Xaa is Leu or Met
<220> FEATURE:
<221> NAME/KEY: VARIANT
<222> LOCATION: (15)..(15)
<223> OTHER INFORMATION: Xaa is Asp or Glu
<220> FEATURE:
<221> NAME/KEY: VARIANT
<222> LOCATION: (16)..(16)
<223> OTHER INFORMATION: Xaa is Gly, Ser, Ala, Glu or Lys
<220> FEATURE:
<221> NAME/KEY: VARIANT
<222> LOCATION: (17)..(17)
<223> OTHER INFORMATION: Xaa is Gln or Lys
<220> FEATURE:
<221> NAME/KEY: VARIANT
<222> LOCATION: (19)..(19)
<223> OTHER INFORMATION: Xaa is Ala or Val
<220> FEATURE:
<221> NAME/KEY: VARIANT
<222> LOCATION: (20)..(20)
<223> OTHER INFORMATION: Xaa is Arg, Lys or His
<220> FEATURE:
<221> NAME/KEY: VARIANT
<222> LOCATION: (21)..(21)
<223> OTHER INFORMATION: Xaa is Asp, Glu or Leu
<220> FEATURE:
<221> NAME/KEY: VARIANT
<222> LOCATION: (24)..(24)
<223> OTHER INFORMATION: Xaa is Asn, Ala, Glu or Lys
<220> FEATURE:
<221> NAME/KEY: VARIANT
<222> LOCATION: (27)..(27)
<223> OTHER INFORMATION: Xaa is Ile, Leu, Val, Glu or Lys
<220> FEATURE:
<221> NAME/KEY: VARIANT
<222> LOCATION: (28)..(28)
<223> OTHER INFORMATION: Xaa is Gln, Asn, Lys, Ser, Gly, or absent.
<220> FEATURE:
<221> NAME/KEY: VARIANT
<222> LOCATION: (28)..(39)
<223> OTHER INFORMATION: If Xaa at position 28 is any of the amino acids
      listed (as in, the position is not absent), then the Xaa's from
      positions 29-39 are absent; if Xaa at position 28 is absent, then
      the Xaa's from positions 29-39 are not absent.
<220> FEATURE:
<221> NAME/KEY: VARIANT
<222> LOCATION: (29)..(110)
<223> OTHER INFORMATION: If Xaas from position 29-39 are present, then
      all Xaas from position 40-110 are absent.
<220> FEATURE:
<221> NAME/KEY: VARIANT
<222> LOCATION: (29)..(29)
<223> OTHER INFORMATION: Xaa is Gly or absent
<220> FEATURE:
<221> NAME/KEY: VARIANT
<222> LOCATION: (30)..(30)
<223> OTHER INFORMATION: Xaa is Gly or absent
<220> FEATURE:
<221> NAME/KEY: VARIANT
<222> LOCATION: (31)..(31)
<223> OTHER INFORMATION: Xaa is Pro or absent
<220> FEATURE:
<221> NAME/KEY: VARIANT
<222> LOCATION: (32)..(32)
<223> OTHER INFORMATION: Xaa is Ser or absent
<220> FEATURE:
<221> NAME/KEY: VARIANT
<222> LOCATION: (33)..(33)
<223> OTHER INFORMATION: Xaa is Ser or absent
<220> FEATURE:
<221> NAME/KEY: VARIANT
<222> LOCATION: (34)..(34)
<223> OTHER INFORMATION: Xaa is Gly or absent
<220> FEATURE:
```

```
<221> NAME/KEY: VARIANT
<222> LOCATION: (35)..(35)
<223> OTHER INFORMATION: Xaa is Ala or absent
<220> FEATURE:
<221> NAME/KEY: VARIANT
<222> LOCATION: (36)..(36)
<223> OTHER INFORMATION: Xaa is Pro or absent
<220> FEATURE:
<221> NAME/KEY: VARIANT
<222> LOCATION: (37)..(37)
<223> OTHER INFORMATION: Xaa is Pro or absent
<220> FEATURE:
<221> NAME/KEY: VARIANT
<222> LOCATION: (38)..(38)
<223> OTHER INFORMATION: Xaa is Pro or absent
<220> FEATURE:
<221> NAME/KEY: VARIANT
<222> LOCATION: (39)..(39)
<223> OTHER INFORMATION: Xaa is Ser or absent
<220> FEATURE:
<221> NAME/KEY: VARIANT
<222> LOCATION: (40)..(40)
<223> OTHER INFORMATION: Xaa is Thr, Ala, or absent.
<220> FEATURE:
<221> NAME/KEY: VARIANT
<222> LOCATION: (40)..(51)
<223> OTHER INFORMATION: If Xaa at position 40 is any of the amino acids
      listed (as in, the position is not absent), then the Xaa's from
      positions 41-51 are absent; if Xaa at position 40 is absent, then
      the Xaa's from positions 41-51 are not absent.
<220> FEATURE:
<221> NAME/KEY: VARIANT
<222> LOCATION: (41)..(110)
<223> OTHER INFORMATION: If Xaas from position 41-51 are present, then
      all Xaas from position 52-110 are absent.
<220> FEATURE:
<221> NAME/KEY: VARIANT
<222> LOCATION: (41)..(41)
<223> OTHER INFORMATION: Xaa is Gly or absent
<220> FEATURE:
<221> NAME/KEY: VARIANT
<222> LOCATION: (42)..(42)
<223> OTHER INFORMATION: Xaa is Gly or absent
<220> FEATURE:
<221> NAME/KEY: VARIANT
<222> LOCATION: (43)..(43)
<223> OTHER INFORMATION: Xaa is Pro or absent
<220> FEATURE:
<221> NAME/KEY: VARIANT
<222> LOCATION: (44)..(44)
<223> OTHER INFORMATION: Xaa is Ser or absent
<220> FEATURE:
<221> NAME/KEY: VARIANT
<222> LOCATION: (45)..(45)
<223> OTHER INFORMATION: Xaa is Ser or absent
<220> FEATURE:
<221> NAME/KEY: VARIANT
<222> LOCATION: (46)..(46)
<223> OTHER INFORMATION: Xaa is Gly or absent
<220> FEATURE:
<221> NAME/KEY: VARIANT
<222> LOCATION: (47)..(47)
<223> OTHER INFORMATION: Xaa is Ala or absent
<220> FEATURE:
<221> NAME/KEY: VARIANT
<222> LOCATION: (48)..(48)
<223> OTHER INFORMATION: Xaa is Pro or absent
<220> FEATURE:
<221> NAME/KEY: VARIANT
<222> LOCATION: (49)..(49)
<223> OTHER INFORMATION: Xaa is Pro or absent
<220> FEATURE:
<221> NAME/KEY: VARIANT
<222> LOCATION: (50)..(50)
<223> OTHER INFORMATION: Xaa is Pro or absent
<220> FEATURE:
<221> NAME/KEY: VARIANT
<222> LOCATION: (51)..(51)
<223> OTHER INFORMATION: Xaa is Ser or absent
```

```
<220> FEATURE:
<221> NAME/KEY: VARIANT
<222> LOCATION: (52)..(52)
<223> OTHER INFORMATION: Xaa is Lys or absent.
<220> FEATURE:
<221> NAME/KEY: VARIANT
<222> LOCATION: (52)..(63)
<223> OTHER INFORMATION: If Xaa at position 52 is any of the amino acids
      listed (as in, the position is not absent), then the Xaa's from
      positions 53-63 are absent; if Xaa at position 52 is absent, then
      the Xaa's from positions 53-63 are not absent.
<220> FEATURE:
<221> NAME/KEY: VARIANT
<222> LOCATION: (53)..(110)
<223> OTHER INFORMATION: If Xaas from position53-63 are present, then
      all Xaas from position 64-110 are absent.
<220> FEATURE:
<221> NAME/KEY: VARIANT
<222> LOCATION: (53)..(53)
<223> OTHER INFORMATION: Xaa is Gly or absent
<220> FEATURE:
<221> NAME/KEY: VARIANT
<222> LOCATION: (54)..(54)
<223> OTHER INFORMATION: Xaa is Gly or absent
<220> FEATURE:
<221> NAME/KEY: VARIANT
<222> LOCATION: (55)..(55)
<223> OTHER INFORMATION: Xaa is Pro or absent
<220> FEATURE:
<221> NAME/KEY: VARIANT
<222> LOCATION: (56)..(56)
<223> OTHER INFORMATION: Xaa is Ser or absent
<220> FEATURE:
<221> NAME/KEY: VARIANT
<222> LOCATION: (57)..(57)
<223> OTHER INFORMATION: Xaa is Ser or absent
<220> FEATURE:
<221> NAME/KEY: VARIANT
<222> LOCATION: (58)..(58)
<223> OTHER INFORMATION: Xaa is Gly or absent
<220> FEATURE:
<221> NAME/KEY: VARIANT
<222> LOCATION: (59)..(59)
<223> OTHER INFORMATION: Xaa is Ala or absent
<220> FEATURE:
<221> NAME/KEY: VARIANT
<222> LOCATION: (60)..(60)
<223> OTHER INFORMATION: Xaa is Pro or absent
<220> FEATURE:
<221> NAME/KEY: VARIANT
<222> LOCATION: (61)..(61)
<223> OTHER INFORMATION: Xaa is Pro or absent
<220> FEATURE:
<221> NAME/KEY: VARIANT
<222> LOCATION: (62)..(62)
<223> OTHER INFORMATION: Xaa is Pro or absent
<220> FEATURE:
<221> NAME/KEY: VARIANT
<222> LOCATION: (63)..(63)
<223> OTHER INFORMATION: Xaa is Ser or absent
<220> FEATURE:
<221> NAME/KEY: VARIANT
<222> LOCATION: (64)..(64)
<223> OTHER INFORMATION: Xaa is Ile, Pro, or absent.
<220> FEATURE:
<221> NAME/KEY: VARIANT
<222> LOCATION: (64)..(75)
<223> OTHER INFORMATION: If Xaa at position 64 is any of the amino acids
      listed (as in, the position is not absent), then the Xaa's from
      positions 65-75 are absent; if Xaa at position 64 is absent, then
      the Xaa's from positions 65-75 are not absent.
<220> FEATURE:
<221> NAME/KEY: VARIANT
<222> LOCATION: (65)..(110)
<223> OTHER INFORMATION: If Xaas from position 65-75 are present, then
      all Xaas from position 76-110 are absent.
<220> FEATURE:
<221> NAME/KEY: VARIANT
<222> LOCATION: (65)..(65)
```

```
<223> OTHER INFORMATION: Xaa is Gly or absent
<220> FEATURE:
<221> NAME/KEY: VARIANT
<222> LOCATION: (66)..(66)
<223> OTHER INFORMATION: Xaa is Gly or absent
<220> FEATURE:
<221> NAME/KEY: VARIANT
<222> LOCATION: (67)..(67)
<223> OTHER INFORMATION: Xaa is Pro or absent
<220> FEATURE:
<221> NAME/KEY: VARIANT
<222> LOCATION: (68)..(68)
<223> OTHER INFORMATION: Xaa is Ser or absent
<220> FEATURE:
<221> NAME/KEY: VARIANT
<222> LOCATION: (69)..(69)
<223> OTHER INFORMATION: Xaa is Ser or absent
<220> FEATURE:
<221> NAME/KEY: VARIANT
<222> LOCATION: (70)..(70)
<223> OTHER INFORMATION: Xaa is Gly or absent
<220> FEATURE:
<221> NAME/KEY: VARIANT
<222> LOCATION: (71)..(71)
<223> OTHER INFORMATION: Xaa is Ala or absent
<220> FEATURE:
<221> NAME/KEY: VARIANT
<222> LOCATION: (72)..(72)
<223> OTHER INFORMATION: Xaa is Pro or absent
<220> FEATURE:
<221> NAME/KEY: VARIANT
<222> LOCATION: (73)..(73)
<223> OTHER INFORMATION: Xaa is Pro or absent
<220> FEATURE:
<221> NAME/KEY: VARIANT
<222> LOCATION: (74)..(74)
<223> OTHER INFORMATION: Xaa is Pro or absent
<220> FEATURE:
<221> NAME/KEY: VARIANT
<222> LOCATION: (75)..(75)
<223> OTHER INFORMATION: Xaa is Ser or absent
<220> FEATURE:
<221> NAME/KEY: VARIANT
<222> LOCATION: (76)..(76)
<223> OTHER INFORMATION: Xaa is Thr or absent.
<220> FEATURE:
<221> NAME/KEY: VARIANT
<222> LOCATION: (76)..(87)
<223> OTHER INFORMATION: If Xaa at position 76 is any of the amino acids
      listed (as in, the position is not absent), then the Xaa's from
      positions 77-87 are absent; if Xaa at position 76 is absent, then
      the Xaa's from positions 77-87 are not absent.
<220> FEATURE:
<221> NAME/KEY: VARIANT
<222> LOCATION: (77)..(110)
<223> OTHER INFORMATION: If Xaas from position 77-87 are present, then
      all Xaas from position 88-110 are absent.
<220> FEATURE:
<221> NAME/KEY: VARIANT
<222> LOCATION: (77)..(77)
<223> OTHER INFORMATION: Xaa is Gly or absent
<220> FEATURE:
<221> NAME/KEY: VARIANT
<222> LOCATION: (78)..(78)
<223> OTHER INFORMATION: Xaa is Gly or absent
<220> FEATURE:
<221> NAME/KEY: VARIANT
<222> LOCATION: (79)..(79)
<223> OTHER INFORMATION: Xaa is Pro or absent
<220> FEATURE:
<221> NAME/KEY: VARIANT
<222> LOCATION: (80)..(80)
<223> OTHER INFORMATION: Xaa is Ser or absent
<220> FEATURE:
<221> NAME/KEY: VARIANT
<222> LOCATION: (81)..(81)
<223> OTHER INFORMATION: Xaa is Ser or absent
<220> FEATURE:
<221> NAME/KEY: VARIANT
```

```
<222> LOCATION: (82)..(82)
<223> OTHER INFORMATION: Xaa is Gly or absent
<220> FEATURE:
<221> NAME/KEY: VARIANT
<222> LOCATION: (83)..(83)
<223> OTHER INFORMATION: Xaa is Ala or absent
<220> FEATURE:
<221> NAME/KEY: VARIANT
<222> LOCATION: (84)..(84)
<223> OTHER INFORMATION: Xaa is Pro or absent
<220> FEATURE:
<221> NAME/KEY: VARIANT
<222> LOCATION: (85)..(85)
<223> OTHER INFORMATION: Xaa is Pro or absent
<220> FEATURE:
<221> NAME/KEY: VARIANT
<222> LOCATION: (86)..(86)
<223> OTHER INFORMATION: Xaa is Pro or absent
<220> FEATURE:
<221> NAME/KEY: VARIANT
<222> LOCATION: (87)..(87)
<223> OTHER INFORMATION: Xaa is Ser or absent
<220> FEATURE:
<221> NAME/KEY: VARIANT
<222> LOCATION: (88)..(88)
<223> OTHER INFORMATION: Xaa is Asp, Asn, or absent.
<220> FEATURE:
<221> NAME/KEY: VARIANT
<222> LOCATION: (88)..(99)
<223> OTHER INFORMATION: If Xaa at position 88 is any of the amino acids
      listed (as in, the position is not absent), then the Xaa's from
      positions 89-99 are absent; if Xaa at position 88 is absent, then
      the Xaa's from positions 89-99 are not absent.
<220> FEATURE:
<221> NAME/KEY: VARIANT
<222> LOCATION: (89)..(110)
<223> OTHER INFORMATION: If Xaas from position 89-99 are present, then
      all Xaas from position 100-110 are absent.
<220> FEATURE:
<221> NAME/KEY: VARIANT
<222> LOCATION: (89)..(89)
<223> OTHER INFORMATION: Xaa is Gly or absent
<220> FEATURE:
<221> NAME/KEY: VARIANT
<222> LOCATION: (90)..(90)
<223> OTHER INFORMATION: Xaa is Gly or absent
<220> FEATURE:
<221> NAME/KEY: VARIANT
<222> LOCATION: (91)..(91)
<223> OTHER INFORMATION: Xaa is Pro or absent
<220> FEATURE:
<221> NAME/KEY: VARIANT
<222> LOCATION: (92)..(92)
<223> OTHER INFORMATION: Xaa is Ser or absent
<220> FEATURE:
<221> NAME/KEY: VARIANT
<222> LOCATION: (93)..(93)
<223> OTHER INFORMATION: Xaa is Ser or absent
<220> FEATURE:
<221> NAME/KEY: VARIANT
<222> LOCATION: (94)..(94)
<223> OTHER INFORMATION: Xaa is Gly or absent
<220> FEATURE:
<221> NAME/KEY: VARIANT
<222> LOCATION: (95)..(95)
<223> OTHER INFORMATION: Xaa is Ala or absent
<220> FEATURE:
<221> NAME/KEY: VARIANT
<222> LOCATION: (96)..(96)
<223> OTHER INFORMATION: Xaa is Pro or absent
<220> FEATURE:
<221> NAME/KEY: VARIANT
<222> LOCATION: (97)..(97)
<223> OTHER INFORMATION: Xaa is Pro or absent
<220> FEATURE:
<221> NAME/KEY: VARIANT
<222> LOCATION: (98)..(98)
<223> OTHER INFORMATION: Xaa is Pro or absent
<220> FEATURE:
```

```
<221> NAME/KEY: VARIANT
<222> LOCATION: (99)..(99)
<223> OTHER INFORMATION: Xaa is Ser or absent
<220> FEATURE:
<221> NAME/KEY: VARIANT
<222> LOCATION: (100)..(100)
<223> OTHER INFORMATION: Xaa is Gly or absent
<220> FEATURE:
<221> NAME/KEY: VARIANT
<222> LOCATION: (100)..(110)
<223> OTHER INFORMATION: If Xaa at position 100 is absent, then Xaa's
      from positions 101-110 are also absent; if Xaa at position 100 is
      not absent, then Xaa's from positions 101-110 are also not absent.
<220> FEATURE:
<221> NAME/KEY: VARIANT
<222> LOCATION: (101)..(101)
<223> OTHER INFORMATION: Xaa is Gly or absent
<220> FEATURE:
<221> NAME/KEY: VARIANT
<222> LOCATION: (102)..(102)
<223> OTHER INFORMATION: Xaa is Pro or absent
<220> FEATURE:
<221> NAME/KEY: VARIANT
<222> LOCATION: (103)..(103)
<223> OTHER INFORMATION: Xaa is Ser or absent
<220> FEATURE:
<221> NAME/KEY: VARIANT
<222> LOCATION: (104)..(104)
<223> OTHER INFORMATION: Xaa is Ser or absent
<220> FEATURE:
<221> NAME/KEY: VARIANT
<222> LOCATION: (105)..(105)
<223> OTHER INFORMATION: Xaa is Gly or absent
<220> FEATURE:
<221> NAME/KEY: VARIANT
<222> LOCATION: (106)..(106)
<223> OTHER INFORMATION: Xaa is Ala or absent
<220> FEATURE:
<221> NAME/KEY: VARIANT
<222> LOCATION: (107)..(107)
<223> OTHER INFORMATION: Xaa is Pro or absent
<220> FEATURE:
<221> NAME/KEY: VARIANT
<222> LOCATION: (108)..(108)
<223> OTHER INFORMATION: Xaa is Pro or absent
<220> FEATURE:
<221> NAME/KEY: VARIANT
<222> LOCATION: (109)..(109)
<223> OTHER INFORMATION: Xaa is Pro or absent
<220> FEATURE:
<221> NAME/KEY: VARIANT
<222> LOCATION: (110)..(110)
<223> OTHER INFORMATION: Xaa is Ser or absent

<400> SEQUENCE: 9

His Xaa Xaa Gly Xaa Phe Xaa Ser Glu Leu Ala Xaa Xaa Xaa Xaa Xaa
1               5                   10                  15

Xaa Ala Xaa Xaa Xaa Phe Ile Xaa Trp Leu Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa
            100                 105                 110

<210> SEQ ID NO 10
```

```
<211> LENGTH: 124
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (2)..(2)
<223> OTHER INFORMATION: Xaa is Gly, Ala or Aib
<220> FEATURE:
<221> NAME/KEY: VARIANT
<222> LOCATION: (3)..(3)
<223> OTHER INFORMATION: Xaa is Glu, Gln or Asp
<220> FEATURE:
<221> NAME/KEY: VARIANT
<222> LOCATION: (5)..(5)
<223> OTHER INFORMATION: Xaa is Ser or Thr
<220> FEATURE:
<221> NAME/KEY: VARIANT
<222> LOCATION: (7)..(7)
<223> OTHER INFORMATION: Xaa is Ser or Thr
<220> FEATURE:
<221> NAME/KEY: VARIANT
<222> LOCATION: (12)..(12)
<223> OTHER INFORMATION: Xaa is Thr, Ser or Lys
<220> FEATURE:
<221> NAME/KEY: VARIANT
<222> LOCATION: (13)..(13)
<223> OTHER INFORMATION: Xaa is Ile, Leu, Val, Tyr, Phe or Gln
<220> FEATURE:
<221> NAME/KEY: VARIANT
<222> LOCATION: (14)..(14)
<223> OTHER INFORMATION: Xaa is Leu or Met
<220> FEATURE:
<221> NAME/KEY: VARIANT
<222> LOCATION: (15)..(15)
<223> OTHER INFORMATION: Xaa is Asp or Glu
<220> FEATURE:
<221> NAME/KEY: VARIANT
<222> LOCATION: (16)..(16)
<223> OTHER INFORMATION: Xaa is Gly, Ser, Ala, Glu or Lys
<220> FEATURE:
<221> NAME/KEY: VARIANT
<222> LOCATION: (17)..(17)
<223> OTHER INFORMATION: Xaa is Gln or Lys
<220> FEATURE:
<221> NAME/KEY: VARIANT
<222> LOCATION: (19)..(19)
<223> OTHER INFORMATION: Xaa is Ala or Val
<220> FEATURE:
<221> NAME/KEY: VARIANT
<222> LOCATION: (20)..(20)
<223> OTHER INFORMATION: Xaa is Arg, Lys or His
<220> FEATURE:
<221> NAME/KEY: VARIANT
<222> LOCATION: (21)..(21)
<223> OTHER INFORMATION: Xaa is Asp, Glu or Leu
<220> FEATURE:
<221> NAME/KEY: VARIANT
<222> LOCATION: (24)..(24)
<223> OTHER INFORMATION: Xaa is Asn, Ala, Glu or Lys
<220> FEATURE:
<221> NAME/KEY: VARIANT
<222> LOCATION: (27)..(27)
<223> OTHER INFORMATION: Xaa is Ile, Leu, Val, Glu or Lys
<220> FEATURE:
<221> NAME/KEY: VARIANT
<222> LOCATION: (28)..(28)
<223> OTHER INFORMATION: Xaa is Gln, Asn, Lys, Ser, Gly, or absent.
<220> FEATURE:
<221> NAME/KEY: VARIANT
<222> LOCATION: (28)..(41)
<223> OTHER INFORMATION: If Xaa at position 28 is any of the amino acids
    listed (as in, the position is not absent), then the Xaa's from
    positions 29-41 are absent; if Xaa at position 28 is absent, then
    the Xaa's from positions 29-41 are not absent.
<220> FEATURE:
<221> NAME/KEY: VARIANT
<222> LOCATION: (29)..(124)
```

```
<223> OTHER INFORMATION: If Xaas from position 29-41 are present, then
      all Xaas from position 42-124 are absent.
<220> FEATURE:
<221> NAME/KEY: VARIANT
<222> LOCATION: (29)..(29)
<223> OTHER INFORMATION: Xaa is Lys or absent
<220> FEATURE:
<221> NAME/KEY: VARIANT
<222> LOCATION: (30)..(30)
<223> OTHER INFORMATION: Xaa is Asn or absent
<220> FEATURE:
<221> NAME/KEY: VARIANT
<222> LOCATION: (31)..(31)
<223> OTHER INFORMATION: Xaa is Gly or absent
<220> FEATURE:
<221> NAME/KEY: VARIANT
<222> LOCATION: (32)..(32)
<223> OTHER INFORMATION: Xaa is Gly or absent
<220> FEATURE:
<221> NAME/KEY: VARIANT
<222> LOCATION: (33)..(33)
<223> OTHER INFORMATION: Xaa is Pro or absent
<220> FEATURE:
<221> NAME/KEY: VARIANT
<222> LOCATION: (34)..(34)
<223> OTHER INFORMATION: Xaa is Ser or absent
<220> FEATURE:
<221> NAME/KEY: VARIANT
<222> LOCATION: (35)..(35)
<223> OTHER INFORMATION: Xaa is Ser or absent
<220> FEATURE:
<221> NAME/KEY: VARIANT
<222> LOCATION: (36)..(36)
<223> OTHER INFORMATION: Xaa is Gly or absent
<220> FEATURE:
<221> NAME/KEY: VARIANT
<222> LOCATION: (37)..(37)
<223> OTHER INFORMATION: Xaa is Ala or absent
<220> FEATURE:
<221> NAME/KEY: VARIANT
<222> LOCATION: (38)..(38)
<223> OTHER INFORMATION: Xaa is Pro or absent
<220> FEATURE:
<221> NAME/KEY: VARIANT
<222> LOCATION: (39)..(39)
<223> OTHER INFORMATION: Xaa is Pro or absent
<220> FEATURE:
<221> NAME/KEY: VARIANT
<222> LOCATION: (40)..(40)
<223> OTHER INFORMATION: Xaa is Pro or absent
<220> FEATURE:
<221> NAME/KEY: VARIANT
<222> LOCATION: (41)..(41)
<223> OTHER INFORMATION: Xaa is Ser or absent
<220> FEATURE:
<221> NAME/KEY: VARIANT
<222> LOCATION: (42)..(42)
<223> OTHER INFORMATION: Xaa is Thr, Ala, or absent.
<220> FEATURE:
<221> NAME/KEY: VARIANT
<222> LOCATION: (42)..(55)
<223> OTHER INFORMATION: If Xaa at position 42 is any of the amino acids
      listed (as in, the position is not absent), then the Xaa's from
      positions 43-55 are absent; if Xaa at position 42 is absent, then
      the Xaa's from positions 43-55 are not absent.
<220> FEATURE:
<221> NAME/KEY: VARIANT
<222> LOCATION: (43)..(124)
<223> OTHER INFORMATION: If Xaas from position 43-55 are present, then
      all Xaas from position 56-124 are absent.
<220> FEATURE:
<221> NAME/KEY: VARIANT
<222> LOCATION: (43)..(43)
<223> OTHER INFORMATION: Xaa is Lys or absent
<220> FEATURE:
<221> NAME/KEY: VARIANT
<222> LOCATION: (44)..(44)
<223> OTHER INFORMATION: Xaa is Asn or absent
<220> FEATURE:
```

```
<221> NAME/KEY: VARIANT
<222> LOCATION: (45)..(45)
<223> OTHER INFORMATION: Xaa is Gly or absent
<220> FEATURE:
<221> NAME/KEY: VARIANT
<222> LOCATION: (46)..(46)
<223> OTHER INFORMATION: Xaa is Gly or absent
<220> FEATURE:
<221> NAME/KEY: VARIANT
<222> LOCATION: (47)..(47)
<223> OTHER INFORMATION: Xaa is Pro or absent
<220> FEATURE:
<221> NAME/KEY: VARIANT
<222> LOCATION: (48)..(48)
<223> OTHER INFORMATION: Xaa is Ser or absent
<220> FEATURE:
<221> NAME/KEY: VARIANT
<222> LOCATION: (49)..(49)
<223> OTHER INFORMATION: Xaa is Ser or absent
<220> FEATURE:
<221> NAME/KEY: VARIANT
<222> LOCATION: (50)..(50)
<223> OTHER INFORMATION: Xaa is Gly or absent
<220> FEATURE:
<221> NAME/KEY: VARIANT
<222> LOCATION: (51)..(51)
<223> OTHER INFORMATION: Xaa is Ala or absent
<220> FEATURE:
<221> NAME/KEY: VARIANT
<222> LOCATION: (52)..(52)
<223> OTHER INFORMATION: Xaa is Pro or absent
<220> FEATURE:
<221> NAME/KEY: VARIANT
<222> LOCATION: (53)..(53)
<223> OTHER INFORMATION: Xaa is Pro or absent
<220> FEATURE:
<221> NAME/KEY: VARIANT
<222> LOCATION: (54)..(54)
<223> OTHER INFORMATION: Xaa is Pro or absent
<220> FEATURE:
<221> NAME/KEY: VARIANT
<222> LOCATION: (55)..(55)
<223> OTHER INFORMATION: Xaa is Ser or absent
<220> FEATURE:
<221> NAME/KEY: VARIANT
<222> LOCATION: (56)..(56)
<223> OTHER INFORMATION: Xaa is Lys or absent.
<220> FEATURE:
<221> NAME/KEY: VARIANT
<222> LOCATION: (56)..(69)
<223> OTHER INFORMATION: If Xaa at position 56 is any of the amino acids
      listed (as in, the position is not absent), then the Xaa's from
      positions 57-69 are absent; if Xaa at position 56 is absent, then
      the Xaa's from positions 57-69 are not absent.
<220> FEATURE:
<221> NAME/KEY: VARIANT
<222> LOCATION: (57)..(124)
<223> OTHER INFORMATION: If Xaas from position 57-69 are present, then
      all Xaas from position 70-124 are absent.
<220> FEATURE:
<221> NAME/KEY: VARIANT
<222> LOCATION: (57)..(57)
<223> OTHER INFORMATION: Xaa is Lys or absent
<220> FEATURE:
<221> NAME/KEY: VARIANT
<222> LOCATION: (58)..(58)
<223> OTHER INFORMATION: Xaa is Asn or absent
<220> FEATURE:
<221> NAME/KEY: VARIANT
<222> LOCATION: (59)..(59)
<223> OTHER INFORMATION: Xaa is Gly or absent
<220> FEATURE:
<221> NAME/KEY: VARIANT
<222> LOCATION: (60)..(60)
<223> OTHER INFORMATION: Xaa is Gly or absent
<220> FEATURE:
<221> NAME/KEY: VARIANT
<222> LOCATION: (61)..(61)
<223> OTHER INFORMATION: Xaa is Pro or absent
```

```
<220> FEATURE:
<221> NAME/KEY: VARIANT
<222> LOCATION: (62)..(62)
<223> OTHER INFORMATION: Xaa is Ser or absent
<220> FEATURE:
<221> NAME/KEY: VARIANT
<222> LOCATION: (63)..(63)
<223> OTHER INFORMATION: Xaa is Ser or absent
<220> FEATURE:
<221> NAME/KEY: VARIANT
<222> LOCATION: (64)..(64)
<223> OTHER INFORMATION: Xaa is Gly or absent
<220> FEATURE:
<221> NAME/KEY: VARIANT
<222> LOCATION: (65)..(65)
<223> OTHER INFORMATION: Xaa is Ala or absent
<220> FEATURE:
<221> NAME/KEY: VARIANT
<222> LOCATION: (66)..(66)
<223> OTHER INFORMATION: Xaa is Pro or absent
<220> FEATURE:
<221> NAME/KEY: VARIANT
<222> LOCATION: (67)..(67)
<223> OTHER INFORMATION: Xaa is Pro or absent
<220> FEATURE:
<221> NAME/KEY: VARIANT
<222> LOCATION: (68)..(68)
<223> OTHER INFORMATION: Xaa is Pro or absent
<220> FEATURE:
<221> NAME/KEY: VARIANT
<222> LOCATION: (69)..(69)
<223> OTHER INFORMATION: Xaa is Ser or absent
<220> FEATURE:
<221> NAME/KEY: VARIANT
<222> LOCATION: (70)..(70)
<223> OTHER INFORMATION: Xaa is Ile, Pro, or absent.
<220> FEATURE:
<221> NAME/KEY: VARIANT
<222> LOCATION: (70)..(83)
<223> OTHER INFORMATION: If Xaa at position 70 is any of the amino acids
      listed (as in, the position is not absent), then the Xaa's from
      positions 71-83 are absent; if Xaa at position 70 is absent, then
      the Xaa's from positions 71-83 are not absent.
<220> FEATURE:
<221> NAME/KEY: VARIANT
<222> LOCATION: (71)..(124)
<223> OTHER INFORMATION: If Xaas from position 71-83 are present, then
      all Xaas from position 84-124 are absent.
<220> FEATURE:
<221> NAME/KEY: VARIANT
<222> LOCATION: (71)..(71)
<223> OTHER INFORMATION: Xaa is Lys or absent
<220> FEATURE:
<221> NAME/KEY: VARIANT
<222> LOCATION: (72)..(72)
<223> OTHER INFORMATION: Xaa is Asn or absent
<220> FEATURE:
<221> NAME/KEY: VARIANT
<222> LOCATION: (73)..(73)
<223> OTHER INFORMATION: Xaa is Gly or absent
<220> FEATURE:
<221> NAME/KEY: VARIANT
<222> LOCATION: (74)..(74)
<223> OTHER INFORMATION: Xaa is Gly or absent
<220> FEATURE:
<221> NAME/KEY: VARIANT
<222> LOCATION: (75)..(75)
<223> OTHER INFORMATION: Xaa is Pro or absent
<220> FEATURE:
<221> NAME/KEY: VARIANT
<222> LOCATION: (76)..(76)
<223> OTHER INFORMATION: Xaa is Ser or absent
<220> FEATURE:
<221> NAME/KEY: VARIANT
<222> LOCATION: (77)..(77)
<223> OTHER INFORMATION: Xaa is Ser or absent
<220> FEATURE:
<221> NAME/KEY: VARIANT
<222> LOCATION: (78)..(78)
```

```
<223> OTHER INFORMATION: Xaa is Gly or absent
<220> FEATURE:
<221> NAME/KEY: VARIANT
<222> LOCATION: (79)..(79)
<223> OTHER INFORMATION: Xaa is Ala or absent
<220> FEATURE:
<221> NAME/KEY: VARIANT
<222> LOCATION: (80)..(80)
<223> OTHER INFORMATION: Xaa is Pro or absent
<220> FEATURE:
<221> NAME/KEY: VARIANT
<222> LOCATION: (81)..(81)
<223> OTHER INFORMATION: Xaa is Pro or absent
<220> FEATURE:
<221> NAME/KEY: VARIANT
<222> LOCATION: (82)..(82)
<223> OTHER INFORMATION: Xaa is Pro or absent
<220> FEATURE:
<221> NAME/KEY: VARIANT
<222> LOCATION: (83)..(83)
<223> OTHER INFORMATION: Xaa is Ser or absent
<220> FEATURE:
<221> NAME/KEY: VARIANT
<222> LOCATION: (84)..(84)
<223> OTHER INFORMATION: Xaa is Thr or absent.
<220> FEATURE:
<221> NAME/KEY: VARIANT
<222> LOCATION: (84)..(97)
<223> OTHER INFORMATION: If Xaa at position 84 is any of the amino acids
      listed (as in, the position is not absent), then the Xaa's from
      positions 85-97 are absent; if Xaa at position 84 is absent, then
      the Xaa's from positions 85-97 are not absent.
<220> FEATURE:
<221> NAME/KEY: VARIANT
<222> LOCATION: (85)..(124)
<223> OTHER INFORMATION: If Xaas from position 85-97 are present, then
      all Xaas from position 98-124 are absent.
<220> FEATURE:
<221> NAME/KEY: VARIANT
<222> LOCATION: (85)..(85)
<223> OTHER INFORMATION: Xaa is Lys or absent
<220> FEATURE:
<221> NAME/KEY: VARIANT
<222> LOCATION: (86)..(86)
<223> OTHER INFORMATION: Xaa is Asn or absent
<220> FEATURE:
<221> NAME/KEY: VARIANT
<222> LOCATION: (87)..(87)
<223> OTHER INFORMATION: Xaa is Gly or absent
<220> FEATURE:
<221> NAME/KEY: VARIANT
<222> LOCATION: (88)..(88)
<223> OTHER INFORMATION: Xaa is Gly or absent
<220> FEATURE:
<221> NAME/KEY: VARIANT
<222> LOCATION: (89)..(89)
<223> OTHER INFORMATION: Xaa is Pro or absent
<220> FEATURE:
<221> NAME/KEY: VARIANT
<222> LOCATION: (90)..(90)
<223> OTHER INFORMATION: Xaa is Ser or absent
<220> FEATURE:
<221> NAME/KEY: VARIANT
<222> LOCATION: (91)..(91)
<223> OTHER INFORMATION: Xaa is Ser or absent
<220> FEATURE:
<221> NAME/KEY: VARIANT
<222> LOCATION: (92)..(92)
<223> OTHER INFORMATION: Xaa is Gly or absent
<220> FEATURE:
<221> NAME/KEY: VARIANT
<222> LOCATION: (93)..(93)
<223> OTHER INFORMATION: Xaa is Ala or absent
<220> FEATURE:
<221> NAME/KEY: VARIANT
<222> LOCATION: (94)..(94)
<223> OTHER INFORMATION: Xaa is Pro or absent
<220> FEATURE:
<221> NAME/KEY: VARIANT
```

```
<222> LOCATION: (95)..(95)
<223> OTHER INFORMATION: Xaa is Pro or absent
<220> FEATURE:
<221> NAME/KEY: VARIANT
<222> LOCATION: (96)..(96)
<223> OTHER INFORMATION: Xaa is Pro or absent
<220> FEATURE:
<221> NAME/KEY: VARIANT
<222> LOCATION: (97)..(97)
<223> OTHER INFORMATION: Xaa is Ser or absent
<220> FEATURE:
<221> NAME/KEY: VARIANT
<222> LOCATION: (98)..(98)
<223> OTHER INFORMATION: Xaa is Asp, Asn, or absent.
<220> FEATURE:
<221> NAME/KEY: VARIANT
<222> LOCATION: (98)..(111)
<223> OTHER INFORMATION: If Xaa at position 98 is any of the amino acids
      listed (as in, the position is not absent), then the Xaa's from
      positions 99-111 are absent; if Xaa at position 98 is absent, then
      the Xaa's from positions 99-111 are not absent.
<220> FEATURE:
<221> NAME/KEY: VARIANT
<222> LOCATION: (99)..(124)
<223> OTHER INFORMATION: If Xaas from position 99-111 are present, then
      all Xaas from position 112-124 are absent.
<220> FEATURE:
<221> NAME/KEY: VARIANT
<222> LOCATION: (99)..(99)
<223> OTHER INFORMATION: Xaa is Lys or absent
<220> FEATURE:
<221> NAME/KEY: VARIANT
<222> LOCATION: (100)..(100)
<223> OTHER INFORMATION: Xaa is Asn or absent
<220> FEATURE:
<221> NAME/KEY: VARIANT
<222> LOCATION: (101)..(101)
<223> OTHER INFORMATION: Xaa is Gly or absent
<220> FEATURE:
<221> NAME/KEY: VARIANT
<222> LOCATION: (102)..(102)
<223> OTHER INFORMATION: Xaa is Gly or absent
<220> FEATURE:
<221> NAME/KEY: VARIANT
<222> LOCATION: (103)..(103)
<223> OTHER INFORMATION: Xaa is Pro or absent
<220> FEATURE:
<221> NAME/KEY: VARIANT
<222> LOCATION: (104)..(104)
<223> OTHER INFORMATION: Xaa is Ser or absent
<220> FEATURE:
<221> NAME/KEY: VARIANT
<222> LOCATION: (105)..(105)
<223> OTHER INFORMATION: Xaa is Ser or absent
<220> FEATURE:
<221> NAME/KEY: VARIANT
<222> LOCATION: (106)..(106)
<223> OTHER INFORMATION: Xaa is Gly or absent
<220> FEATURE:
<221> NAME/KEY: VARIANT
<222> LOCATION: (107)..(107)
<223> OTHER INFORMATION: Xaa is Ala or absent
<220> FEATURE:
<221> NAME/KEY: VARIANT
<222> LOCATION: (108)..(108)
<223> OTHER INFORMATION: Xaa is Pro or absent
<220> FEATURE:
<221> NAME/KEY: VARIANT
<222> LOCATION: (109)..(109)
<223> OTHER INFORMATION: Xaa is Pro or absent
<220> FEATURE:
<221> NAME/KEY: VARIANT
<222> LOCATION: (110)..(110)
<223> OTHER INFORMATION: Xaa is Pro or absent
<220> FEATURE:
<221> NAME/KEY: VARIANT
<222> LOCATION: (111)..(111)
<223> OTHER INFORMATION: Xaa is Ser or absent
<220> FEATURE:
```

```
<221> NAME/KEY: VARIANT
<222> LOCATION: (112)..(112)
<223> OTHER INFORMATION: Xaa is Lys or absent
<220> FEATURE:
<221> NAME/KEY: VARIANT
<222> LOCATION: (112)..(124)
<223> OTHER INFORMATION: If Xaa at position 112 is absent, then Xaa's
      from positions 113-124 are also absent; if Xaa at position 112 is
      not absent, then Xaa's from positions 113-124 are also not absent.
<220> FEATURE:
<221> NAME/KEY: VARIANT
<222> LOCATION: (113)..(113)
<223> OTHER INFORMATION: Xaa is Asn or absent
<220> FEATURE:
<221> NAME/KEY: VARIANT
<222> LOCATION: (114)..(114)
<223> OTHER INFORMATION: Xaa is Gly or absent
<220> FEATURE:
<221> NAME/KEY: VARIANT
<222> LOCATION: (115)..(115)
<223> OTHER INFORMATION: Xaa is Gly or absent
<220> FEATURE:
<221> NAME/KEY: VARIANT
<222> LOCATION: (116)..(116)
<223> OTHER INFORMATION: Xaa is Pro or absent
<220> FEATURE:
<221> NAME/KEY: VARIANT
<222> LOCATION: (117)..(117)
<223> OTHER INFORMATION: Xaa is Ser or absent
<220> FEATURE:
<221> NAME/KEY: VARIANT
<222> LOCATION: (118)..(118)
<223> OTHER INFORMATION: Xaa is Ser or absent
<220> FEATURE:
<221> NAME/KEY: VARIANT
<222> LOCATION: (119)..(119)
<223> OTHER INFORMATION: Xaa is Gly or absent
<220> FEATURE:
<221> NAME/KEY: VARIANT
<222> LOCATION: (120)..(120)
<223> OTHER INFORMATION: Xaa is Ala or absent
<220> FEATURE:
<221> NAME/KEY: VARIANT
<222> LOCATION: (121)..(121)
<223> OTHER INFORMATION: Xaa is Pro or absent
<220> FEATURE:
<221> NAME/KEY: VARIANT
<222> LOCATION: (122)..(122)
<223> OTHER INFORMATION: Xaa is Pro or absent
<220> FEATURE:
<221> NAME/KEY: VARIANT
<222> LOCATION: (123)..(123)
<223> OTHER INFORMATION: Xaa is Pro or absent
<220> FEATURE:
<221> NAME/KEY: VARIANT
<222> LOCATION: (124)..(124)
<223> OTHER INFORMATION: Xaa is Ser or absent

<400> SEQUENCE: 10

His Xaa Gly Xaa Phe Xaa Ser Glu Leu Ala Xaa Xaa Xaa Xaa Xaa
1               5                   10                  15

Xaa Ala Xaa Xaa Xaa Phe Ile Xaa Trp Leu Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
```

-continued

```
                100              105              110
Xaa Xaa Xaa Xaa Xaa Xaa Xaa Xaa Xaa Xaa Xaa
        115              120

<210> SEQ ID NO 11
<211> LENGTH: 33
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (2)..(2)
<223> OTHER INFORMATION: Aib

<400> SEQUENCE: 11

His Ala Asp Gly Ser Phe Ser Asp Glu Met Asn Thr Ile Leu Asp Asn
1               5                   10                  15

Gln Ala Ala Arg Asp Phe Ile Asn Trp Leu Ile Gln Thr Lys Ile Thr
            20                  25                  30

Asp

<210> SEQ ID NO 12
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 12

His Gly Asp Gly Ser Phe Ser Asp Glu Met Asn Thr Ile Leu Asp Asn
1               5                   10                  15

Lys Ala Ala Arg Asp Phe Ile Asn Trp Leu Ile Gln Thr Lys Ile Thr
            20                  25                  30

Asp

<210> SEQ ID NO 13
<211> LENGTH: 30
<212> TYPE: PRT
<213> ORGANISM: Artificial sequence
<220> FEATURE:
<223> OTHER INFORMATION: Synthetic sequence: GLP-2 analogue

<400> SEQUENCE: 13

His Gly Asp Gly Ser Phe Ser Asp Glu Met Asn Thr Ile Leu Asp Gly
1               5                   10                  15

Gln Ala Ala Arg Asp Phe Ile Asn Trp Leu Ile Gln Thr Lys
            20                  25                  30

<210> SEQ ID NO 14
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 14

His Gly Asp Gly Ser Phe Ser Ser Glu Met Asn Thr Ile Leu Asp Ser
1               5                   10                  15

Gln Ala Ala Arg Asp Phe Ile Asn Trp Leu Ile Gln Thr Lys Ile Thr
            20                  25                  30

Asp
```

<210> SEQ ID NO 15
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 15

His Gly Glu Gly Thr Phe Thr Ser Asp Leu Ser Lys Gln Met Glu Gly
1               5                   10                  15

Gln Ala Val Arg Asp Phe Ile Glu Trp Leu Ile Gln Thr Lys Ile Thr
            20                  25                  30

Asp

<210> SEQ ID NO 16
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 16

His Gly Glu Gly Thr Phe Thr Ser Asp Leu Ser Lys Gln Met Glu Ser
1               5                   10                  15

Lys Ala Ala Arg Asp Phe Ile Glu Trp Leu Ile Gln Thr Lys Ile Thr
            20                  25                  30

Asp

<210> SEQ ID NO 17
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 17

His Gly Asp Gly Ser Phe Ser Ser Glu Leu Ala Thr Ile Leu Asp Gly
1               5                   10                  15

Lys Ala Ala Arg Asp Phe Ile Asn Trp Leu Ile Gln Thr Lys Ile Thr
            20                  25                  30

Asp

<210> SEQ ID NO 18
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 18

His Gly Glu Gly Thr Phe Thr Ser Asp Leu Ser Thr Ile Leu Glu Asn
1               5                   10                  15

Lys Ala Ala Arg Asp Phe Ile Glu Trp Leu Ile Gln Thr Lys Ile Thr
            20                  25                  30

Asp

<210> SEQ ID NO 19
<211> LENGTH: 33
<212> TYPE: PRT
<213> ORGANISM: Artificial sequence
<220> FEATURE:
<223> OTHER INFORMATION: Synthetic sequence: GLP-2 analogue

```
<400> SEQUENCE: 19

His Gly Glu Gly Ser Phe Ser Ser Asp Leu Ser Thr Ile Leu Glu Asn
1               5                   10                  15

Lys Ala Ala Arg Asp Phe Ile Glu Trp Leu Ile Gln Thr Lys Ile Thr
            20                  25                  30

Asp

<210> SEQ ID NO 20
<211> LENGTH: 30
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (2)..(2)
<223> OTHER INFORMATION: Aib

<400> SEQUENCE: 20

His Ala Asp Gly Ser Phe Ser Asp Glu Leu Asn Thr Ile Leu Asp Gly
1               5                   10                  15

Lys Ala Ala Arg Asp Phe Ile Asn Trp Leu Ile Gln Thr Lys
            20                  25                  30

<210> SEQ ID NO 21
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 21

His Gly Asp Gly Ser Phe Ser Ser Glu Leu Ala Thr Ile Leu Asp Gly
1               5                   10                  15

Gln Ala Ala Arg Asp Phe Ile Ala Trp Leu Ile Gln Thr Lys Ile Thr
            20                  25                  30

Asp

<210> SEQ ID NO 22
<211> LENGTH: 30
<212> TYPE: PRT
<213> ORGANISM: Artificial sequence
<220> FEATURE:
<223> OTHER INFORMATION: Synthetic sequence: GLP-2 analogue

<400> SEQUENCE: 22

His Gly Asp Gly Ser Phe Ser Asp Glu Met Asn Thr Ile Leu Asp Gly
1               5                   10                  15

Gln Ala Ala Arg Asp Phe Ile Asn Trp Leu Ile Gln Thr Lys
            20                  25                  30

<210> SEQ ID NO 23
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 23

His Gly Glu Gly Ser Phe Ser Ser Asp Leu Ser Thr Ile Leu Glu Gly
1               5                   10                  15

Lys Ala Ala Arg Asp Phe Ile Glu Trp Leu Ile Gln Thr Lys Ile Thr
```

```
                20                  25                  30

Asp

<210> SEQ ID NO 24
<211> LENGTH: 110
<212> TYPE: PRT
<213> ORGANISM: Artificial sequence
<220> FEATURE:
<223> OTHER INFORMATION: Synthetic sequence: GLP-2 analogue: General
      Formula III of PCT/EP2013/059320
<220> FEATURE:
<221> NAME/KEY: VARIANT
<222> LOCATION: (3)..(3)
<223> OTHER INFORMATION: Xaa is Glu or Asp
<220> FEATURE:
<221> NAME/KEY: VARIANT
<222> LOCATION: (5)..(5)
<223> OTHER INFORMATION: Xaa is Ser or Thr
<220> FEATURE:
<221> NAME/KEY: VARIANT
<222> LOCATION: (7)..(7)
<223> OTHER INFORMATION: Xaa is Ser or Thr
<220> FEATURE:
<221> NAME/KEY: VARIANT
<222> LOCATION: (12)..(12)
<223> OTHER INFORMATION: Xaa is Thr, Ser or Lys
<220> FEATURE:
<221> NAME/KEY: VARIANT
<222> LOCATION: (13)..(13)
<223> OTHER INFORMATION: Xaa is Ile, Tyr, or Gln
<220> FEATURE:
<221> NAME/KEY: VARIANT
<222> LOCATION: (15)..(15)
<223> OTHER INFORMATION: Xaa is Asp or Glu
<220> FEATURE:
<221> NAME/KEY: VARIANT
<222> LOCATION: (17)..(17)
<223> OTHER INFORMATION: Xaa is Gln or Lys
<220> FEATURE:
<221> NAME/KEY: VARIANT
<222> LOCATION: (19)..(19)
<223> OTHER INFORMATION: Xaa is Ala or Val
<220> FEATURE:
<221> NAME/KEY: VARIANT
<222> LOCATION: (20)..(20)
<223> OTHER INFORMATION: Xaa is Arg, Lys or His
<220> FEATURE:
<221> NAME/KEY: VARIANT
<222> LOCATION: (21)..(21)
<223> OTHER INFORMATION: Xaa is Asp, Glu or Leu
<220> FEATURE:
<221> NAME/KEY: VARIANT
<222> LOCATION: (24)..(24)
<223> OTHER INFORMATION: Xaa is Asn, Ala, or Glu
<220> FEATURE:
<221> NAME/KEY: VARIANT
<222> LOCATION: (27)..(27)
<223> OTHER INFORMATION: Xaa is Ile, Leu, Glu or Lys
<220> FEATURE:
<221> NAME/KEY: VARIANT
<222> LOCATION: (28)..(28)
<223> OTHER INFORMATION: Xaa is Gln, Lys, Ser, Gly, or absent.
<220> FEATURE:
<221> NAME/KEY: VARIANT
<222> LOCATION: (28)..(39)
<223> OTHER INFORMATION: If Xaa at position 28 is any of the amino acids
      listed (as in, the position is not absent), then the Xaa's from
      positions 29-39 are absent; if Xaa at position 28 is absent, then
      the Xaa's from positions 29-39 are not absent.
<220> FEATURE:
<221> NAME/KEY: VARIANT
<222> LOCATION: (29)..(110)
<223> OTHER INFORMATION: If Xaas from position 29-39 are present, then
      all Xaas from position 40-110 are absent.
<220> FEATURE:
<221> NAME/KEY: VARIANT
<222> LOCATION: (29)..(29)
```

```
<223> OTHER INFORMATION: Xaa is Gly or absent
<220> FEATURE:
<221> NAME/KEY: VARIANT
<222> LOCATION: (30)..(30)
<223> OTHER INFORMATION: Xaa is Gly or absent
<220> FEATURE:
<221> NAME/KEY: VARIANT
<222> LOCATION: (31)..(31)
<223> OTHER INFORMATION: Xaa is Pro or absent
<220> FEATURE:
<221> NAME/KEY: VARIANT
<222> LOCATION: (32)..(32)
<223> OTHER INFORMATION: Xaa is Ser or absent
<220> FEATURE:
<221> NAME/KEY: VARIANT
<222> LOCATION: (33)..(33)
<223> OTHER INFORMATION: Xaa is Ser or absent
<220> FEATURE:
<221> NAME/KEY: VARIANT
<222> LOCATION: (34)..(34)
<223> OTHER INFORMATION: Xaa is Gly or absent
<220> FEATURE:
<221> NAME/KEY: VARIANT
<222> LOCATION: (35)..(35)
<223> OTHER INFORMATION: Xaa is Ala or absent
<220> FEATURE:
<221> NAME/KEY: VARIANT
<222> LOCATION: (36)..(36)
<223> OTHER INFORMATION: Xaa is Pro or absent
<220> FEATURE:
<221> NAME/KEY: VARIANT
<222> LOCATION: (37)..(37)
<223> OTHER INFORMATION: Xaa is Pro or absent
<220> FEATURE:
<221> NAME/KEY: VARIANT
<222> LOCATION: (38)..(38)
<223> OTHER INFORMATION: Xaa is Pro or absent
<220> FEATURE:
<221> NAME/KEY: VARIANT
<222> LOCATION: (39)..(39)
<223> OTHER INFORMATION: Xaa is Ser or absent
<220> FEATURE:
<221> NAME/KEY: VARIANT
<222> LOCATION: (40)..(40)
<223> OTHER INFORMATION: Xaa is Thr, Ala, or absent.
<220> FEATURE:
<221> NAME/KEY: VARIANT
<222> LOCATION: (40)..(51)
<223> OTHER INFORMATION: If Xaa at position 40 is any of the amino acids
      listed (as in, the position is not absent), then the Xaa's from
      positions 41-51 are absent; if Xaa at position 40 is absent, then
      the Xaa's from positions 41-51 are not absent.
<220> FEATURE:
<221> NAME/KEY: VARIANT
<222> LOCATION: (41)..(110)
<223> OTHER INFORMATION: If Xaas from position 41-51 are present, then
      all Xaas from position 52-110 are absent.
<220> FEATURE:
<221> NAME/KEY: VARIANT
<222> LOCATION: (41)..(41)
<223> OTHER INFORMATION: Xaa is Gly or absent
<220> FEATURE:
<221> NAME/KEY: VARIANT
<222> LOCATION: (42)..(42)
<223> OTHER INFORMATION: Xaa is Gly or absent
<220> FEATURE:
<221> NAME/KEY: VARIANT
<222> LOCATION: (43)..(43)
<223> OTHER INFORMATION: Xaa is Pro or absent
<220> FEATURE:
<221> NAME/KEY: VARIANT
<222> LOCATION: (44)..(44)
<223> OTHER INFORMATION: Xaa is Ser or absent
<220> FEATURE:
<221> NAME/KEY: VARIANT
<222> LOCATION: (45)..(45)
<223> OTHER INFORMATION: Xaa is Ser or absent
<220> FEATURE:
<221> NAME/KEY: VARIANT
```

```
<222> LOCATION: (46)..(46)
<223> OTHER INFORMATION: Xaa is Gly or absent
<220> FEATURE:
<221> NAME/KEY: VARIANT
<222> LOCATION: (47)..(47)
<223> OTHER INFORMATION: Xaa is Ala or absent
<220> FEATURE:
<221> NAME/KEY: VARIANT
<222> LOCATION: (48)..(48)
<223> OTHER INFORMATION: Xaa is Pro or absent
<220> FEATURE:
<221> NAME/KEY: VARIANT
<222> LOCATION: (49)..(49)
<223> OTHER INFORMATION: Xaa is Pro or absent
<220> FEATURE:
<221> NAME/KEY: VARIANT
<222> LOCATION: (50)..(50)
<223> OTHER INFORMATION: Xaa is Pro or absent
<220> FEATURE:
<221> NAME/KEY: VARIANT
<222> LOCATION: (51)..(51)
<223> OTHER INFORMATION: Xaa is Ser or absent
<220> FEATURE:
<221> NAME/KEY: VARIANT
<222> LOCATION: (52)..(52)
<223> OTHER INFORMATION: Xaa is Lys or absent.
<220> FEATURE:
<221> NAME/KEY: VARIANT
<222> LOCATION: (52)..(63)
<223> OTHER INFORMATION: If Xaa at position 52 is any of the amino acids
      listed (as in, the position is not absent), then the Xaa's from
      positions 53-63 are absent; if Xaa at position 52 is absent, then
      the Xaa's from positions 53-63 are not absent.
<220> FEATURE:
<221> NAME/KEY: VARIANT
<222> LOCATION: (53)..(110)
<223> OTHER INFORMATION: If Xaas from position 53-63 are present, then
      all Xaas from position 64-110 are absent.
<220> FEATURE:
<221> NAME/KEY: VARIANT
<222> LOCATION: (53)..(53)
<223> OTHER INFORMATION: Xaa is Gly or absent
<220> FEATURE:
<221> NAME/KEY: VARIANT
<222> LOCATION: (54)..(54)
<223> OTHER INFORMATION: Xaa is Gly or absent
<220> FEATURE:
<221> NAME/KEY: VARIANT
<222> LOCATION: (55)..(55)
<223> OTHER INFORMATION: Xaa is Pro or absent
<220> FEATURE:
<221> NAME/KEY: VARIANT
<222> LOCATION: (56)..(56)
<223> OTHER INFORMATION: Xaa is Ser or absent
<220> FEATURE:
<221> NAME/KEY: VARIANT
<222> LOCATION: (57)..(57)
<223> OTHER INFORMATION: Xaa is Ser or absent
<220> FEATURE:
<221> NAME/KEY: VARIANT
<222> LOCATION: (58)..(58)
<223> OTHER INFORMATION: Xaa is Gly or absent
<220> FEATURE:
<221> NAME/KEY: VARIANT
<222> LOCATION: (59)..(59)
<223> OTHER INFORMATION: Xaa is Ala or absent
<220> FEATURE:
<221> NAME/KEY: VARIANT
<222> LOCATION: (60)..(60)
<223> OTHER INFORMATION: Xaa is Pro or absent
<220> FEATURE:
<221> NAME/KEY: VARIANT
<222> LOCATION: (61)..(61)
<223> OTHER INFORMATION: Xaa is Pro or absent
<220> FEATURE:
<221> NAME/KEY: VARIANT
<222> LOCATION: (62)..(62)
<223> OTHER INFORMATION: Xaa is Pro or absent
<220> FEATURE:
```

```
<221> NAME/KEY: VARIANT
<222> LOCATION: (63)..(63)
<223> OTHER INFORMATION: Xaa is Ser or absent
<220> FEATURE:
<221> NAME/KEY: VARIANT
<222> LOCATION: (64)..(64)
<223> OTHER INFORMATION: Xaa is Ile, Pro, or absent.
<220> FEATURE:
<221> NAME/KEY: VARIANT
<222> LOCATION: (64)..(75)
<223> OTHER INFORMATION: If Xaa at position 64 is any of the amino acids
      listed (as in, the position is not absent), then the Xaa's from
      positions 65-75 are absent; if Xaa at position 64 is absent, then
      the Xaa's from positions 65-75 are not absent.
<220> FEATURE:
<221> NAME/KEY: VARIANT
<222> LOCATION: (65)..(110)
<223> OTHER INFORMATION: If Xaas from position 65-75 are present, then
      all Xaas from position 76-110 are absent.
<220> FEATURE:
<221> NAME/KEY: VARIANT
<222> LOCATION: (65)..(65)
<223> OTHER INFORMATION: Xaa is Gly or absent
<220> FEATURE:
<221> NAME/KEY: VARIANT
<222> LOCATION: (66)..(66)
<223> OTHER INFORMATION: Xaa is Gly or absent
<220> FEATURE:
<221> NAME/KEY: VARIANT
<222> LOCATION: (67)..(67)
<223> OTHER INFORMATION: Xaa is Pro or absent
<220> FEATURE:
<221> NAME/KEY: VARIANT
<222> LOCATION: (68)..(68)
<223> OTHER INFORMATION: Xaa is Ser or absent
<220> FEATURE:
<221> NAME/KEY: VARIANT
<222> LOCATION: (69)..(69)
<223> OTHER INFORMATION: Xaa is Ser or absent
<220> FEATURE:
<221> NAME/KEY: VARIANT
<222> LOCATION: (70)..(70)
<223> OTHER INFORMATION: Xaa is Gly or absent
<220> FEATURE:
<221> NAME/KEY: VARIANT
<222> LOCATION: (71)..(71)
<223> OTHER INFORMATION: Xaa is Ala or absent
<220> FEATURE:
<221> NAME/KEY: VARIANT
<222> LOCATION: (72)..(72)
<223> OTHER INFORMATION: Xaa is Pro or absent
<220> FEATURE:
<221> NAME/KEY: VARIANT
<222> LOCATION: (73)..(73)
<223> OTHER INFORMATION: Xaa is Pro or absent
<220> FEATURE:
<221> NAME/KEY: VARIANT
<222> LOCATION: (74)..(74)
<223> OTHER INFORMATION: Xaa is Pro or absent
<220> FEATURE:
<221> NAME/KEY: VARIANT
<222> LOCATION: (75)..(75)
<223> OTHER INFORMATION: Xaa is Ser or absent
<220> FEATURE:
<221> NAME/KEY: VARIANT
<222> LOCATION: (76)..(76)
<223> OTHER INFORMATION: Xaa is Thr or absent.
<220> FEATURE:
<221> NAME/KEY: VARIANT
<222> LOCATION: (76)..(87)
<223> OTHER INFORMATION: If Xaa at position 76 is any of the amino acids
      listed (as in, the position is not absent), then the Xaa's from
      positions 77-87 are absent; if Xaa at position 76 is absent, then
      the Xaa's from positions 77-87 are not absent.
<220> FEATURE:
<221> NAME/KEY: VARIANT
<222> LOCATION: (77)..(110)
<223> OTHER INFORMATION: If Xaas from position 77-87 are present, then
      all Xaas from position 88-110 are absent.
```

```
<220> FEATURE:
<221> NAME/KEY: VARIANT
<222> LOCATION: (77)..(77)
<223> OTHER INFORMATION: Xaa is Gly or absent
<220> FEATURE:
<221> NAME/KEY: VARIANT
<222> LOCATION: (78)..(78)
<223> OTHER INFORMATION: Xaa is Gly or absent
<220> FEATURE:
<221> NAME/KEY: VARIANT
<222> LOCATION: (79)..(79)
<223> OTHER INFORMATION: Xaa is Pro or absent
<220> FEATURE:
<221> NAME/KEY: VARIANT
<222> LOCATION: (80)..(80)
<223> OTHER INFORMATION: Xaa is Ser or absent
<220> FEATURE:
<221> NAME/KEY: VARIANT
<222> LOCATION: (81)..(81)
<223> OTHER INFORMATION: Xaa is Ser or absent
<220> FEATURE:
<221> NAME/KEY: VARIANT
<222> LOCATION: (82)..(82)
<223> OTHER INFORMATION: Xaa is Gly or absent
<220> FEATURE:
<221> NAME/KEY: VARIANT
<222> LOCATION: (83)..(83)
<223> OTHER INFORMATION: Xaa is Ala or absent
<220> FEATURE:
<221> NAME/KEY: VARIANT
<222> LOCATION: (84)..(84)
<223> OTHER INFORMATION: Xaa is Pro or absent
<220> FEATURE:
<221> NAME/KEY: VARIANT
<222> LOCATION: (85)..(85)
<223> OTHER INFORMATION: Xaa is Pro or absent
<220> FEATURE:
<221> NAME/KEY: VARIANT
<222> LOCATION: (86)..(86)
<223> OTHER INFORMATION: Xaa is Pro or absent
<220> FEATURE:
<221> NAME/KEY: VARIANT
<222> LOCATION: (87)..(87)
<223> OTHER INFORMATION: Xaa is Ser or absent
<220> FEATURE:
<221> NAME/KEY: VARIANT
<222> LOCATION: (88)..(88)
<223> OTHER INFORMATION: Xaa is Asp, Asn, or absent.
<220> FEATURE:
<221> NAME/KEY: VARIANT
<222> LOCATION: (88)..(99)
<223> OTHER INFORMATION: If Xaa at position 88 is any of the amino acids
      listed (as in, the position is not absent), then the Xaa's from
      positions 89-99 are absent; if Xaa at position 88 is absent, then
      the Xaa's from positions 89-99 are not absent.
<220> FEATURE:
<221> NAME/KEY: VARIANT
<222> LOCATION: (89)..(110)
<223> OTHER INFORMATION: If Xaas from position 89-99 are present, then
      all Xaas from position 100-110 are absent.
<220> FEATURE:
<221> NAME/KEY: VARIANT
<222> LOCATION: (89)..(89)
<223> OTHER INFORMATION: Xaa is Gly or absent
<220> FEATURE:
<221> NAME/KEY: VARIANT
<222> LOCATION: (90)..(90)
<223> OTHER INFORMATION: Xaa is Gly or absent
<220> FEATURE:
<221> NAME/KEY: VARIANT
<222> LOCATION: (91)..(91)
<223> OTHER INFORMATION: Xaa is Pro or absent
<220> FEATURE:
<221> NAME/KEY: VARIANT
<222> LOCATION: (92)..(92)
<223> OTHER INFORMATION: Xaa is Ser or absent
<220> FEATURE:
<221> NAME/KEY: VARIANT
<222> LOCATION: (93)..(93)
```

```
<223> OTHER INFORMATION: Xaa is Ser or absent
<220> FEATURE:
<221> NAME/KEY: VARIANT
<222> LOCATION: (94)..(94)
<223> OTHER INFORMATION: Xaa is Gly or absent
<220> FEATURE:
<221> NAME/KEY: VARIANT
<222> LOCATION: (95)..(95)
<223> OTHER INFORMATION: Xaa is Ala or absent
<220> FEATURE:
<221> NAME/KEY: VARIANT
<222> LOCATION: (96)..(96)
<223> OTHER INFORMATION: Xaa is Pro or absent
<220> FEATURE:
<221> NAME/KEY: VARIANT
<222> LOCATION: (97)..(97)
<223> OTHER INFORMATION: Xaa is Pro or absent
<220> FEATURE:
<221> NAME/KEY: VARIANT
<222> LOCATION: (98)..(98)
<223> OTHER INFORMATION: Xaa is Pro or absent
<220> FEATURE:
<221> NAME/KEY: VARIANT
<222> LOCATION: (99)..(99)
<223> OTHER INFORMATION: Xaa is Ser or absent
<220> FEATURE:
<221> NAME/KEY: VARIANT
<222> LOCATION: (100)..(100)
<223> OTHER INFORMATION: Xaa is Gly or absent
<220> FEATURE:
<221> NAME/KEY: VARIANT
<222> LOCATION: (100)..(110)
<223> OTHER INFORMATION: If Xaa at position 100 is absent, then Xaa's
      from positions 101-110 are also absent; if Xaa at position 100 is
      not absent, then Xaa's from positions 101-110 are also not absent.
<220> FEATURE:
<221> NAME/KEY: VARIANT
<222> LOCATION: (101)..(101)
<223> OTHER INFORMATION: Xaa is Gly or absent
<220> FEATURE:
<221> NAME/KEY: VARIANT
<222> LOCATION: (102)..(102)
<223> OTHER INFORMATION: Xaa is Pro or absent
<220> FEATURE:
<221> NAME/KEY: VARIANT
<222> LOCATION: (103)..(103)
<223> OTHER INFORMATION: Xaa is Ser or absent
<220> FEATURE:
<221> NAME/KEY: VARIANT
<222> LOCATION: (104)..(104)
<223> OTHER INFORMATION: Xaa is Ser or absent
<220> FEATURE:
<221> NAME/KEY: VARIANT
<222> LOCATION: (105)..(105)
<223> OTHER INFORMATION: Xaa is Gly or absent
<220> FEATURE:
<221> NAME/KEY: VARIANT
<222> LOCATION: (106)..(106)
<223> OTHER INFORMATION: Xaa is Ala or absent
<220> FEATURE:
<221> NAME/KEY: VARIANT
<222> LOCATION: (107)..(107)
<223> OTHER INFORMATION: Xaa is Pro or absent
<220> FEATURE:
<221> NAME/KEY: VARIANT
<222> LOCATION: (108)..(108)
<223> OTHER INFORMATION: Xaa is Pro or absent
<220> FEATURE:
<221> NAME/KEY: VARIANT
<222> LOCATION: (109)..(109)
<223> OTHER INFORMATION: Xaa is Pro or absent
<220> FEATURE:
<221> NAME/KEY: VARIANT
<222> LOCATION: (110)..(110)
<223> OTHER INFORMATION: Xaa is Ser or absent

<400> SEQUENCE: 24

His Gly Xaa Gly Xaa Phe Xaa Ser Glu Leu Ala Xaa Xaa Leu Xaa Gly
```

```
                1               5                      10                      15
Xaa Ala Xaa Xaa Xaa Phe Ile Xaa Trp Leu Xaa Xaa Xaa Xaa Xaa Xaa
                        20                      25                      30

Xaa Xaa Xaa Xaa Xaa Xaa Xaa Xaa Xaa Xaa Xaa Xaa Xaa Xaa Xaa
        35                      40                      45

Xaa Xaa Xaa Xaa Xaa Xaa Xaa Xaa Xaa Xaa Xaa Xaa Xaa Xaa Xaa
50                      55                      60

Xaa Xaa Xaa Xaa Xaa Xaa Xaa Xaa Xaa Xaa Xaa Xaa Xaa Xaa Xaa Xaa
65                      70                      75                      80

Xaa Xaa Xaa Xaa Xaa Xaa Xaa Xaa Xaa Xaa Xaa Xaa Xaa Xaa Xaa
                85                      90                      95

Xaa Xaa Xaa Xaa Xaa Xaa Xaa Xaa Xaa Xaa Xaa Xaa Xaa
        100                     105                     110
```

```
<210> SEQ ID NO 25
<211> LENGTH: 124
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (3)..(3)
<223> OTHER INFORMATION: Xaa is Glu or Asp
<220> FEATURE:
<221> NAME/KEY: VARIANT
<222> LOCATION: (5)..(5)
<223> OTHER INFORMATION: Xaa is Ser or Thr
<220> FEATURE:
<221> NAME/KEY: VARIANT
<222> LOCATION: (7)..(7)
<223> OTHER INFORMATION: Xaa is Ser or Thr
<220> FEATURE:
<221> NAME/KEY: VARIANT
<222> LOCATION: (12)..(12)
<223> OTHER INFORMATION: Xaa is Thr, Ser or Lys
<220> FEATURE:
<221> NAME/KEY: VARIANT
<222> LOCATION: (13)..(13)
<223> OTHER INFORMATION: Xaa is Ile, Tyr, or Gln
<220> FEATURE:
<221> NAME/KEY: VARIANT
<222> LOCATION: (15)..(15)
<223> OTHER INFORMATION: Xaa is Asp or Glu
<220> FEATURE:
<221> NAME/KEY: VARIANT
<222> LOCATION: (17)..(17)
<223> OTHER INFORMATION: Xaa is Gln or Lys
<220> FEATURE:
<221> NAME/KEY: VARIANT
<222> LOCATION: (19)..(19)
<223> OTHER INFORMATION: Xaa is Ala or Val
<220> FEATURE:
<221> NAME/KEY: VARIANT
<222> LOCATION: (20)..(20)
<223> OTHER INFORMATION: Xaa is Arg, Lys or His
<220> FEATURE:
<221> NAME/KEY: VARIANT
<222> LOCATION: (21)..(21)
<223> OTHER INFORMATION: Xaa is Asp, Glu or Leu
<220> FEATURE:
<221> NAME/KEY: VARIANT
<222> LOCATION: (24)..(24)
<223> OTHER INFORMATION: Xaa is Asn, Ala, or Glu
<220> FEATURE:
<221> NAME/KEY: VARIANT
<222> LOCATION: (27)..(27)
<223> OTHER INFORMATION: Xaa is Ile, Leu, Glu or Lys
<220> FEATURE:
<221> NAME/KEY: VARIANT
<222> LOCATION: (28)..(28)
<223> OTHER INFORMATION: Xaa is Gln, Lys, Ser, Gly, or absent.
```

```
<220> FEATURE:
<221> NAME/KEY: VARIANT
<222> LOCATION: (28)..(41)
<223> OTHER INFORMATION: If Xaa at position 28 is any of the amino acids
      listed (as in, the position is not absent), then the Xaa's from
      positions 29-41 are absent; if Xaa at position 28 is absent, then
      the Xaa's from positions 29-41 are not absent.
<220> FEATURE:
<221> NAME/KEY: VARIANT
<222> LOCATION: (29)..(124)
<223> OTHER INFORMATION: If Xaas from position 29-41 are present, then
      all Xaas from position 42-124 are absent.
<220> FEATURE:
<221> NAME/KEY: VARIANT
<222> LOCATION: (29)..(29)
<223> OTHER INFORMATION: Xaa is Lys or absent
<220> FEATURE:
<221> NAME/KEY: VARIANT
<222> LOCATION: (30)..(30)
<223> OTHER INFORMATION: Xaa is Asn or absent
<220> FEATURE:
<221> NAME/KEY: VARIANT
<222> LOCATION: (31)..(31)
<223> OTHER INFORMATION: Xaa is Gly or absent
<220> FEATURE:
<221> NAME/KEY: VARIANT
<222> LOCATION: (32)..(32)
<223> OTHER INFORMATION: Xaa is Gly or absent
<220> FEATURE:
<221> NAME/KEY: VARIANT
<222> LOCATION: (33)..(33)
<223> OTHER INFORMATION: Xaa is Pro or absent
<220> FEATURE:
<221> NAME/KEY: VARIANT
<222> LOCATION: (34)..(34)
<223> OTHER INFORMATION: Xaa is Ser or absent
<220> FEATURE:
<221> NAME/KEY: VARIANT
<222> LOCATION: (35)..(35)
<223> OTHER INFORMATION: Xaa is Ser or absent
<220> FEATURE:
<221> NAME/KEY: VARIANT
<222> LOCATION: (36)..(36)
<223> OTHER INFORMATION: Xaa is Gly or absent
<220> FEATURE:
<221> NAME/KEY: VARIANT
<222> LOCATION: (37)..(37)
<223> OTHER INFORMATION: Xaa is Ala or absent
<220> FEATURE:
<221> NAME/KEY: VARIANT
<222> LOCATION: (38)..(38)
<223> OTHER INFORMATION: Xaa is Pro or absent
<220> FEATURE:
<221> NAME/KEY: VARIANT
<222> LOCATION: (39)..(39)
<223> OTHER INFORMATION: Xaa is Pro or absent
<220> FEATURE:
<221> NAME/KEY: VARIANT
<222> LOCATION: (40)..(40)
<223> OTHER INFORMATION: Xaa is Pro or absent
<220> FEATURE:
<221> NAME/KEY: VARIANT
<222> LOCATION: (41)..(41)
<223> OTHER INFORMATION: Xaa is Ser or absent
<220> FEATURE:
<221> NAME/KEY: VARIANT
<222> LOCATION: (42)..(42)
<223> OTHER INFORMATION: Xaa is Thr, Ala, or absent.
<220> FEATURE:
<221> NAME/KEY: VARIANT
<222> LOCATION: (42)..(55)
<223> OTHER INFORMATION: If Xaa at position 42 is any of the amino acids
      listed (as in, the position is not absent), then the Xaa's from
      positions 43-55 are absent; if Xaa at position 42 is absent, then
      the Xaa's from positions 43-55 are not absent.
<220> FEATURE:
<221> NAME/KEY: VARIANT
<222> LOCATION: (43)..(124)
<223> OTHER INFORMATION: If Xaas from position 43-55 are present, then
```

```
      all Xaas from position 56-124 are absent.
<220> FEATURE:
<221> NAME/KEY: VARIANT
<222> LOCATION: (43)..(43)
<223> OTHER INFORMATION: Xaa is Lys or absent
<220> FEATURE:
<221> NAME/KEY: VARIANT
<222> LOCATION: (44)..(44)
<223> OTHER INFORMATION: Xaa is Asn or absent
<220> FEATURE:
<221> NAME/KEY: VARIANT
<222> LOCATION: (45)..(45)
<223> OTHER INFORMATION: Xaa is Gly or absent
<220> FEATURE:
<221> NAME/KEY: VARIANT
<222> LOCATION: (46)..(46)
<223> OTHER INFORMATION: Xaa is Gly or absent
<220> FEATURE:
<221> NAME/KEY: VARIANT
<222> LOCATION: (47)..(47)
<223> OTHER INFORMATION: Xaa is Pro or absent
<220> FEATURE:
<221> NAME/KEY: VARIANT
<222> LOCATION: (48)..(48)
<223> OTHER INFORMATION: Xaa is Ser or absent
<220> FEATURE:
<221> NAME/KEY: VARIANT
<222> LOCATION: (49)..(49)
<223> OTHER INFORMATION: Xaa is Ser or absent
<220> FEATURE:
<221> NAME/KEY: VARIANT
<222> LOCATION: (50)..(50)
<223> OTHER INFORMATION: Xaa is Gly or absent
<220> FEATURE:
<221> NAME/KEY: VARIANT
<222> LOCATION: (51)..(51)
<223> OTHER INFORMATION: Xaa is Ala or absent
<220> FEATURE:
<221> NAME/KEY: VARIANT
<222> LOCATION: (52)..(52)
<223> OTHER INFORMATION: Xaa is Pro or absent
<220> FEATURE:
<221> NAME/KEY: VARIANT
<222> LOCATION: (53)..(53)
<223> OTHER INFORMATION: Xaa is Pro or absent
<220> FEATURE:
<221> NAME/KEY: VARIANT
<222> LOCATION: (54)..(54)
<223> OTHER INFORMATION: Xaa is Pro or absent
<220> FEATURE:
<221> NAME/KEY: VARIANT
<222> LOCATION: (55)..(55)
<223> OTHER INFORMATION: Xaa is Ser or absent
<220> FEATURE:
<221> NAME/KEY: VARIANT
<222> LOCATION: (56)..(56)
<223> OTHER INFORMATION: Xaa is Lys or absent.
<220> FEATURE:
<221> NAME/KEY: VARIANT
<222> LOCATION: (56)..(69)
<223> OTHER INFORMATION: If Xaa at position 56 is any of the amino acids
      listed (as in, the position is not absent), then the Xaa's from
      positions 57-69 are absent; if Xaa at position 56 is absent, then
      the Xaa's from positions 57-69 are not absent.
<220> FEATURE:
<221> NAME/KEY: VARIANT
<222> LOCATION: (57)..(124)
<223> OTHER INFORMATION: If Xaas from position 57-69 are present, then
      all Xaas from position 70-124 are absent.
<220> FEATURE:
<221> NAME/KEY: VARIANT
<222> LOCATION: (57)..(57)
<223> OTHER INFORMATION: Xaa is Lys or absent
<220> FEATURE:
<221> NAME/KEY: VARIANT
<222> LOCATION: (58)..(58)
<223> OTHER INFORMATION: Xaa is Asn or absent
<220> FEATURE:
<221> NAME/KEY: VARIANT
```

```
<222> LOCATION: (59)..(59)
<223> OTHER INFORMATION: Xaa is Gly or absent
<220> FEATURE:
<221> NAME/KEY: VARIANT
<222> LOCATION: (60)..(60)
<223> OTHER INFORMATION: Xaa is Gly or absent
<220> FEATURE:
<221> NAME/KEY: VARIANT
<222> LOCATION: (61)..(61)
<223> OTHER INFORMATION: Xaa is Pro or absent
<220> FEATURE:
<221> NAME/KEY: VARIANT
<222> LOCATION: (62)..(62)
<223> OTHER INFORMATION: Xaa is Ser or absent
<220> FEATURE:
<221> NAME/KEY: VARIANT
<222> LOCATION: (63)..(63)
<223> OTHER INFORMATION: Xaa is Ser or absent
<220> FEATURE:
<221> NAME/KEY: VARIANT
<222> LOCATION: (64)..(64)
<223> OTHER INFORMATION: Xaa is Gly or absent
<220> FEATURE:
<221> NAME/KEY: VARIANT
<222> LOCATION: (65)..(65)
<223> OTHER INFORMATION: Xaa is Ala or absent
<220> FEATURE:
<221> NAME/KEY: VARIANT
<222> LOCATION: (66)..(66)
<223> OTHER INFORMATION: Xaa is Pro or absent
<220> FEATURE:
<221> NAME/KEY: VARIANT
<222> LOCATION: (67)..(67)
<223> OTHER INFORMATION: Xaa is Pro or absent
<220> FEATURE:
<221> NAME/KEY: VARIANT
<222> LOCATION: (68)..(68)
<223> OTHER INFORMATION: Xaa is Pro or absent
<220> FEATURE:
<221> NAME/KEY: VARIANT
<222> LOCATION: (69)..(69)
<223> OTHER INFORMATION: Xaa is Ser or absent
<220> FEATURE:
<221> NAME/KEY: VARIANT
<222> LOCATION: (70)..(70)
<223> OTHER INFORMATION: Xaa is Ile, Pro, or absent.
<220> FEATURE:
<221> NAME/KEY: VARIANT
<222> LOCATION: (70)..(83)
<223> OTHER INFORMATION: If Xaa at position 70 is any of the amino acids
      listed (as in, the position is not absent), then the Xaa's from
      positions 71-83 are absent; if Xaa at position 70 is absent, then
      the Xaa's from positions 71-83 are not absent.
<220> FEATURE:
<221> NAME/KEY: VARIANT
<222> LOCATION: (71)..(124)
<223> OTHER INFORMATION: If Xaas from position 71-83 are present, then
      all Xaas from position 84-124 are absent.
<220> FEATURE:
<221> NAME/KEY: VARIANT
<222> LOCATION: (71)..(71)
<223> OTHER INFORMATION: Xaa is Lys or absent
<220> FEATURE:
<221> NAME/KEY: VARIANT
<222> LOCATION: (72)..(72)
<223> OTHER INFORMATION: Xaa is Asn or absent
<220> FEATURE:
<221> NAME/KEY: VARIANT
<222> LOCATION: (73)..(73)
<223> OTHER INFORMATION: Xaa is Gly or absent
<220> FEATURE:
<221> NAME/KEY: VARIANT
<222> LOCATION: (74)..(74)
<223> OTHER INFORMATION: Xaa is Gly or absent
<220> FEATURE:
<221> NAME/KEY: VARIANT
<222> LOCATION: (75)..(75)
<223> OTHER INFORMATION: Xaa is Pro or absent
<220> FEATURE:
```

```
<221> NAME/KEY: VARIANT
<222> LOCATION: (76)..(76)
<223> OTHER INFORMATION: Xaa is Ser or absent
<220> FEATURE:
<221> NAME/KEY: VARIANT
<222> LOCATION: (77)..(77)
<223> OTHER INFORMATION: Xaa is Ser or absent
<220> FEATURE:
<221> NAME/KEY: VARIANT
<222> LOCATION: (78)..(78)
<223> OTHER INFORMATION: Xaa is Gly or absent
<220> FEATURE:
<221> NAME/KEY: VARIANT
<222> LOCATION: (79)..(79)
<223> OTHER INFORMATION: Xaa is Ala or absent
<220> FEATURE:
<221> NAME/KEY: VARIANT
<222> LOCATION: (80)..(80)
<223> OTHER INFORMATION: Xaa is Pro or absent
<220> FEATURE:
<221> NAME/KEY: VARIANT
<222> LOCATION: (81)..(81)
<223> OTHER INFORMATION: Xaa is Pro or absent
<220> FEATURE:
<221> NAME/KEY: VARIANT
<222> LOCATION: (82)..(82)
<223> OTHER INFORMATION: Xaa is Pro or absent
<220> FEATURE:
<221> NAME/KEY: VARIANT
<222> LOCATION: (83)..(83)
<223> OTHER INFORMATION: Xaa is Ser or absent
<220> FEATURE:
<221> NAME/KEY: VARIANT
<222> LOCATION: (84)..(84)
<223> OTHER INFORMATION: Xaa is Thr or absent.
<220> FEATURE:
<221> NAME/KEY: VARIANT
<222> LOCATION: (84)..(97)
<223> OTHER INFORMATION: If Xaa at position 84 is any of the amino acids
      listed (as in, the position is not absent), then the Xaa's from
      positions 85-97 are absent; if Xaa at position 84 is absent, then
      the Xaa's from positions 85-97 are not absent.
<220> FEATURE:
<221> NAME/KEY: VARIANT
<222> LOCATION: (85)..(124)
<223> OTHER INFORMATION: If Xaas from position 85-97 are present, then
      all Xaas from position 98-124 are absent.
<220> FEATURE:
<221> NAME/KEY: VARIANT
<222> LOCATION: (85)..(85)
<223> OTHER INFORMATION: Xaa is Lys or absent
<220> FEATURE:
<221> NAME/KEY: VARIANT
<222> LOCATION: (86)..(86)
<223> OTHER INFORMATION: Xaa is Asn or absent
<220> FEATURE:
<221> NAME/KEY: VARIANT
<222> LOCATION: (87)..(87)
<223> OTHER INFORMATION: Xaa is Gly or absent
<220> FEATURE:
<221> NAME/KEY: VARIANT
<222> LOCATION: (88)..(88)
<223> OTHER INFORMATION: Xaa is Gly or absent
<220> FEATURE:
<221> NAME/KEY: VARIANT
<222> LOCATION: (89)..(89)
<223> OTHER INFORMATION: Xaa is Pro or absent
<220> FEATURE:
<221> NAME/KEY: VARIANT
<222> LOCATION: (90)..(90)
<223> OTHER INFORMATION: Xaa is Ser or absent
<220> FEATURE:
<221> NAME/KEY: VARIANT
<222> LOCATION: (91)..(91)
<223> OTHER INFORMATION: Xaa is Ser or absent
<220> FEATURE:
<221> NAME/KEY: VARIANT
<222> LOCATION: (92)..(92)
<223> OTHER INFORMATION: Xaa is Gly or absent
```

```
<220> FEATURE:
<221> NAME/KEY: VARIANT
<222> LOCATION: (93)..(93)
<223> OTHER INFORMATION: Xaa is Ala or absent
<220> FEATURE:
<221> NAME/KEY: VARIANT
<222> LOCATION: (94)..(94)
<223> OTHER INFORMATION: Xaa is Pro or absent
<220> FEATURE:
<221> NAME/KEY: VARIANT
<222> LOCATION: (95)..(95)
<223> OTHER INFORMATION: Xaa is Pro or absent
<220> FEATURE:
<221> NAME/KEY: VARIANT
<222> LOCATION: (96)..(96)
<223> OTHER INFORMATION: Xaa is Pro or absent
<220> FEATURE:
<221> NAME/KEY: VARIANT
<222> LOCATION: (97)..(97)
<223> OTHER INFORMATION: Xaa is Ser or absent
<220> FEATURE:
<221> NAME/KEY: VARIANT
<222> LOCATION: (98)..(98)
<223> OTHER INFORMATION: Xaa is Asp, Asn, or absent.
<220> FEATURE:
<221> NAME/KEY: VARIANT
<222> LOCATION: (98)..(111)
<223> OTHER INFORMATION: If Xaa at position 98 is any of the amino acids
      listed (as in, the position is not absent), then the Xaa's from
      positions 99-111 are absent; if Xaa at position 98 is absent, then
      the Xaa's from positions 99-111 are not absent.
<220> FEATURE:
<221> NAME/KEY: VARIANT
<222> LOCATION: (99)..(124)
<223> OTHER INFORMATION: If Xaas from position 99-111 are present, then
      all Xaas from position 112-124 are absent.
<220> FEATURE:
<221> NAME/KEY: VARIANT
<222> LOCATION: (99)..(99)
<223> OTHER INFORMATION: Xaa is Lys or absent
<220> FEATURE:
<221> NAME/KEY: VARIANT
<222> LOCATION: (100)..(100)
<223> OTHER INFORMATION: Xaa is Asn or absent
<220> FEATURE:
<221> NAME/KEY: VARIANT
<222> LOCATION: (101)..(101)
<223> OTHER INFORMATION: Xaa is Gly or absent
<220> FEATURE:
<221> NAME/KEY: VARIANT
<222> LOCATION: (102)..(102)
<223> OTHER INFORMATION: Xaa is Gly or absent
<220> FEATURE:
<221> NAME/KEY: VARIANT
<222> LOCATION: (103)..(103)
<223> OTHER INFORMATION: Xaa is Pro or absent
<220> FEATURE:
<221> NAME/KEY: VARIANT
<222> LOCATION: (104)..(104)
<223> OTHER INFORMATION: Xaa is Ser or absent
<220> FEATURE:
<221> NAME/KEY: VARIANT
<222> LOCATION: (105)..(105)
<223> OTHER INFORMATION: Xaa is Ser or absent
<220> FEATURE:
<221> NAME/KEY: VARIANT
<222> LOCATION: (106)..(106)
<223> OTHER INFORMATION: Xaa is Gly or absent
<220> FEATURE:
<221> NAME/KEY: VARIANT
<222> LOCATION: (107)..(107)
<223> OTHER INFORMATION: Xaa is Ala or absent
<220> FEATURE:
<221> NAME/KEY: VARIANT
<222> LOCATION: (108)..(108)
<223> OTHER INFORMATION: Xaa is Pro or absent
<220> FEATURE:
<221> NAME/KEY: VARIANT
<222> LOCATION: (109)..(109)
```

```
<223> OTHER INFORMATION: Xaa is Pro or absent
<220> FEATURE:
<221> NAME/KEY: VARIANT
<222> LOCATION: (110)..(110)
<223> OTHER INFORMATION: Xaa is Pro or absent
<220> FEATURE:
<221> NAME/KEY: VARIANT
<222> LOCATION: (111)..(111)
<223> OTHER INFORMATION: Xaa is Ser or absent
<220> FEATURE:
<221> NAME/KEY: VARIANT
<222> LOCATION: (112)..(112)
<223> OTHER INFORMATION: Xaa is Lys or absent
<220> FEATURE:
<221> NAME/KEY: VARIANT
<222> LOCATION: (112)..(124)
<223> OTHER INFORMATION: If Xaa at position 112 is absent, then Xaa's
      from positions 113-124 are also absent; if Xaa at position 112 is
      not absent, then Xaa's from positions 113-124 are also not absent.
<220> FEATURE:
<221> NAME/KEY: VARIANT
<222> LOCATION: (113)..(113)
<223> OTHER INFORMATION: Xaa is Asn or absent
<220> FEATURE:
<221> NAME/KEY: VARIANT
<222> LOCATION: (114)..(114)
<223> OTHER INFORMATION: Xaa is Gly or absent
<220> FEATURE:
<221> NAME/KEY: VARIANT
<222> LOCATION: (115)..(115)
<223> OTHER INFORMATION: Xaa is Gly or absent
<220> FEATURE:
<221> NAME/KEY: VARIANT
<222> LOCATION: (116)..(116)
<223> OTHER INFORMATION: Xaa is Pro or absent
<220> FEATURE:
<221> NAME/KEY: VARIANT
<222> LOCATION: (117)..(117)
<223> OTHER INFORMATION: Xaa is Ser or absent
<220> FEATURE:
<221> NAME/KEY: VARIANT
<222> LOCATION: (118)..(118)
<223> OTHER INFORMATION: Xaa is Ser or absent
<220> FEATURE:
<221> NAME/KEY: VARIANT
<222> LOCATION: (119)..(119)
<223> OTHER INFORMATION: Xaa is Gly or absent
<220> FEATURE:
<221> NAME/KEY: VARIANT
<222> LOCATION: (120)..(120)
<223> OTHER INFORMATION: Xaa is Ala or absent
<220> FEATURE:
<221> NAME/KEY: VARIANT
<222> LOCATION: (121)..(121)
<223> OTHER INFORMATION: Xaa is Pro or absent
<220> FEATURE:
<221> NAME/KEY: VARIANT
<222> LOCATION: (122)..(122)
<223> OTHER INFORMATION: Xaa is Pro or absent
<220> FEATURE:
<221> NAME/KEY: VARIANT
<222> LOCATION: (123)..(123)
<223> OTHER INFORMATION: Xaa is Pro or absent
<220> FEATURE:
<221> NAME/KEY: VARIANT
<222> LOCATION: (124)..(124)
<223> OTHER INFORMATION: Xaa is Ser or absent

<400> SEQUENCE: 25

His Gly Xaa Gly Xaa Phe Xaa Ser Glu Leu Ala Xaa Xaa Leu Xaa Gly
1               5                   10                  15

Xaa Ala Xaa Xaa Xaa Phe Ile Xaa Trp Leu Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45
```

```
Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa
            115                 120

<210> SEQ ID NO 26
<211> LENGTH: 11
<212> TYPE: PRT
<213> ORGANISM: Artificial sequence
<220> FEATURE:
<223> OTHER INFORMATION: Synthetic sequence

<400> SEQUENCE: 26

Gly Gly Pro Ser Ser Gly Ala Pro Pro Pro Ser
1               5                   10

<210> SEQ ID NO 27
<211> LENGTH: 13
<212> TYPE: PRT
<213> ORGANISM: Artificial sequence
<220> FEATURE:
<223> OTHER INFORMATION: Synthetic sequence

<400> SEQUENCE: 27

Lys Asn Gly Gly Pro Ser Ser Gly Ala Pro Pro Pro Ser
1               5                   10
```